US011634727B2

(12) United States Patent
Sun et al.

(10) Patent No.: US 11,634,727 B2
(45) Date of Patent: Apr. 25, 2023

(54) RECOMBINANT NUCLEIC ACID MOLECULE OF TRANSCRIPTIONAL CIRCULAR RNA AND ITS APPLICATION IN PROTEIN EXPRESSION

(71) Applicant: Purecodon (Hong Kong) Biopharma Ltd., Hong Kong (CN)

(72) Inventors: Zhenhua Sun, Suzhou (CN); Chijian Zuo, Suzhou (CN); Jiafeng Zhu, Suzhou (CN)

(73) Assignee: Purecodon (Hong Kong) Biopharma Ltd., Hong Kong (CN)

( * ) Notice: Subject to any disclaimer, the term of this patent is extended or adjusted under 35 U.S.C. 154(b) by 0 days.

(21) Appl. No.: 17/486,204

(22) Filed: Sep. 27, 2021

(65) Prior Publication Data

US 2022/0177910 A1 Jun. 9, 2022

Related U.S. Application Data

(63) Continuation of application No. 17/337,612, filed on Jun. 3, 2021.

(30) Foreign Application Priority Data

Dec. 4, 2020 (CN) ......................... 202011408937.4

(51) Int. Cl.

| | |
|---|---|
| ***A61K 48/00*** | (2006.01) |
| ***C12N 15/79*** | (2006.01) |
| ***C12N 15/85*** | (2006.01) |
| ***C07K 14/005*** | (2006.01) |
| ***C07K 14/47*** | (2006.01) |
| ***C07K 14/505*** | (2006.01) |
| ***C07K 14/54*** | (2006.01) |
| ***C07K 14/735*** | (2006.01) |
| ***C07K 16/28*** | (2006.01) |

(52) U.S. Cl.

CPC ............ *C12N 15/85* (2013.01); *C07K 14/005* (2013.01); *C07K 14/4748* (2013.01); *C07K 14/505* (2013.01); *C07K 14/5443* (2013.01); *C07K 14/70535* (2013.01); *C07K 16/2818* (2013.01); *C12N 2770/20022* (2013.01); *C12N 2840/203* (2013.01)

(58) Field of Classification Search

None

See application file for complete search history.

(56) References Cited

U.S. PATENT DOCUMENTS

| | | | | |
|---|---|---|---|---|
| 9,428,767 | B2 * | 8/2016 | Minshull | A61K 31/7105 |
| 11,203,767 | B2 * | 12/2021 | Anderson | A61K 48/005 |
| 11,352,640 | B2 * | 6/2022 | Anderson | C12N 15/85 |
| 11,352,641 | B2 * | 6/2022 | Anderson | C12N 15/79 |
| 11,447,796 | B2 * | 9/2022 | Anderson | C12N 15/11 |
| 2020/0080106 | A1 * | 3/2020 | Anderson | C12N 15/11 |
| 2020/0090106 | A1 | 3/2020 | Nakahara | |

FOREIGN PATENT DOCUMENTS

| | | | |
|---|---|---|---|
| CN | 110392577 A | | 10/2019 |
| CN | 111778256 A | | 10/2020 |
| CN | 112481289 | | 3/2021 |
| WO | WO 2015/157579 | * | 10/2015 |
| WO | WO 2019/236673 | | 12/2019 |
| WO | WO 2020180752 A1 | | 9/2020 |
| WO | WO 2020/219563 | | 10/2020 |
| WO | WO 2020198403 A2 | | 10/2020 |
| WO | WO 2020/237227 | | 11/2020 |

OTHER PUBLICATIONS

Oberste et al., J. Virol. 78 (2), 855-867 (2004) Evidence for frequent recombination within species human enterovirus B based on complete genomic sequences of all thirty-seven serotypes.*

Zhang et al et al., J. Med. Virol. 41 (2), 129-137 (1993) Attenuation of a reactivated cardiovirulent coxsackievirus B3: The 5'-nontranslated region does not contain major attenuation determinants.*

Kennell, Progr. Nucleic Acid Res. Mol. Biol. 11:259-301, 1971.*

Qing et al., Biomedical and Environmental Sciences vol. 29, Issue 10, Oct. 2016, pp. 767-772; Comparative Genomic Analysis of Enterovirus 71 Revealed Six New Potential Neurovirulence-associated Sites.*

Transcription (biology) From Wikipedia, the free encyclopedia; pp. 1-14; downloaded on Mar. 29, 2022.*

Single-nucleotide polymorphism From Wikipedia, the free encyclopedia pp. downloaded Mar. 31, 2022.*

Barrett et al., "Circular RNAs: analysis, expression and potential functions," Development, Jun. 1, 2016, 143:1838-1847.

Cech et al., "Biological Catalysis by RNA," Annual Review of Biochemistry, 1986, 55:559-629.

Cech et al., "Self-Splicing of Group I Introns," Annual Review of Biochemistry, 1990, 59:543-568.

(Continued)

*Primary Examiner* — Maria G Leavitt

(74) *Attorney, Agent, or Firm* — Fish & Richardson P.C.

(57) ABSTRACT

The present disclosure relates to a recombinant nucleic acid molecule of the transcriptional circular RNA and its application in protein expression. Specifically, the present disclosure relates to a recombinant nucleic acid molecule of the transcriptional circular RNA, recombinant expression vector, pre-circularized RNA, circular RNA, recombinant host cell, pharmaceutical composition and protein preparing method. The transcription product of the recombinant nucleic acid molecule in this present disclosure is a circular RNA which containing specific IRES element. IRES element can increase the protein expression level of circular RNA in eukaryotic cells, achieve efficient and persistent expression of protein. It has important application value in many fields like: Preparation of mRNA infectious disease vaccines, therapeutic mRNA tumor vaccines, mRNA-based dendritic cell tumor vaccines, mRNA-based gene therapy, mRNA-based chimeric antigen receptor T cell therapy, and protein supplement therapy.

8 Claims, 6 Drawing Sheets

Specification includes a Sequence Listing.

(56) References Cited

OTHER PUBLICATIONS

De Breyne et al., "Direct functional interaction of initiation factor eIF4G with type 1 internal ribosomal entry sites," Proceedings of the National Academy of Sciences USA, Jun. 2009, 106(23):9197-9202.

Kis et al., "Emerging technologies for low-cost, rapid vaccine manufacture," Biotechnology Journal, Dec. 10, 2018, 14(1):e1800376, 36 pages.

Liang et al., "Efficient Targeting and Activation of Antigen-Presenting Cells In Vivo after Modified mRNA Vaccine Administration in Rhesus Macaques," Molecular Therapy, Dec. 2017, 25(12):2635-2647.

Lima et al., "Short Poly(A) Tails are a Conserved Feature of Highly Expressed Genes," Nature Structural and Molecular Biology, Dec. 2017, 24(12):1057-1063, 20 pages.

Muller et al., "In vitro circularization of RNA," RNA Biology, 2017, 14(8):1018-1027.

Pardi et al., "mRNA vaccines—a new era in vaccinology," Nature Reviews Drug Discovery, Jan. 12, 2018, 17(4):261-279, 43 pages.

Pardi et al., "Nucleoside-modified mRNA vaccines induce potent T follicular helper and germinal center B cell responses," Journal of Experimental Medicine, May 8, 2018, 215(6):1571-1588.

Pardi et al., "Zika virus protection by a single low dose nucleoside modified mRNA vaccination," Nature, Mar. 9, 2017, 543(7644):248-251, 21 pages.

Puttaraju et al., "Group I permuted intron—exon (PIE) sequences self-splice to produce circular exons," Nucleic Acids Research, Oct. 25, 1992, 20(20):5357-5364.

Ramanathan et al., "mRNA capping: biological functions and applications," Nucleic Acids Research, Jun. 17, 2016, 44(16):7511-7526.

Sahin et al., "mRNA-based therapeutics—developing a new class of drugs," Nature Reviews Drug Discovery, Oct. 2014, 13:759-780.

Shirley et al., "Immune Responses to Viral Gene Therapy Vectors," Molecular Therapy, Mar. 2020, 28(3):709-722.

Wesselhoeft et al., "Engineering circular RNA for potent and stable translation in eukaryotic cells," Nature Conununications, 2018, 9:2629, 10 pages (Exhibit A).

\* cited by examiner

SEQUENCE LISTING

```
<160> NUMBER OF SEQ ID NOS: 53

<210> SEQ ID NO 1
<211> LENGTH: 19
<212> TYPE: DNA
<213> ORGANISM: Artificial Sequence
<220> FEATURE:
<223> OTHER INFORMATION: Sequence of the T7 promoter

<400> SEQUENCE: 1

taatacgact cactatagg                                                  19


<210> SEQ ID NO 2
<211> LENGTH: 21
<212> TYPE: DNA
<213> ORGANISM: Artificial Sequence
<220> FEATURE:
<223> OTHER INFORMATION: Sequence of 5'homology arm

<400> SEQUENCE: 2

accgtcagtt gctcactgtg c                                               21


<210> SEQ ID NO 3
<211> LENGTH: 21
<212> TYPE: DNA
<213> ORGANISM: Artificial Sequence
<220> FEATURE:
<223> OTHER INFORMATION: Sequence of 5'homology arm

<400> SEQUENCE: 3

accgtgctat gtccacgtgt c                                               21


<210> SEQ ID NO 4
<211> LENGTH: 131
<212> TYPE: DNA
<213> ORGANISM: Artificial Sequence
<220> FEATURE:
<223> OTHER INFORMATION: Sequence of the 3'intron

<400> SEQUENCE: 4

aacaatagat gacttacaac taatcggaag gtgcagagac tcgacgggag ctaccctaac     60

gtcaagacga gggtaaagag agagtccaat tctcaaagcc aataggcagt agcgaaagct    120

gcaagagaat g                                                         131


<210> SEQ ID NO 5
<211> LENGTH: 51
<212> TYPE: DNA
<213> ORGANISM: Artificial Sequence
<220> FEATURE:
<223> OTHER INFORMATION: Sequence of the second exon

<400> SEQUENCE: 5

aaaatccgtt gaccttaaac ggtcgtgtgg gttcaagtcc ctccaccccc a              51


<210> SEQ ID NO 6
<211> LENGTH: 50
<212> TYPE: DNA
```

<213> ORGANISM: Artificial Sequence
<220> FEATURE:
<223> OTHER INFORMATION: Sequence of 5'spacer

<400> SEQUENCE: 6
aaaaaacaaa aacaaaaaaa acaaaaaaac aaaaaaaaaa ccaaaacaca 50

<210> SEQ ID NO 7
<211> LENGTH: 50
<212> TYPE: DNA
<213> ORGANISM: Artificial Sequence
<220> FEATURE:
<223> OTHER INFORMATION: Sequence of 5'spacer

<400> SEQUENCE: 7
aaaaacaaaa aacaaaaaaa aaaccaaaaa aacaaaaaaa acaaaacaca 50

<210> SEQ ID NO 8
<211> LENGTH: 741
<212> TYPE: DNA
<213> ORGANISM: Artificial Sequence
<220> FEATURE:
<223> OTHER INFORMATION: IRES Sequence

<400> SEQUENCE: 8
ttaaaacagc ctgtgggttg atcccaccca caggcccatt gggcgctagc actctggtat 60
cacggtacct ttgtgcgcct gttttatacc ccctccccca actgtaactt agaagtaaca 120
cacaccgatc aacagtcagc gtggcacacc agccacgttt tgatcaagca cttctgttac 180
cccggactga gtatcaatag actgctcacg cggttgaagg agaaagcgtt cgttatccgg 240
ccaactactt cgaaaaacct agtaacaccg tggaagttgc agagtgtttc gctcagcact 300
accccagtgt agatcaggtc gatgagtcac cgcattcccc acgggcgacc gtggcggtgg 360
ctgcgttggc ggcctgccca tggggaaacc catgggacgc tctaatacag acatggtgcg 420
aagagtctat tgagctagtt ggtagtcctc cggcccctga atgcggctaa tcctaactgc 480
ggagcacaca ccctcaagcc agagggcagt gtgtcgtaac gggcaactct gcagcggaac 540
cgactacttt gggtgtccgt gtttcatttt attcctatac tggctgctta tggtgacaat 600
tgagagatcg ttaccatata gctattggat tggccatccg gtgactaata gagctattat 660
atatcccttt gttgggttta taccacttag cttgaaagag gttaaaacat tacaattcat 720
tgttaagttg aatacagcaa a 741

<210> SEQ ID NO 9
<211> LENGTH: 682
<212> TYPE: DNA
<213> ORGANISM: Artificial Sequence
<220> FEATURE:
<223> OTHER INFORMATION: IRES Sequence

<400> SEQUENCE: 9
ttaaaacagc ctgtgggttg cacccaccca cagggcccac agggcgctag cactctggta 60
tcacggtacc tttgtgcgcc tgttttatta ccccttcccc aattgaaaat tagaagcaat 120
gcacaccgat caacagcagg cgtggcgcac cagtcacgtc tcgatcaagc acttctgttt 180
ccccggaccg agtatcaata gactgctcac gcggttgaag gagaaagtgt tcgttatccg 240
gctaaccact tcgagaaacc cagtaacacc atgaaagttg cagggtgttt cgctcagcac 300
ttccccagtg tagatcaggt cgatgagtca ccgcgttccc cacgggcgac cgtggcggtg 360
gctgcgttgg cggcctgcct atgggttaac ccataggacg ctctaataca gacatggtgc 420
gaagagttta ttgagctggt tagtatccct ccggcccctg aatgcggcta atcctaactg 480
cggagcacgt gcctccaatc caggggggttg catgtcgtaa cgggtaactc tgcagcggaa 540
ccgactactt tgggtgtccg tgtttccttt tattcttata ctggctgctt atggtgacaa 600
tcgaggaatt gttaccatat agctattgga ttggccatcc ggtgtctaac agagcgatta 660
tatacctctt tgttggattt at 682

<210> SEQ ID NO 10
<211> LENGTH: 742
<212> TYPE: DNA
<213> ORGANISM: Artificial Sequence
<220> FEATURE:
<223> OTHER INFORMATION: IRES Sequence

<400> SEQUENCE: 10
ttaaaacagc ctgtgggttg atcccaccca cagggcccac tgggcgctag cactctggta 60
tcacggtacc tttgtgcgcc tgttttatac ttcctccccc aactgcaact tagaagtaac 120
acaaaccgat caacagtcag cgtggcacac cagccacgtt ttgatcaaac acttctgtta 180
ccccggactg agtatcaata gactgctcac gcggttgaag gagaaaacgt tcgttatccg 240
gccaactact tcgagaaacc tagtaacgcc atggaagttg tggagtgttt cgctcagcac 300
taccccagtg tagatcaggt tgatgagtca ccgcattccc cacgggtgac cgtggcggtg 360
gctgcgttgg cggcctgccc atggggaaac ccatgggacg ctcttataca gacatggtgc 420
gaagagtcta ttgagctagt tggtagtcct ccggcccctg aatgcggcta atcccaactg 480
cggagcatac actctcaagc cagagggtag tgtgtcgtaa tgggcaactc tgcagcggaa 540
ccgactactt tgggtgtccg tgtttcattt tattcctata ctggctgctt atggtgacaa 600
ttgagagatt gttaccatat agctattgga ttggccatcc ggtgactaac agagctatta 660
tatatctttt tgttgggttt ataccactta gcttgaaaga ggttaaaact ctacattaca 720
ttttaatact gaacaccgca aa 742

<210> SEQ ID NO 11
<211> LENGTH: 737
<212> TYPE: DNA
<213> ORGANISM: Artificial Sequence
<220> FEATURE:
<223> OTHER INFORMATION: IRES Sequence

<400> SEQUENCE: 11
ttaaaacagc ctgtgggttg atcccaccca cagggcccat tgggcgctag cactctggta 60
tcacggtacc cttgtgcgcc tgttttatgt cccttccctc aactgtaact tagaagtaac 120
gcacaccgat caacagtcag cgtggcacac cagccatgtt ttgatcaagc acttctgtta 180
ccccggaccg agtatcaaca gactgctcac gcggttgaag gagaaagtgt tcgttatccg 240
gccaactact tcgaaaaacc tagtaacacc atggaagttg cagagtgttt cgctcagcac 300
taccccagtg tagatcaggt cgatgagtca ccgcatcccc cacgggcgac cgtggcggtg 360
gctgcgttgg cggcctgcct atgggggaac ccataggacg ctctaataca gacatggtgc 420
gaagagtcca ttgagctagt tggtagtcct ccggcccctg aatgcggcta atcctaactg 480
cggagcacac accttcaagc cagagggcag tgtgtcgtaa cgggcaactc tgcagcggaa 540
ccgactactt tgggtgtccg tgtttcattt tattcttata ctggctgctt atggtgacaa 600
ttgagagatt gttaccatat agctattgga ttggccatcc agtgactagc agagctatta 660

-continued tatacctctt tgttgggttt ataccaccta atttgaaaga agttaaaaca ttagaattca 720
ttattaaatt gaataca 737

<210> SEQ ID NO 12
<211> LENGTH: 683
<212> TYPE: DNA
<213> ORGANISM: Artificial Sequence
<220> FEATURE:
<223> OTHER INFORMATION: IRES Sequence

<400> SEQUENCE: 12
ttaaaacagc ctgtgggttg cacccaccca cagggcccac agggcgctag cactctggta 60
tcacggtacc tttgtgcgcc tgttttatta ccccttcccc aattgaaaat tagaagcaat 120
gcacaccgat caacagcagg cgtggcgcac cagtcacgtc tcgatcaagc acttctgttt 180
ccccggaccg agtatcaata gactgctcac gcggttgaag gagaaagtgt tcgttatccg 240
gctaaccact tcgagaaacc cagtaacacc atgaaagttg cagggtgttt cgctcagcac 300
ttccccagtg tagatcaggt cgatgagtca ccgcgttccc cacgggcgac cgtggcggtg 360
gctgcgttgg cggcctgcct atgggttaac ccataggacg ctctaataca gacatggtgc 420
gaagagttta ttgagctggt tagtatctcc tccggcccct gaatgcggct aatcctaact 480
gcggagcaca caccctcaag ccagagggca gtgtgtcgta acgggcaact ctgcagcgga 540
accgactact ttgggtgtcc gtgtttcctt ttattcttat actggctgct tatggtgaca 600
atcgaggaat tgttaccata tagctattgg attggccatc cggtgtctaa cagagcgatt 660
atatacctct ttgttggatt tat 683

<210> SEQ ID NO 13
<211> LENGTH: 742
<212> TYPE: DNA
<213> ORGANISM: Artificial Sequence
<220> FEATURE:
<223> OTHER INFORMATION: IRES Sequence

<400> SEQUENCE: 13
ttaaaacagc ctgtgggttg atcccaccca cagggcccac tgggcgctag cactctggta 60
tcacggtacc tttgtgcgcc tgttttatac ttcctccccc aactgcaact tagaagtaac 120
acaaaccgat caacagtcag cgtggcacac cagccacgtt ttgatcaaac acttctgtta 180
ccccggactg agtatcaata gactgctcac gcggttgaag gagaaaacgt tcgttatccg 240
gccaactact tcgagaaacc tagtaacgcc atggaagttg tggagtgttt cgctcagcac 300
taccccagtg tagatcaggt tgatgagtca ccgcattccc cacgggtgac cgtggcggtg 360
gctgcgttgg cggcctgccc atggggaaac ccatgggacg ctcttataca gacatggtgc 420
gaagagtcta ttgagctagt tggtagtcct ccggcccctg aatgcggcta atcctaactg 480
cggagcacac accctcaagc cagagggcag tgtgtcgtaa cgggcaactc tgcagcggaa 540
ccgactactt tgggtgtccg tgtttcattt tattcctata ctggctgctt atggtgacaa 600
ttgagagatt gttaccatat agctattgga ttggccatcc ggtgactaac agagctatta 660
tatatctttt tgttgggttt ataccactta gcttgaaaga ggttaaaact ctacattaca 720
ttttaatact gaacaccgca aa 742

<210> SEQ ID NO 14
<211> LENGTH: 737
<212> TYPE: DNA
<213> ORGANISM: Artificial Sequence -continued
<220> FEATURE:
<223> OTHER INFORMATION: IRES Sequence

<400> SEQUENCE: 14
ttaaaacagc ctgtgggttg atcccaccca cagggcccat tgggcgctag cactctggta 60
tcacggtacc cttgtgcgcc tgttttatgt cccttccctc aactgtaact tagaagtaac 120
gcacaccgat caacagtcag cgtggcacac cagccatgtt ttgatcaagc acttctgtta 180
ccccggaccg agtatcaaca gactgctcac gcggttgaag gagaaagtgt tcgttatccg 240
gccaactact tcgaaaaacc tagtaacacc atggaagttg cagagtgttt cgctcagcac 300
taccccagtg tagatcaggt cgatgagtca ccgcatcccc cacgggcgac cgtggcggtg 360
gctgcgttgg cggcctgcct atggggaaac ccataggacg ctctaataca gacatggtgc 420
gaagagtcca ttgagctagt tggtagtcct ccggcccctg aatgcggcta atcctaactg 480
cggagcacac accctcaagc cagagggcag tgtgtcgtaa cgggcaactc tgcagcggaa 540
ccgactactt tgggtgtccg tgtttcattt tattcttata ctggctgctt atggtgacaa 600
ttgagagatt gttaccatat agctattgga ttggccatcc agtgactagc agagctatta 660
tatacctctt tgttgggttt ataccaccta atttgaaaga agttaaaaca ttagaattca 720
ttattaaatt gaataca 737

<210> SEQ ID NO 15
<211> LENGTH: 16
<212> TYPE: DNA
<213> ORGANISM: Artificial Sequence
<220> FEATURE:
<223> OTHER INFORMATION: Sequence of the first exon

<400> SEQUENCE: 15
agacgctacg gactta 16

<210> SEQ ID NO 16
<211> LENGTH: 114
<212> TYPE: DNA
<213> ORGANISM: Artificial Sequence
<220> FEATURE:
<223> OTHER INFORMATION: Sequence of the 5'intron

<400> SEQUENCE: 16
aataattgag ccttaaagaa gaaattcttt aagtggatgc tctcaaactc agggaaacct 60
aaatctagtt atagacaagg caatcctgag ccaagccgaa gtagtaatta gtaa 114

<210> SEQ ID NO 17
<211> LENGTH: 21
<212> TYPE: DNA
<213> ORGANISM: Artificial Sequence
<220> FEATURE:
<223> OTHER INFORMATION: Sequence of 3'homology arm

<400> SEQUENCE: 17
gcacagtgag caactgacgg a 21

<210> SEQ ID NO 18
<211> LENGTH: 21
<212> TYPE: DNA
<213> ORGANISM: Artificial Sequence
<220> FEATURE:
<223> OTHER INFORMATION: Sequence of 3'homology arm

<400> SEQUENCE: 18
gacacgtgga catagcacgg a 21

<210> SEQ ID NO 19
<211> LENGTH: 6
<212> TYPE: DNA
<213> ORGANISM: Artificial Sequence
<220> FEATURE:
<223> OTHER INFORMATION: Sequence of the XbaI restriction site

<400> SEQUENCE: 19 tctaga 6

<210> SEQ ID NO 20
<211> LENGTH: 720
<212> TYPE: DNA
<213> ORGANISM: Artificial Sequence
<220> FEATURE:
<223> OTHER INFORMATION: Sequence of EGFP encoding

<400> SEQUENCE: 20
atggtgtcaa agggtgagga attattcacc ggcgtggtgc ctatccttgt ggaacttgat 60
ggagatgtga acggacacaa attcagtgta tcaggagaag gagaaggaga tgcaacatac 120
ggaaagctca ctcttaaatt tatctgcaca acaggaaagc tcccggtgcc ttggcctaca 180
cttgtgacaa cacttacata cggagtgcaa tgcttctcgc gttaccctga tcacatgaaa 240
caacacgatt tcttcaagag tgcaatgcct gaaggatacg tgcaagaaag aacaatcttc 300
ttcaaggacg atggaaacta caagactcgt gcagaagtga aatttgaagg agatacactt 360
gtgaacagaa tcgaacttaa aggaatcgat ttcaaggagg atggaaacat ccttggacac 420
aaacttgaat acaactacaa ctcacacaac gtgtacatca tggcagataa acagaagaat 480
ggtatcaaag tgaactttaa gattcgccac aacatcgaag atggatcagt gcaacttgca 540
gatcactacc aacagaatac gccgatagga gatggacctg tgcttcttcc tgataaccac 600
tacctttcaa cacaatcagc actttcaaag gacccaaacg agaagcgaga ccacatggtg 660
cttcttgaat ttgtgacagc agcaggaatc acacttggaa tggatgaact ttacaaatga 720

<210> SEQ ID NO 21
<211> LENGTH: 239
<212> TYPE: PRT
<213> ORGANISM: Artificial Sequence
<220> FEATURE:
<223> OTHER INFORMATION: EGFP amino acid sequence

<400> SEQUENCE: 21

Met Val Ser Lys Gly Glu Glu Leu Phe Thr Gly Val Val Pro Ile Leu
1 5 10 15

Val Glu Leu Asp Gly Asp Val Asn Gly His Lys Phe Ser Val Ser Gly
20 25 30

Glu Gly Glu Gly Asp Ala Thr Tyr Gly Lys Leu Thr Leu Lys Phe Ile
35 40 45

Cys Thr Thr Gly Lys Leu Pro Val Pro Trp Pro Thr Leu Val Thr Thr
50 55 60

Leu Thr Tyr Gly Val Gln Cys Phe Ser Arg Tyr Pro Asp His Met Lys
65 70 75 80

Gln His Asp Phe Phe Lys Ser Ala Met Pro Glu Gly Tyr Val Gln Glu
85 90 95

Arg Thr Ile Phe Phe Lys Asp Asp Gly Asn Tyr Lys Thr Arg Ala Glu
100 105 110

```
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 22
<211> LENGTH: 1638
<212> TYPE: RNA
<213> ORGANISM: Artificial Sequence
<220> FEATURE:
<223> OTHER INFORMATION: Sequence of EGFP circular RNA

<400> SEQUENCE: 22

aaaauccguu gaccuuaaac ggucgugugg guucaagucc cuccaccccc acgccggaaa     60

cgcaauagcc gaaaaacaaa aaacaaaaaa aacaaaaaaa aaaccaaaaa aacaaaacac    120

auuaaaacag ccugugggu gaucccaccc acaggcccau ugggcgcuag cacucuggua    180

ucacgguacc uuugugcgcc uguuuuauac ccccuccccc aacuguaacu uagaaguaac    240

acacaccgau caacagucag cguggcacac cagccacguu uugaucaagc acuucuguua    300

ccccggacug aguaucaaua gacugcucac gcgguugaag gagaaagcgu ucguuauccg    360

gccaacuacu ucgaaaaacc uaguaacacc guggaaguug cagaguguuu cgcucagcac    420

uaccccagug uagaucaggu cgaugaguca ccgcauuccc cacgggcgac cguggcggug    480

gcugcguugg cggccugccc auggggaaac ccaugggacg cucuaauaca gacauggugc    540

gaagagucua uugagcuagu ugguaguccu ccggccccug aaugcggcua auccuaacug    600

cggagcacac acccucaagc cagagggcag ugugucguaa cgggcaacuc ugcagcggaa    660

ccgacuacuu ugggguguccg uguuucauuu uauuccuaua cuggcugcuu auggugacaa    720

uugagagauc guuaccauau agcuauugga uuggccaucc ggugacuaau agagcuauua    780

uauaucccuu uguuggguuu auaccacuua gcuugaaaga gguuaaaaca uuacaauuca    840

uuguuaaguu gaauacagca aaauggugc aaagggugag gaauuauuca ccggcguggu    900

gccuauccuu guggaacuug auggagaugu gaacggacac aaauucagug uaucaggaga    960

aggagaagga gaugcaacau acggaaagcu cacucuuaaa uuuaucugca caacaggaaa   1020

gcucccggug ccuuggccua cacuugugac aacacuuaca uacggagugc aaugcuucuc   1080

gcguuacccu gaucacauga aacaacacga uuucuucaag agugcaaugc cugaaggaua   1140

cgugcaagaa agaacaaucu ucuucaagga cgauggaaac uacaagacuc gugcagaagu   1200

gaaauuugaa ggagauacac uugugaacag aaucgaacuu aaaggaaucg auuucaagga   1260

ggauggaaac auccuuggac acaaacuuga auacaacuac aacucacaca acguguacau   1320

cauggcagau aaacagaaga augguaucaa agugaacuuu aagauucgcc acaacaucga   1380
```

-continued

```
agauggauca gugcaacuug cagaucacua ccaacagaau acgccgauag gagauggacc   1440

ugugcuucuu ccugauaacc acuaccuuuc aacacaauca gcacuuucaa aggacccaaa   1500

cgagaagcga gaccacaugg ugcuucuuga auuugugaca gcagcaggaa ucacacuugg   1560

aauggaugaa cuuuacaaau gaaaaaaaca aaaaacaaaa cggcuauuau gcguuaccgg   1620

cgagacgcua cggacuua                                                  1638
```

<210> SEQ ID NO 23
<211> LENGTH: 1579
<212> TYPE: RNA
<213> ORGANISM: Artificial Sequence
<220> FEATURE:
<223> OTHER INFORMATION: Sequence of EGFP circular RNA

<400> SEQUENCE: 23

```
aaaauccguu gaccuuaaac ggucguguggg guucaagucc cuccaccccc acgccggaaa     60

cgcaauagcc gaaaaacaaa aaacaaaaaa aacaaaaaaa aaaccaaaaa aacaaaacac    120

auuaaaacag ccuguggguu gcacccaccc acagggccca cagggcgcua gcacucuggu    180

aucacgguac cuuugugcgc cuguuuuauu accccuuccc caauugaaaa uuagaagcaa    240

ugcacaccga ucaacagcag gcguggcgca ccagucacgu cucgaucaag cacuucuguu    300

uccccggacc gaguaucaau agacugcuca cgcgguugaa ggagaaagug uucguuaucc    360

ggcuaaccac uucgagaaac ccaguaacac caugaaaguu gcaggguguu ucgcucagca    420

cuuccccagu guagaucagg ucgaugaguc accgcguucc ccacgggcga ccguggcggu    480

ggcugcguug gcggccugcc uauggguuaa cccauaggac gcucuaauac agacauggug    540

cgaagaguuu auugagcugg uuaguauccc uccggccccu gaaugcggcu aauccuaacu    600

gcggagcacg ugccuccaau ccagggggguu gcaugucgua acggguaacu cugcagcgga    660

accgacuacu uugggugucc guguuuccuu uuauucuuau acuggcugcu uauggugaca    720

aucgaggaau uguuaccaua uagcuauugg auuggccauc cggugucuaa cagagcgauu    780

auauaccucu uuguuggauu uauauggugu caaaggguga ggaauuauuc accggcgugg    840

ugccuauccu uguggaacuu gauggagaug ugaacggaca caaauucagu guaucaggag    900

aaggagaagg agaugcaaca uacggaaagc ucacucuuaa auuuaucugc acaacaggaa    960

agcuccccggu gccuuggccu acacuuguga caacacuuac auacggagug caaugcuucu   1020

cgcguuaccc ugaucacaug aaacaacacg auuucuucaa gagugcaaug ccugaaggau   1080

acgugcaaga aagaacaauc uucuucaagg acgauggaaa cuacaagacu cgugcagaag   1140

ugaaauuuga aggagauaca cuugugaaca gaaucgaacu uaaaggaauc gauuucaagg   1200

aggauggaaa cauccuugga cacaaacuug aauacaacua caacucacac aacguguaca   1260

ucauggcaga uaaacagaag aaugguauca aagugaacuu uaagauucgc cacaacaucg   1320

aagauggauc agugcaacuu gcagaucacu accaacagaa uacgccgaua ggagauggac   1380

cugugcuucu uccugauaac cacuaccuuu caacacaauc agcacuuuca aaggacccaa   1440

acgagaagcg agaccacaug gugcuucuug aauuugugac agcagcagga aucacacuug   1500

gaauggauga acuuuacaaa ugaaaaaaac aaaaaacaaa acggcuauua ugcguuaccg   1560

gcgagacgcu acggacuua                                                 1579
```

<210> SEQ ID NO 24
<211> LENGTH: 1580
<212> TYPE: RNA

<213> ORGANISM: Artificial Sequence
<220> FEATURE:
<223> OTHER INFORMATION: Sequence of EGFP circular RNA

<400> SEQUENCE: 24
aaaauccguu gaccuuaaac ggucguguggg guucaagucc cuccaccccc acgccggaaa 60
cgcaauagcc gaaaaacaaa aaacaaaaaa aacaaaaaaa aaaccaaaaa aacaaaacac 120
auuaaaacag ccuguggguu gcacccaccc acagggccca cagggcgcua gcacucuggu 180
aucacgguac cuuugugcgc cuguuuuauu accccuuccc caauugaaaa uuagaagcaa 240
ugcacaccga ucaacagcag gcguggcgca ccagucacgu cucgaucaag cacuucuguu 300
uccccggacc gaguaucaau agacugcuca cgcgguugaa ggagaaagug uucguuaucc 360
ggcuaaccac uucgagaaac ccaguaacac caugaaaguu gcagggugau ucgcucagca 420
cuuccccagu guagaucagg ucgaugaguc accgcguucc ccacgggcga ccguggcggu 480
ggcugcguug gcggccugcc uaugggguaa cccauaggac gcucuaauac agacauggug 540
cgaagaguuu auugagcugg uuaguaucuc cuccggcccc ugaaugcggc uaauccuaac 600
ugcggagcac acacccucaa gccagagggc agugugucgu aacgggcaac ucugcagcgg 660
aaccgacuac uuuggguguc cguguuuccu uuuauucuua uacuggcugc uuauggugac 720
aaucgaggaa uuguuaccau auagcuauug gauuggccau ccggugucua acagagcgau 780
uauauaccuc uuuguuggau uuauauggug ucaaagggug aggaauuauu caccggcgug 840
gugccuaucc uuguggaacu ugauggagau gugaacggac acaaauucag uguaucagga 900
gaaggagaag gagaugcaac auacggaaag cucacucuua aauuuaucug cacaacagga 960
aagcucccgg ugccuuggcc uacacuugug acaacacuua cauacggagu gcaaugcuuc 1020
ucgcguuacc cugaucacau gaaacaacac gauuucuuca agagugcaau gccugaagga 1080
uacgugcaag aaagaacaau cuucuucaag gacgauggaa acuacaagac ucgugcagaa 1140
gugaaauuug aaggagauac acuugugaac agaaucgaac uuaaaggaau cgauuucaag 1200
gaggauggaa acauccuugg acacaaacuu gaauacaacu acaacucaca caacguguac 1260
aucauggcag auaaacagaa gaaugguauc aaagugaacu uuaagauucg ccacaacauc 1320
gaagauggau cagugcaacu ugcagaucac uaccaacaga auacgccgau aggagaugga 1380
ccugugcuuc uuccugauaa ccacuaccuu ucaacacaau cagcacuuuc aaaggaccca 1440
aacgagaagc gagaccacau ggugcuucuu gaauuuguga cagcagcagg aaucacacuu 1500
ggaauggaug aacuuuacaa augaaaaaaa caaaaaacaa aacggcuauu augcguuacc 1560
ggcgagacgc uacggacuua 1580

<210> SEQ ID NO 25
<211> LENGTH: 1639
<212> TYPE: RNA
<213> ORGANISM: Artificial Sequence
<220> FEATURE:
<223> OTHER INFORMATION: Sequence of EGFP circular RNA

<400> SEQUENCE: 25
aaaauccguu gaccuuaaac ggucgugugg guucaagucc cuccaccccc acgccggaaa 60
cgcaauagcc gaaaaacaaa aaacaaaaaa aacaaaaaaa aaaccaaaaa aacaaaacac 120
auuaaaacag ccuguggguu gaucccaccc acagggccca cugggcgcua gcacucuggu 180
aucacgguac cuuugugcgc cuguuuuaua cuuccucccc caacugcaac uuagaaguaa 240
cacaaaccga ucaacaguca gcguggcaca ccagccacgu uuugaucaaa cacuucuguu 300

-continued

```
accccggacu gaguaucaau agacugcuca cgcgguugaa ggagaaaacg uucguuaucc    360
ggccaacuac uucgagaaac cuaguaacgc cauggaaguu guggaguguu ucgcucagca    420
cuaccccagu guagaucagg uugaugaguc accgcauucc ccacggguga ccguggcggu    480
ggcugcguug gcggccugcc caugggggaaa cccaugggac gcucuuauac agacauggug    540
cgaagagucu auugagcuag uugguagucc uccggccccu gaaugcggcu aaucccaacu    600
gcggagcaua cacucucaag ccagagggua gugugucgua augggcaacu cugcagcgga    660
accgacuacu uugggugucc guguuucauu uuauuccuau acuggcugcu uauggugaca    720
auugagagau uguuaccaua uagcuauugg auuggccauc cggugacuaa cagagcuauu    780
auauaucuuu uuguugggu uauaccacuu agcuugaaag agguuaaaac ucuacauuac    840
auuuuaauac ugaacaccgc aaaauggugu caaaggguga ggaauuauuc accggcgugg    900
ugccuauccu uguggaacuu gauggagaug ugaacggaca caaauucagu guaucaggag    960
aaggagaagg agaugcaaca uacggaaagc ucacucuuaa auuuaucugc acaacaggaa   1020
agcucccggu gccuuggccu acacuuguga caacacuuac auacggagug caaugcuucu   1080
cgcguuaccc ugaucacaug aaacaacacg auuucuucaa gagugcaaug ccugaaggau   1140
acgugcaaga aagaacaauc uucuucaagg acgauggaaa cuacaagacu cgugcagaag   1200
ugaaauuuga aggagauaca cuugugaaca gaaucgaacu uaaaggaauc gauuucaagg   1260
aggauggaaa cauccuugga cacaaacuug aauacaacua caacucacac aacguguaca   1320
ucauggcaga uaaacagaag aaugguauca aagugaacuu uaagauucgc cacaacaucg   1380
aagauggauc agugcaacuu gcagaucacu accaacagaa uacgccgaua ggagauggac   1440
cugugcuucu uccugauaac cacuaccuuu caacacaauc agcacuuuca aaggacccaa   1500
acgagaagcg agaccacaug gugcuucuug aauuugugac agcagcagga aucacacuug   1560
gaauggauga acuuuacaaa ugaaaaaaac aaaaaacaaa acggcuauua ugcguuaccg   1620
gcgagacgcu acggacuua                                                1639
```

<210> SEQ ID NO 26
<211> LENGTH: 1639
<212> TYPE: RNA
<213> ORGANISM: Artificial Sequence
<220> FEATURE:
<223> OTHER INFORMATION: Sequence of EGFP circular RNA

<400> SEQUENCE: 26

```
aaaauccguu gaccuuaaac ggucgugugg guucaagucc cuccaccccc acgccggaaa     60
cgcaauagcc gaaaaacaaa aaacaaaaaa aacaaaaaaa aaaccaaaaa aacaaaacac    120
auuaaaacag ccuguggguu gaucccaccc acagggccca cugggcgcua gcacucuggu    180
aucacgguac cuuugugcgc cuguuuuaua cuuccucccc caacugcaac uuagaaguaa    240
cacaaaccga ucaacaguca gcguggcaca ccagccacgu uuugaucaaa cacuucuguu    300
accccggacu gaguaucaau agacugcuca cgcgguugaa ggagaaaacg uucguuaucc    360
ggccaacuac uucgagaaac cuaguaacgc cauggaaguu guggaguguu ucgcucagca    420
cuaccccagu guagaucagg uugaugaguc accgcauucc ccacggguga ccguggcggu    480
ggcugcguug gcggccugcc cauggggaaa cccaugggac gcucuuauac agacauggug    540
cgaagagucu auugagcuag uugguagucc uccggccccu gaaugcggcu aauccuaacu    600
gcggagcaca cacccucaag ccagagggca gugugucgua acgggcaacu cugcagcgga    660
```

```
accgacuacu uugggugucc guguuucauu uuauuccuau acuggcugcu uauggugaca    720

auugagagau uguuaccaua uagcuauugg auuggccauc cggugacuaa cagagcuauu    780

auauaucuuu uuguuggguu uauaccacuu agcuugaaag agguuaaaac ucuacauuac    840

auuuuaauac ugaacaccgc aaaauggugu caaaggguga ggaauuauuc accggcgugg    900

ugccuauccu uguggaacuu gauggagaug ugaacggaca caaauucagu guaucaggag    960

aaggagaagg agaugcaaca uacggaaagc ucacucuuaa auuuaucugc acaacaggaa   1020

agcucccggu gccuuggccu acacuuguga caacacuuac auacggagug caaugcuucu   1080

cgcguuaccc ugaucacaug aaacaacacg auuucuucaa gagugcaaug ccugaaggau   1140

acgugcaaga aagaacaauc uucuucaagg acgauggaaa cuacaagacu cgugcagaag   1200

ugaaauuuga aggagauaca cuugugaaca gaaucgaacu uaaaggaauc gauuucaagg   1260

aggauggaaa cauccuugga cacaaacuug aauacaacua caacucacac aacguguaca   1320

ucauggcaga uaaacagaag aaugguauca aagugaacuu uaagauucgc cacaacaucg   1380

aagauggauc agugcaacuu gcagaucacu accaacagaa uacgccgaua ggagauggac   1440

cugugcuucu uccugauaac cacuaccuuu caacacaauc agcacuuuca aaggacccaa   1500

acgagaagcg agaccacaug gugcuucuug aauuugugac agcagcagga aucacacuug   1560

gaauggauga acuuuacaaa ugaaaaaaac aaaaaacaaa acggcuauua ugcguuaccg   1620

gcgagacgcu acggacuua                                                1639
```

<210> SEQ ID NO 27
<211> LENGTH: 1634
<212> TYPE: RNA
<213> ORGANISM: Artificial Sequence
<220> FEATURE:
<223> OTHER INFORMATION: Sequence of EGFP circular RNA

<400> SEQUENCE: 27

```
aaaauccguu gaccuuaaac ggucguguggguucaagucc cuccaccccc acgccggaaa     60
```

```
cgcaauagcc gaaaaacaaa aaacaaaaaa aacaaaaaaa aaaccaaaaa aacaaaacac    120

auuaaaacag ccugugggguu gaucccaccc acagggccca uugggcgcua gcacucuggu    180

aucacgguac ccuugugcgc cuguuuuaug ucccuucccu caacuguaac uuagaaguaa    240

cgcacaccga ucaacaguca gcguggcaca ccagccaugu uuugaucaag cacuucuguu    300

accccggacc gaguaucaac agacugcuca cgcgguugaa ggagaaagug uucguuaucc    360

ggccaacuac uucgaaaaac cuaguaacac cauggaaguu gcagaguguu ucgcucagca    420

cuaccccagu guagaucagg ucgaugaguc accgcauccc ccacgggcga ccguggcggu    480

ggcugcguug gcggccugcc uauggggga cccauaggac gcucuaauac agacauggug    540

cgaagagucc auugagcuag uugguagucc uccggccccu gaaugcggcu aauccuaacu    600

gcggagcaca caccuucaag ccagagggca gugugucgua acgggcaacu cugcagcgga    660

accgacuacu uugggugucc guguuucauu uuauucuuau acuggcugcu uauggugaca    720

auugagagau uguuaccaua uagcuauugg auuggccauc cagugacuag cagagcuauu    780

auauaccucu uuguuggguu uauaccaccu aauuugaaag aaguuaaaac auuagaauuc    840

auuauuaaau ugaauacaau ggugucaaag ggugaggaau uauucaccgg cguggugccu    900

auccuugugg aacuugaugg agaugugaac ggacacaaau ucaguguauc aggagaagga    960

gaaggagaug caacauacgg aaagcucacu cuuaaauuua ucugcacaac aggaaagcuc   1020

ccggugccuu ggccuacacu ugugacaaca cuuacauacg gagugcaaug cuucucgcgu   1080
```

-continued

```
uacccugauc acaugaaaca acacgauuuc uucaagagug caaugccuga aggauacgug   1140

caagaaagaa caaucuucuu caaggacgau ggaaacuaca agacucgugc agaagugaaa   1200

uuugaaggag auacacuugu gaacagaauc gaacuuaaag gaaucgauuu caaggaggau   1260

ggaaacaucc uuggacacaa acuugaauac aacuacaacu cacacaacgu guacaucaug   1320

gcagauaaac agaagaaugg uaucaaagug aacuuuaaga uucgccacaa caucgaagau   1380

ggaucagugc aacuugcaga ucacuaccaa cagaauacgc cgauaggaga uggaccugug   1440

cuucuuccug auaaccacua ccuuucaaca caaucagcac uuucaaagga cccaaacgag   1500

aagcgagacc acaugguguu ucuugaauuu gugacagcag caggaaucac acuuggaaug   1560

gaugaacuuu acaaaugaaa aaaacaaaaa acaaaacggc uauuaugcgu uaccggcgag   1620

acgcuacgga cuua                                                     1634
```

<210> SEQ ID NO 28
<211> LENGTH: 1634
<212> TYPE: RNA
<213> ORGANISM: Artificial Sequence
<220> FEATURE:
<223> OTHER INFORMATION: Sequence of EGFP circular RNA

<400> SEQUENCE: 28

```
aaaauccguu gaccuuaaac ggucgugugg guucaagucc cuccaccccc acgccggaaa     60

cgcaauagcc gaaaaacaaa aaacaaaaaa aacaaaaaaa aaaccaaaaa aacaaaacac    120

auuaaaacag ccugugggu gaucccaccc acagggccca uugggcgcua gcacucuggu    180

aucacgguac ccuugugcgc cuguuuuaug ucccuucccu caacuguaac uuagaaguaa    240

cgcacaccga ucaacaguca gcguggcaca ccagccaugu uuugaucaag cacuucuguu    300

accccggacc gaguaucaac agacugcuca cgcgguugaa ggagaaagug uucguuaucc    360

ggccaacuac uucgaaaaac cuaguaacac cauggaaguu gcagaguguu ucgcucagca    420

cuaccccagu guagaucagg ucgaugaguc accgcauccc ccacgggcga ccguggcggu    480

ggcugcguug gcggccugcc uaugggggaa cccauaggac gcucuaauac agacauggug    540

cgaagagucc auugagcuag uugguagucc uccggccccu gaaugcggcu aauccuaacu    600

gcggagcaca cacccucaag ccagagggca gugugucgua acgggcaacu cugcagcgga    660

accgacuacu uuggguguuc guguuucauu uuauucuuau acuggcugcu uauggugaca    720

auugagagau uguuaccaua uagcuauugg auuggccauc cagugacuag cagagcuauu    780

auauaccucu uuguuggguu uauaccaccu aauuugaaag aaguuaaaac auuagaauuc    840

auuauuaaau ugaauacaau ggugucaaag ggugaggaau uauucaccgg cguggugccu    900

auccuugugg aacuugaugg agaugugaac ggacacaaau ucaguguauc aggagaagga    960

gaaggagaug caacauacgg aaagcucacu cuuaaauuua ucugcacaac aggaaagcuc   1020

ccggugccuu ggccuacacu ugugacaaca cuuacauacg gagugcaaug cuucucgcgu   1080

uacccugauc acaugaaaca acacgauuuc uucaagagug caaugccuga aggauacgug   1140

caagaaagaa caaucuucuu caaggacgau ggaaacuaca agacucgugc agaagugaaa   1200

uuugaaggag auacacuugu gaacagaauc gaacuuaaag gaaucgauuu caaggaggau   1260

ggaaacaucc uuggacacaa acuugaauac aacuacaacu cacacaacgu guacaucaug   1320

gcagauaaac agaagaaugg uaucaaagug aacuuuaaga uucgccacaa caucgaagau   1380

ggaucagugc aacuugcaga ucacuaccaa cagaauacgc cgauaggaga uggaccugug   1440
```

cuucuuccug auaaccacua ccuuucaaca caaucagcac uuucaaagga cccaaacgag 1500
aagcgagacc acauggugcu ucuugaauuu gugacagcag caggaaucac acuuggaaug 1560
gaugaacuuu acaaaugaaa aaaacaaaaa acaaaacggc uauuaugcgu uaccggcgag 1620
acgcuacgga cuua 1634

<210> SEQ ID NO 29
<211> LENGTH: 1645
<212> TYPE: RNA
<213> ORGANISM: Artificial Sequence
<220> FEATURE:
<223> OTHER INFORMATION: Sequence of EGFP circular RNA

<400> SEQUENCE: 29
aaaauccguu gaccuuaaac ggucguguggg guucaagucc cuccaccccc acgccggaaa 60
cgcaauagcc gaaaaaacaa aaacaaaaaa aacaaaaaaa caaaaaaaaa accaaaacac 120
auuaaaacag ccuguggguu gaucccaccc acagggccca cugggcgcua gcacucuggu 180
aucacgguac cuuugugcgc cuguuuuaua cuuccucccc caacugcaac uuagaaguaa 240
cacaaaccga ucaacaguca gcguggcaca ccagccacgu uuugaucaaa cacuucuguu 300
accccggacu gaguaucaau agacugcuca cgcgguugaa ggagaaaacg uucguuaucc 360
ggccaacuac uucgagaaac cuaguaacgc cauggaaguu guggaguguu ucgcucagca 420
cuaccccagu guagaucagg uugaugaguc accgcauucc ccacggguga ccguggcggu 480
ggcugcguug gcggccugcc cauggggaaa cccaugggac gcucuuauac agacauggug 540
cgaagagucu auugagcuag uugguagucc uccggccccu gaaugcggcu aaucccaacu 600
gcggagcaua cacucucaag ccagagggua gugugucgua augggcaacu cugcagcgga 660
accgacuacu uuggguguccc guguuucauu uuauuccuau acuggcugcu uauggugaca 720
auugagagau uguuaccaua uagcuauugg auuggccauc cggugacuaa cagagcuauu 780
auauaucuuu uuguuggguu uauaccacuu agcuugaaag agguuaaaac ucuacauuac 840
auuuuaauac ugaacaccgc aaaauggugu caaaggguga ggaauuauuc accggcgugg 900
ugccuauccu uguggaacuu gauggagaug ugaacggaca caaauucagu guaucaggag 960
aaggagaagg agaugcaaca uacggaaagc ucacucuuaa auuuaucugc acaacaggaa 1020
agcucccggu gccuuggccu acacuuguga caacacuuac auacggagug caaugcuucu 1080
cgcguuaccc ugaucacaug aaacaacacg auuucuucaa gagugcaaug ccugaaggau 1140
acgugcaaga aagaacaauc uucuucaagg acgauggaaa cuacaagacu cgugcagaag 1200
ugaaauuuga aggagauaca cuugugaaca gaaucgaacu uaaaggaauc gauuucaagg 1260
aggauggaaa cauccuugga cacaaacuug aauacaacua caacucacac aacguguaca 1320
ucauggcaga uaaacagaag aaugguauca aagugaacuu uaagauucgc cacaacaucg 1380
aagauggauc agugcaacuu gcagaucacu accaacagaa uacgccgaua ggagauggac 1440
cugugcuucu uccugauaac cacuaccuuu caacacaauc agcacuuuca aaggacccaa 1500
acgagaagcg agaccacaug gugcuucuug aauuugugac agcagcagga aucacacuug 1560
gaauggauga acuuuacaaa ugaaaaaaaa caaaaaaaca aaacaaacgg cuauuaugcg 1620
uuaccggcga gacgcuacgg acuua 1645

<210> SEQ ID NO 30
<211> LENGTH: 1642
<212> TYPE: RNA
<213> ORGANISM: Artificial Sequence -continued
<220> FEATURE:
<223> OTHER INFORMATION: Sequence of EGFP circular RNA

<400> SEQUENCE: 30
aaaauccguu gaccuuaaac ggucguguggg guucaagucc cuccaccccc acgccggaaa 60
cgcaauagcc gaaaaacaaa aaacaaaaaa aaaaccaaaa aaacaaaaaa aacaaaacac 120
auuaaaacag ccugugggguu gaucccaccc acagggccca cugggcgcua gcacucuggu 180
aucacgguac cuuugugcgc cuguuuuaua cuuccucccc caacugcaac uuagaaguaa 240
cacaaaccga ucaacaguca gcguggcaca ccagccacgu uuugaucaaa cacuucuguu 300
accccggacu gaguaucaau agacugcuca cgcgguugaa ggagaaaacg uucguuaucc 360
ggccaacuac uucgagaaac cuaguaacgc cauggaaguu guggaguguu ucgcucagca 420
cuaccccagu guagaucagg uugaugaguc accgcauucc ccacggguga ccguggcggu 480
ggcugcguug gcggccugcc caugggggaaa cccaugggac gcucuuauac agacauggug 540
cgaagagucu auugagcuag uugguagucc uccggccccu gaaugcggcu aaucccaacu 600
gcggagcaua cacucucaag ccagagggua gugugucgua augggcaacu cugcagcgga 660
accgacuacu uugggugucc guguuucauu uuauuccuau acuggcugcu uaugguguga 720
auugagagau uguuaccaua uagcuauugg auuggccauc cggugacuaa cagagcuauu 780
auauaucuuu uuguugggguu uauaccacuu agcuugaaag agguuaaaac ucuacauuac 840
auuuuaauac ugaacaccgc aaaauggugu caaaggguga ggaauuauuc accggcgugg 900
ugccuauccu uguggaacuu gauggagaug ugaacggaca caaauucagu guaucaggag 960
aaggagaagg agaugcaaca uacggaaagc ucacucuuaa auuuaucugc acaacaggaa 1020
agcucccggu gccuuggccu acacuuguga caacacuuac auacggagug caaugcuucu 1080
cgcguuaccc ugaucacaug aaacaacacg auuucuucaa gagugcaaug ccugaaggau 1140
acgugcaaga aagaacaauc uucuucaagg acgauggaaa cuacaagacu cgugcagaag 1200
ugaaauuuga aggagauaca cuugugaaca gaaucgaacu uaaaggaauc gauuucaagg 1260
aggauggaaa cauccuugga cacaaacuug aauacaacua caacucacac aacguguaca 1320
ucauggcaga uaaacagaag aaugguauca aagugaacuu uaagauucgc cacaacaucg 1380
aagauggauc agugcaacuu gcagaucacu accaacagaa uacgccgaua ggagauggac 1440
cugugcuucu uccugauaac cacuaccuuu caacacaauc agcacuuuca aaggacccaa 1500
acgagaagcg agaccacaug gugcuucuug aauuugugac agcagcagga aucacacuug 1560
gaauggauga acuuuacaaa ugaaaaaaca aaaaacaaaa caaacggcua uuaugcguua 1620
ccggcgagac gcuacggacu ua 1642

<210> SEQ ID NO 31
<211> LENGTH: 822
<212> TYPE: DNA
<213> ORGANISM: Artificial Sequence
<220> FEATURE:
<223> OTHER INFORMATION: Sequence of RBD encoding DNA

<400> SEQUENCE: 31
atgtttgtgt tcctggtgct gctgcctctg gtgtctaggg tgcagcctac agagagcatt 60
gtgaggttcc ctaacatcac caacctgtgc ccttttggag aggtgttcaa tgccacaagg 120
tttgcctctg tgtatgcctg gaataggaag aggatcagca actgtgtggc tgactactct 180
gtgctgtaca actctgctag cttcagcacc ttcaagtgct atggagtgag ccctaccaag 240

-continued

```
ctgaatgacc tgtgcttcac caatgtgtat gctgacagct ttgtgattag gggagatgag    300

gtgaggcaga ttgcccctgg acagactggc aagattgctg actacaacta caagctgcct    360

gatgacttca ctggctgtgt gattgcctgg aacagcaaca acctggacag caaggtggga    420

ggcaactaca actacctgta taggctgttt aggaagagca acctgaagcc ttttgagagg    480

gacatcagca cagagatcta ccaagctggc agcacccctt gcaatggagt ggagggcttc    540

aactgctact tccctctgca gagctatggc tttcagccta ccaatggagt gggctatcag    600

ccttataggg tggtggtgct gagctttgag ctgctgcatg cccctgccac agtgtgtggc    660

cctaagaaga gcaccaacct ggtgaagaac aagtgtgtga acttcagctc tggcctggtg    720

cctaccggct ctggctctgg ctacatccct gaggccccta gggatggcca agcctatgtg    780

aggaaggatg gagagtgggt gctgctgagc accttcctgt ga                       822
```

```
<210> SEQ ID NO 32
<211> LENGTH: 273
<212> TYPE: PRT
<213> ORGANISM: Artificial Sequence
<220> FEATURE:
<223> OTHER INFORMATION: Amino acid sequence of the RBD protein

<400> SEQUENCE: 32

Met Phe Val Phe Leu Val Leu Leu Pro Leu Val Ser Arg Val Gln Pro
1               5                   10                  15

Thr Glu Ser Ile Val Arg Phe Pro Asn Ile Thr Asn Leu Cys Pro Phe
            20                  25                  30

Gly Glu Val Phe Asn Ala Thr Arg Phe Ala Ser Val Tyr Ala Trp Asn
        35                  40                  45

Arg Lys Arg Ile Ser Asn Cys Val Ala Asp Tyr Ser Val Leu Tyr Asn
    50                  55                  60

Ser Ala Ser Phe Ser Thr Phe Lys Cys Tyr Gly Val Ser Pro Thr Lys
65                  70                  75                  80

Leu Asn Asp Leu Cys Phe Thr Asn Val Tyr Ala Asp Ser Phe Val Ile
                85                  90                  95

Arg Gly Asp Glu Val Arg Gln Ile Ala Pro Gly Gln Thr Gly Lys Ile
            100                 105                 110

Ala Asp Tyr Asn Tyr Lys Leu Pro Asp Asp Phe Thr Gly Cys Val Ile
        115                 120                 125

Ala Trp Asn Ser Asn Asn Leu Asp Ser Lys Val Gly Gly Asn Tyr Asn
    130                 135                 140

Tyr Leu Tyr Arg Leu Phe Arg Lys Ser Asn Leu Lys Pro Phe Glu Arg
145                 150                 155                 160

Asp Ile Ser Thr Glu Ile Tyr Gln Ala Gly Ser Thr Pro Cys Asn Gly
                165                 170                 175

Val Glu Gly Phe Asn Cys Tyr Phe Pro Leu Gln Ser Tyr Gly Phe Gln
            180                 185                 190

Pro Thr Asn Gly Val Gly Tyr Gln Pro Tyr Arg Val Val Val Leu Ser
        195                 200                 205

Phe Glu Leu Leu His Ala Pro Ala Thr Val Cys Gly Pro Lys Lys Ser
    210                 215                 220

Thr Asn Leu Val Lys Asn Lys Cys Val Asn Phe Ser Ser Gly Leu Val
225                 230                 235                 240

Pro Thr Gly Ser Gly Ser Gly Tyr Ile Pro Glu Ala Pro Arg Asp Gly
                245                 250                 255

Gln Ala Tyr Val Arg Lys Asp Gly Glu Trp Val Leu Leu Ser Thr Phe
```

260 265 270

Leu

<210> SEQ ID NO 33
<211> LENGTH: 1747
<212> TYPE: RNA
<213> ORGANISM: Artificial Sequence
<220> FEATURE:
<223> OTHER INFORMATION: Sequence of RBD circular RNA

<400> SEQUENCE: 33
aaaauccguu gaccuuaaac ggucgugugg guucaagucc cuccaccccc acgccggaaa 60
cgcaauagcc gaaaaaacaa aaacaaaaaa aacaaaaaaa caaaaaaaaa accaaaacac 120
auuaaaacag ccuguggguu gaucccaccc acagggccca cugggcgcua gcacucuggu 180
aucacgguac cuuugugcgc cuguuuuaua cuuccucccc caacugcaac uuagaaguaa 240
cacaaaccga ucaacaguca gcguggcaca ccagccacgu uuugaucaaa cacuucuguu 300
accccggacu gaguaucaau agacugcuca cgcgguugaa ggagaaaacg uucguuaucc 360
ggccaacuac uucgagaaac cuaguaacgc cauggaaguu guggaguguu ucgcucagca 420
cuaccccagu guagaucagg uugaugaguc accgcauucc ccacggguga ccguggcggu 480
ggcugcguug gcggccugcc caugggaaa cccaugggac gcucuuauac agacauggug 540
cgaagagucu auugagcuag uugguagucc uccggccccu gaaugcggcu aaucccaacu 600
gcggagcaua cacucucaag ccagagggua gugugucgua augggcaacu cugcagcgga 660
accgacuacu uugggugucc guguuucauu uuauuccuau acuggcugcu uauggugaca 720
auugagagau uguuaccaua uagcuauugg auuggccauc cggugacuaa cagagcuauu 780
auauaucuuu uuguuggguu uauaccacuu agcuugaaag agguuaaaac ucuacauuac 840
auuuuaauac ugaacaccgc aaaauguuug uguuccuggu gcugcugccu cuggugucua 900
gggugcagcc uacagagagc auugugaggu ucccuaacau caccaaccug ugcccuuuug 960
gagagguguu caaugccaca agguuugccu cuguguaugc cuggaauagg aagaggauca 1020
gcaacugugu ggcugacuac ucugugcugu acaacucugc uagcuucagc accuucaagu 1080
gcuauggagu gagcccuacc aagcugaaug accugugcuu caccaaugug uaugcugaca 1140
gcuuugugau uaggggagau gaggugaggc agauugcccc uggacagacu ggcaagauug 1200
cugacuacaa cuacaagcug ccugaugacu ucacuggcug ugugauugcc uggaacagca 1260
acaaccugga cagcaaggug ggaggcaacu acaacuaccu guauaggcug uuuaggaaga 1320
gcaaccugaa gccuuuugag agggacauca gcacagagau cuaccaagcu ggcagcaccc 1380
cuugcaaugg aguggagggc uucaacugcu acuucccucu gcagagcuau ggcuuucagc 1440
cuaccaaugg agugggcuau cagccuuaua ggguggguggu gcugagcuuu gagcugcugc 1500
augccccugc cacagugugu ggcccuaaga agagcaccaa ccuggugaag aacaagugug 1560
ugaacuucag cucuggccug gugccuaccg gcucuggcuc uggcuacauc ccugaggccc 1620
cuagggaugg ccaagccuau gugaggaagg auggagagug ggugcugcug agcaccuucc 1680
ugugaaaaaa aacaaaaaaa caaaacaaac ggcuauuaug cguuaccggc gagacgcuac 1740
ggacuua 1747

<210> SEQ ID NO 34
<211> LENGTH: 579
<212> TYPE: DNA
<213> ORGANISM: Artificial Sequence
<220> FEATURE:
<223> OTHER INFORMATION: Sequence of EPO encoding DNA

<400> SEQUENCE: 34

```
atgggcgtgc acgagtgccc cgcctggctg tggctgctgc tgagcctgct gagcctgccc      60

ctgggcctgc ccgtgctggg cgcccccccc aggctgatct gcgacagcag ggtgctggag     120

aggtacctgc tggaggccaa ggaggccgag aacatcacca ccggctgcgc cgagcactgc     180

agcctgaacg agaacatcac cgtgcccgac accaaggtga acttctacgc ctggaagagg     240

atggaggtgg gccagcaggc cgtggaggtg tggcagggcc tggccctgct gagcgaggcc     300

gtgctgaggg gccaggccct gctggtgaac agcagccagc cctgggagcc cctgcagctg     360

cacgtggaca aggccgtgag cggcctgagg agcctgacca ccctgctgag ggccctgggc     420

gcccagaagg aggccatcag ccccccccgac gccgccagcg ccgccccccct gaggaccatc     480

accgccgaca ccttcaggaa gctgttcagg gtgtacagca acttcctgag gggcaagctg     540

aagctgtaca ccggcgaggc ctgcaggacc ggcgacagg                            579
```

<210> SEQ ID NO 35
<211> LENGTH: 193
<212> TYPE: PRT
<213> ORGANISM: Artificial Sequence
<220> FEATURE:
<223> OTHER INFORMATION: Amino acid sequence of the EPO protein

<400> SEQUENCE: 35

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 36
<211> LENGTH: 1502
<212> TYPE: RNA
<213> ORGANISM: Artificial Sequence
<220> FEATURE:

-continued

<223> OTHER INFORMATION: Sequence of EPO circular RNA

<400> SEQUENCE: 36

```
aaaauccguu gaccuuaaac ggucguguggg guucaagucc cuccaccccc acgccggaaa      60
cgcaauagcc gaaaaacaaa aaacaaaaaa aacaaaaaaa aaaccaaaaa aacaaaacac     120
auuaaaacag ccugugggu gaucccaccc acagggccca uugggcgcua gcacucuggu     180
aucacgguac ccuugugcgc cuguuuuaug ucccuucccu caacuguaac uuagaaguaa     240
cgcacaccga ucaacaguca gcguggcaca ccagccaugu uuugaucaag cacuucuguu     300
accccggacc gaguaucaac agacugcuca cgcgguugaa ggagaaagug uucguuaucc     360
ggccaacuac uucgaaaaac cuaguaacac cauggaaguu gcagaguguu ucgcucagca     420
cuaccccagu guagaucagg ucgaugaguc accgcauccc ccacgggcga ccguggcggu     480
ggcugcguug gcggccugcc uauggggaa cccauaggac gcucuaauac agacauggug     540
cgaagagucc auugagcuag uugguagucc uccggccccu gaaugcggcu aauccuaacu     600
gcggagcaca caccuucaag ccagagggca gugugucgua acgggcaacu cugcagcgga     660
accgacuacu uugggugucc guguuucauu uuauucuuau acuggcugcu uaugguagaca     720
auugagagau uguuaccaua uagcuauugg auuggccauc cagugacuag cagagcuauu     780
auauaccucu uuguuggguu uauaccaccu aauuugaaag aaguuaaaac auuagaauuc     840
auuauuaaau ugaauacaau gggcgugcac gagugccccg ccuggcugug gcugcugcug     900
agccugcuga gccugccccu gggccugccc gugcugggcg cccccccccag gcugaucugc     960
gacagcaggg ugcuggagag guaccugcug gaggccaagg aggccgagaa caucaccacc    1020
ggcugcgccg agcacugcag ccugaacgag aacaucaccg ugcccgacac caaggugaac    1080
uucuacgccu ggaagaggau ggaggugggc cagcaggccg uggaggugug gcagggccug    1140
gcccugcuga gcgaggccgu gcugaggggc caggcccugc uggugaacag cagccagccc    1200
ugggagcccc ugcagcugca cguggacaag gccgugagcg gccugaggag ccugaccacc    1260
cugcugaggg cccugggcgc ccagaaggag gccaucagcc cccccgacgc cgccagcgcc    1320
gcccccuga ggaccaucac cgccgacacc uucaggaagc uguucagggu guacagcaac     1380
uuccugaggg gcaagcugaa gcuguacacc ggcgaggccu gcaggaccgg cgacagguga    1440
aaaaaaacaa aaaaacaaaa caaacggcua uuaugcguua ccggcgagac gcuacggacu    1500
ua                                                                    1502
```

<210> SEQ ID NO 37
<211> LENGTH: 648
<212> TYPE: DNA
<213> ORGANISM: Artificial Sequence
<220> FEATURE:
<223> OTHER INFORMATION: Sequence of the DNA encoding the light chain of the PD-1 monoclonal antibody

<400> SEQUENCE: 37

```
atggagatcg tgctgaccca gagccccgcc accctgagcc tgagccccgg cgagagggcc      60
accctgagct gcagggccag ccagagcgtg agcagctacc tggcctggta ccagcagaag     120
cccggccagg cccccaggct gctgatctac gacgccagca acagggccac cggcatcccc     180
gccaggttca gcggcagcgg cagcggcacc gacttcaccc tgaccatcag cagcctggag     240
cccgaggact tcgccgtgta ctactgccag cagagcagca actggcccag gaccttcggc     300
cagggcacca aggtggagat caagaggacc gtggccgccc ccagcgtgtt catcttcccc     360
```

cccagcgacg agcagctgaa gagcggcacc gccagcgtgg tgtgcctgct gaacaacttc 420
taccccaggg aggccaaggt gcagtggaag gtggacaacg ccctgcagag cggcaacagc 480
caggagagcg tgaccgagca ggacagcaag gacagcacct acagcctgag cagcaccctg 540
accctgagca aggccgacta cgagaagcac aaggtgtacg cctgcgaggt gacccaccag 600
ggcctgagca gccccgtgac caagagcttc aacaggggcg agtgctga 648

<210> SEQ ID NO 38
<211> LENGTH: 215
<212> TYPE: PRT
<213> ORGANISM: Artificial Sequence
<220> FEATURE:
<223> OTHER INFORMATION: Amino acid sequence of the light chain of the PD-1 monoclonal antibody

<400> SEQUENCE: 38

Met Glu Ile Val Leu Thr Gln Ser Pro Ala Thr Leu Ser Leu Ser Pro
1 5 10 15

Gly Glu Arg Ala Thr Leu Ser Cys Arg Ala Ser Gln Ser Val Ser Ser
20 25 30

Tyr Leu Ala Trp Tyr Gln Gln Lys Pro Gly Gln Ala Pro Arg Leu Leu
35 40 45

Ile Tyr Asp Ala Ser Asn Arg Ala Thr Gly Ile Pro Ala Arg Phe Ser
50 55 60

Gly Ser Gly Ser Gly Thr Asp Phe Thr Leu Thr Ile Ser Ser Leu Glu
65 70 75 80

Pro Glu Asp Phe Ala Val Tyr Tyr Cys Gln Gln Ser Ser Asn Trp Pro
85 90 95

Arg Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 39
<211> LENGTH: 1573
<212> TYPE: RNA
<213> ORGANISM: Artificial Sequence
<220> FEATURE:
<223> OTHER INFORMATION: Sequence of the light chain circular RNA of the PD-1 monoclonal antibody

<400> SEQUENCE: 39
aaaauccguu gaccuuaaac ggucgugugg guucaagucc cuccaccccc acgccggaaa 60
cgcaauagcc gaaaaaacaa aaacaaaaaa aacaaaaaaa caaaaaaaaa accaaaacac 120
auuaaaacag ccugugggu u gaucccaccc acagggccca cugggcgcua gcacucuggu 180
aucacgguac cuuugugcgc cuguuuuaua cuuccucccc caacugcaac uuagaaguaa 240
cacaaaccga ucaacaguca gcguggcaca ccagccacgu uuugaucaaa cacuucuguu 300
accccggacu gaguaucaau agacugcuca cgcgguugaa ggagaaaacg uucguuaucc 360
ggccaacuac uucgagaaac cuaguaacgc cauggaaguu guggaguguu ucgcucagca 420
cuaccccagu guagaucagg uugaugaguc accgcauucc ccacggguga ccguggcggu 480
ggcugcguug gcggccugcc cauggggaaa cccaugggac gcucuuauac agacauggug 540
cgaagagucu auugagcuag uugguagucc uccggccccu gaaugcggcu aaucccaacu 600
gcggagcaua cacucucaag ccagagggua gugugucgua augggcaacu cugcagcgga 660
accgacuacu uugggugucc guguuucauu uuauuccuau acuggcugcu uauggugaca 720
auugagagau uguuaccaua uagcuauugg auuggccauc cggugacuaa cagagcuauu 780
auauaucuuu uuguuggguu uauaccacuu agcuugaaag agguuaaaac ucuacauuac 840
auuuuaauac ugaacaccgc aaaauggaga ucgugcugac ccagagcccc gccacccuga 900
gccugagccc cggcgagagg gccacccuga gcugcagggc cagccagagc gugagcagcu 960
accuggccug guaccagcag aagcccggcc aggcccccag gcugcugauc uacgacgcca 1020
gcaacagggc caccggcauc cccgccaggu ucagcggcag cggcagcggc accgacuuca 1080
cccugaccau cagcagccug gagcccgagg acuucgccgu guacuacugc cagcagagca 1140
gcaacuggcc caggaccuuc ggccagggca ccaaggugga gaucaagagg accguggccg 1200
cccccagcgu guucaucuuc ccccccagcg acgagcagcu gaagagcggc accgccagcg 1260
uggugugccu gcugaacaac uucuacccca gggaggccaa ggugcagugg aagguggaca 1320
acgcccugca gagcggcaac agccaggaga gcgugaccga gcaggacagc aaggacagca 1380
ccuacagccu gagcagcacc cugacccuga gcaaggccga cuacgagaag cacaaggugu 1440
acgccugcga ggugacccac cagggccuga gcagccccgu gaccaagagc uucaacaggg 1500
gcgagugcug aaaaaaaaca aaaaaacaaa acaaacggcu auuaugcguu accggcgaga 1560
cgcuacggac uua 1573

<210> SEQ ID NO 40
<211> LENGTH: 1326
<212> TYPE: DNA
<213> ORGANISM: Artificial Sequence
<220> FEATURE:
<223> OTHER INFORMATION: Sequence of the DNA encoding the heavy chain of the PD-1 monoclonal antibody

<400> SEQUENCE: 40
atgcaggtgc agctggtgga gagcggcggc ggcgtggtgc agcccggcag gagcctgagg 60
ctggactgca aggccagcgg catcaccttc agcaacagcg gcatgcactg ggtgaggcag 120
gcccccggca agggcctgga gtgggtggcc gtgatctggt acgacggcag caagaggtac 180
tacgccgaca gcgtgaaggg caggttcacc atcagcaggg acaacagcaa gaacaccctg 240
ttcctgcaga tgaacagcct gagggccgag gacaccgccg tgtactactg cgccaccaac 300
gacgactact ggggccaggg caccctggtg accgtgagca gcgccagcac caagggcccc 360
agcgtgttcc ccctggcccc ctgcagcagg agcaccagcg agagcaccgc cgccctgggc 420
tgcctggtga aggactactt ccccgagccc gtgaccgtga gctggaacag cggcgccctg 480
accagcggcg tgcacacctt ccccgccgtg ctgcagagca gcggcctgta cagcctgagc 540
agcgtggtga ccgtgcccag cagcagcctg ggcaccaaga cctacacctg caacgtggac 600

-continued

```
cacaagccca gcaacaccaa ggtggacaag agggtggaga gcaagtacgg cccccctgc    660

ccccctgcc ccgcccccga gttcctgggc ggccccagcg tgttcctgtt cccccccaag    720

cccaaggaca ccctgatgat cagcaggacc cccgaggtga cctgcgtggt ggtggacgtg    780

agccaggagg accccgaggt gcagttcaac tggtacgtgg acggcgtgga ggtgcacaac    840

gccaagacca agcccaggga ggagcagttc aacagcacct acagggtggt gagcgtgctg    900

accgtgctgc accaggactg gctgaacggc aaggagtaca agtgcaaggt gagcaacaag    960

ggcctgccca gcagcatcga gaagaccatc agcaaggcca agggccagcc cagggagccc   1020

caggtgtaca ccctgccccc cagccaggag gagatgacca agaaccaggt gagcctgacc   1080

tgcctggtga agggcttcta ccccagcgac atcgccgtgg agtgggagag caacggccag   1140

cccgagaaca actacaagac cacccccccc gtgctggaca gcgacggcag cttcttcctg   1200

tacagcaggc tgaccgtgga caagagcagg tggcaggagg gcaacgtgtt cagctgcagc   1260

gtgatgcacg aggccctgca caaccactac acccagaaga gcctgagcct gagcctgggc   1320

aagtga                                                              1326


<210> SEQ ID NO 41
<211> LENGTH: 440
<212> TYPE: PRT
<213> ORGANISM: Artificial Sequence
<220> FEATURE:
<223> OTHER INFORMATION: Amino acid sequence of the heavy chain protein
      of the PD-1 monoclonal antibody

<400> SEQUENCE: 41

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220
```

```
Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 42
<211> LENGTH: 2251
<212> TYPE: RNA
<213> ORGANISM: Artificial Sequence
<220> FEATURE:
<223> OTHER INFORMATION: Sequence of the heavy chain circular RNA of the
      PD-1 monoclonal antibody

<400> SEQUENCE: 42

aaaauccguu gaccuuaaac ggucgugugg guucaagucc cuccaccccc acgccggaaa      60

cgcaauagcc gaaaaaacaa aaacaaaaaa aacaaaaaaa caaaaaaaaa accaaaacac     120

auuaaaacag ccugugguu gaucccaccc acagggccca cugggcgcua gcacucuggu     180

aucacgguac cuuugugcgc cuguuuuaua cuuccucccc caacugcaac uuagaaguaa     240

cacaaaccga ucaacaguca gcguggcaca ccagccacgu uuugaucaaa cacuucuguu     300

accccggacu gaguaucaau agacugcuca cgcgguugaa ggagaaaacg uucguuaucc     360

ggccaacuac uucgagaaac cuaguaacgc cauggaaguu guggaguguu ucgcucagca     420

cuaccccagu guagaucagg uugaugaguc accgcauucc ccacggguga ccguggcggu     480

ggcugcguug gcggccugcc cauggggaaa cccaugggac gcucuuauac agacauggug     540

cgaagagucu auugagcuag uugguagucc uccggccccu gaaugcggcu aaucccaacu     600

gcggagcaua cacucucaag ccagagggua gugugucgua augggcaacu cugcagcgga     660

accgacuacu uugggugucc guguuucauu uuauuccuau acuggcugcu uaugguggaca     720

auugagagau uguuaccaua uagcuauugg auuggccauc cggugacuaa cagagcuauu     780
```

auauaucuuu uuguuggguu uauaccacuu agcuugaaag agguuaaaac ucuacauuac 840
auuuuaauac ugaacaccgc aaaaugcagg ugcagcuggu ggagagcggc ggcggcgugg 900
ugcagcccgg caggagccug aggcuggacu gcaaggccag cggcaucacc uucagcaaca 960
gcggcaugca cugggugagg caggcccccg gcaagggccu ggagugggug gccgugaucu 1020
gguacgacgg cagcaagagg uacuacgccg acagcgugaa gggcagguuc accaucagca 1080
gggacaacag caagaacacc cuguuccugc agaugaacag ccugagggcc gaggacaccg 1140
ccguguacua cugcgccacc aacgacgacu acuggggcca gggcacccug gugaccguga 1200
gcagcgccag caccaagggc cccagcgugu ucccccuggc cccuugcagc aggagcacca 1260
gcgagagcac cgccgcccug ggcugccugg ugaaggacua cuuccccgag cccgugaccg 1320
ugagcuggaa cagcggcgcc cugaccagcg gcgugcacac cuuccccgcc gugcugcaga 1380
gcagcggccu guacagccug agcagcgugg ugaccgugcc cagcagcagc cugggcacca 1440
agaccuacac cugcaacgug gaccacaagc ccagcaacac caagguggac aagagggugg 1500
agagcaagua cggccccccc ugcccccccu gccccgcccc cgaguuccug ggcggcccca 1560
gcguguuccu guuccccccc aagcccaagg acacccugau gaucagcagg acccccgagg 1620
ugaccugcgu gguggugggac gugagccagg aggaccccga ggugcaguuc aacugguacg 1680
uggacggcgu ggaggugcac aacgccaaga ccaagcccag ggaggagcag uucaacagca 1740
ccuacagggu ggugagcgug cugaccgugc ugcaccagga cuggcugaac ggcaaggagu 1800
acaagugcaa ggugagcaac aagggccugc ccagcagcau cgagaagacc aucagcaagg 1860
ccaagggcca gcccagggag ccccaggugu acacccugcc ccccagccag gaggagauga 1920
ccaagaacca ggugagccug accugccugg ugaagggcuu cuaccccagc gacaucgccg 1980
uggaguggga gagcaacggc cagcccgaga acaacuacaa gaccaccccc cccgugcugg 2040
acagcgacgg cagcuucuuc cuguacagca ggcugaccgu ggacaagagc agguggcagg 2100
agggcaacgu guucagcugc agcgugaugc acgaggcccu gcacaaccac uacacccaga 2160
agagccugag ccugagccug ggcaagugaa aaaaaacaaa aaaacaaaac aaacggcuau 2220
uaugcguuac cggcgagacg cuacggacuu a 2251

<210> SEQ ID NO 43
<211> LENGTH: 489
<212> TYPE: DNA
<213> ORGANISM: Artificial Sequence
<220> FEATURE:
<223> OTHER INFORMATION: Sequence of IL-15 encoding DNA

<400> SEQUENCE: 43
atgaggatca gcaagcccca cctgaggagc atcagcatcc agtgctacct gtgcctgctg 60
ctgaacagcc acttcctgac cgaggccggc atccacgtgt tcatcctggg ctgcttcagc 120
gccggcctgc ccaagaccga ggccaactgg gtgaacgtga tcagcgacct gaagaagatc 180
gaggacctga tccagagcat gcacatcgac gccaccctgt acaccgagag cgacgtgcac 240
cccagctgca aggtgaccgc catgaagtgc ttcctgctgg agctgcaggt gatcagcctg 300
gagagcggcg acgccagcat ccacgacacc gtggagaacc tgatcatcct ggccaacaac 360
agcctgagca gcaacggcaa cgtgaccgag agcggctgca aggagtgcga ggagctggag 420
gagaagaaca tcaaggagtt cctgcagagc ttcgtgcaca tcgtgcagat gttcatcaac 480
accagctga 489

<210> SEQ ID NO 44
<211> LENGTH: 162
<212> TYPE: PRT
<213> ORGANISM: Artificial Sequence
<220> FEATURE:
<223> OTHER INFORMATION: Amino acid sequence of IL-15 protein

<400> SEQUENCE: 44

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```

<210> SEQ ID NO 45
<211> LENGTH: 1414
<212> TYPE: RNA
<213> ORGANISM: Artificial Sequence
<220> FEATURE:
<223> OTHER INFORMATION: Sequence of IL-15 circular RNA

<400> SEQUENCE: 45

```
aaaauccguu gaccuuaaac ggucguguggg guucaagucc cuccaccccc acgccggaaa      60

cgcaauagcc gaaaaaacaa aaacaaaaaa aacaaaaaaa caaaaaaaaa accaaaacac     120

auuaaaacag ccugugggguu gaucccaccc acagggccca cugggcgcua gcacucuggu     180

aucacgguac cuuugugcgc cuguuuuaua cuuccucccc caacugcaac uuagaaguaa     240

cacaaaccga ucaacaguca gcguggcaca ccagccacgu uuugaucaaa cacuucuguu     300

accccggacu gaguaucaau agacugcuca cgcgguugaa ggagaaaacg uucguuaucc     360

ggccaacuac uucgagaaac cuaguaacgc cauggaaguu guggaguguu ucgcucagca     420

cuaccccagu guagaucagg uugaugaguc accgcauucc ccacggguga ccguggcggu     480

ggcugcguug gcggccugcc caugggggaaa cccaugggac gcucuuauac agacauggug     540

cgaagagucu auugagcuag uugguagucc uccggccccu gaaugcggcu aaucccaacu     600

gcggagcaua cacucucaag ccagagggua gugugucgua augggcaacu cugcagcgga     660

accgacuacu uuggguguccc guguuucauu uuauuccuau acuggcugcu uauggugaca     720

auugagagau uguuaccaua uagcuauugg auuggccauc cggugacuaa cagagcuauu     780

auauaucuuu uuguuggguu uauaccacuu agcuugaaag agguuaaaac ucuacauuac     840
```

auuuuaauac ugaacaccgc aaaaugagga ucagcaagcc ccaccugagg agcaucagca 900
uccagugcua ccugugccug cugcugaaca gccacuuccu gaccgaggcc ggcauccacg 960
uguucauccu gggcugcuuc agcgccggcc ugcccaagac cgaggccaac ugggugaacg 1020
ugaucagcga ccugaagaag aucgaggacc ugauccagag caugcacauc gacgccaccc 1080
uguacaccga gagcgacgug caccccagcu gcaaggugac cgccaugaag ugcuuccugc 1140
uggagcugca ggugaucagc cuggagagcg gcgacgccag cauccacgac accguggaga 1200
accugaucau ccuggccaac aacagccuga gcagcaacgg caacgugacc gagagcggcu 1260
gcaaggagug cgaggagcug gaggagaaga acaucaagga guuccugcag agcuucgugc 1320
acaucgugca gauguucauc aacaccagcu gaaaaaaaac aaaaaaacaa aacaaacggc 1380
uauuaugcgu uaccggcgag acgcuacgga cuua 1414

<210> SEQ ID NO 46
<211> LENGTH: 1161
<212> TYPE: DNA
<213> ORGANISM: Artificial Sequence
<220> FEATURE:
<223> OTHER INFORMATION: Sequence of PAP encoding DNA

<400> SEQUENCE: 46
atgagggccg cccctctgct gctggctagg gccgctagcc tgagcctggg cttcctgttc 60
ctgctgttct tctggctgga taggagcgtg ctggccaagg agctgaagtt cgtgaccctg 120
gtgtttaggc acggcgatag gagccctatc gacaccttcc ctaccgaccc tatcaaggag 180
agcagctggc ctcaaggctt cggacagctg acacagctgg gcatggagca gcactacgag 240
ctgggcgagt acattaggaa gaggtatagg aagttcctga acgagagcta caagcacgag 300
caagtgtaca ttaggagcac cgacgtggat aggaccctga tgagcgccat gaccaacctg 360
gccgccctgt tccctcctga gggcgtgagc atctggaacc ctatcctgct gtggcagcct 420
atccctgtgc acaccgtgcc tctgagcgag gatcagctgc tgtacctgcc ttttaggaac 480
tgccctaggt tccaagagct ggagagcgag accctgaaga gcgaggagtt tcagaagagg 540
ctgcaccctt acaaggactt catcgccacc ctgggcaagc tctccggcct gcacggccaa 600
gacctgttcg gcatctggag caaggtgtac gaccctctgt actgcgagag cgtgcacaac 660
ttcaccctgc ctagctgggc caccgaggac accatgacca agctgaggga gctgagcgag 720
ctgagcctgc tgagcctgta cggcatccac aagcagaagg agaagtctag gctgcaaggc 780
ggcgtgctgg tgaacgagat cctgaaccac atgaagaggg ccacacagat ccctagctac 840
aagaagctga tcatgtacag cgcccacgac accaccgtca gcggcctgca gatggccctg 900
gacgtgtaca acggcctgct gcctccttac gctagctgcc acctgaccga gctgtacttc 960
gagaagggcg agtacttcgt ggagatgtac tataggaacg agacacagca cgagccttac 1020
cctctgatgc tgcctggctg cagccctagc tgccctctgg agaggttcgc cgagctggtg 1080
ggccctgtga tccctcaaga ctggagcacc gagtgcatga ccaccaacag ccaccaaggc 1140
accgaggaca gcaccgactg a 1161

<210> SEQ ID NO 47
<211> LENGTH: 386
<212> TYPE: PRT
<213> ORGANISM: Artificial Sequence
<220> FEATURE:
<223> OTHER INFORMATION: Amino acid sequence of the PAP protein

<400> SEQUENCE: 47

```
Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
    50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser
                85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
        115                 120                 125

Val Ser Ile Trp Asn Pro Ile Leu Leu Trp Gln Pro Ile Pro Val His
    130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
        195                 200                 205

Val Tyr Asp Pro Leu Tyr Cys Glu Ser Val His Asn Phe Thr Leu Pro
    210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
        275                 280                 285

His Asp Thr Thr Val Ser Gly Leu Gln Met Ala Leu Asp Val Tyr Asn
    290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
        355                 360                 365

Ser Thr Glu Cys Met Thr Thr Asn Ser His Gln Gly Thr Glu Asp Ser
    370                 375                 380

Thr Asp
385
```

<210> SEQ ID NO 48

<211> LENGTH: 2086
<212> TYPE: RNA
<213> ORGANISM: Artificial Sequence
<220> FEATURE:
<223> OTHER INFORMATION: Sequence of PAP circular RNA

<400> SEQUENCE: 48
aaaauccguu gaccuuaaac ggucgugugg guucaagucc cuccaccccc acgccggaaa 60
cgcaauagcc gaaaaaacaa aaacaaaaaa aacaaaaaaa caaaaaaaaa accaaaacac 120
auuaaaacag ccugugggu gaucccaccc acagggccca cugggcgcua gcacucuggu 180
aucacgguac cuuugugcgc cuguuuuaua cuuccucccc caacugcaac uuagaaguaa 240
cacaaaccga ucaacaguca gcguggcaca ccagccacgu uuugaucaaa cacuucuguu 300
accccggacu gaguaucaau agacugcuca cgcgguugaa ggagaaaacg uucguuaucc 360
ggccaacuac uucgagaaac cuaguaacgc cauggaaguu guggaguguu ucgcucagca 420
cuaccccagu guagaucagg uugaugaguc accgcauucc ccacgggugua ccguggcggu 480 ggcugcguug gcggccugcc cauggggaaa cccaugggac gcucuuauac agacauggug 540
cgaagagucu auugagcuag uugguagucc uccggccccu gaaugcggcu aaucccaacu 600
gcggagcaua cacucucaag ccagagggua gugugucgua augggcaacu cugcagcgga 660
accgacuacu uuggguguccc guguuucauu uuauuccuau acuggcugcu uauggugaca 720
auugagagau uguuaccaua uagcuauugg auuggccauc cggugacuaa cagagcuauu 780
auauaucuuu uuguuggguu uauaccacuu agcuugaaag agguuaaaac ucuacauuac 840
auuuuaauac ugaacaccgc aaaaugaggg ccgccccucu gcugcuggcu agggccgcua 900
gccugagccu gggcuuccug uuccugcugu ucuucuggcu ggauaggagc gugcuggcca 960
aggagcugaa guucgugacc cuggguguuua ggcacggcga uaggagcccu aucgacaccu 1020
ucccuaccga cccuaucaag gagagcagcu ggccucaagg cuucggacag cugacacagc 1080
ugggcaugga gcagcacuac gagcugggcg aguacauuag gaagagguau aggaaguucc 1140
ugaacgagag cuacaagcac gagcaagugu acauuaggag caccgacgug gauaggaccc 1200
ugaugagcgc caugaccaac cuggccgccc uguucccucc ugagggcgug agcaucugga 1260
acccuauccu gcuguggcag ccuaucccug ugcacaccgu gccucugagc gaggaucagc 1320
ugcuguaccu gccuuuuagg aacugcccua gguuccaaga gcuggagagc gagacccuga 1380
agagcgagga guuucagaag aggcugcacc cuuacaagga cuucaucgcc acccugggca 1440
agcucuccgg ccugcacggc caagaccugu ucggcaucug gagcaaggug uacgacccuc 1500
uguacugcga gagcgugcac aacuucaccc ugccuagcug ggccaccgag gacaccauga 1560
ccaagcugag ggagcugagc gagcugagcc ugcugagccu guacggcauc cacaagcaga 1620
aggagaaguc uaggcugcaa ggcggcgugc uggugaacga gauccugaac cacaugaaga 1680
gggccacaca gaucccuagc uacaagaagc ugaucaugua cagcgcccac gacaccaccg 1740
ucagcggccu gcagauggcc cuggacgugu acaacggccu gcugccuccu uacgcuagcu 1800
gccaccugac cgagcuguac uucgagaagg gcgaguacuu cguggagaug uacuauagga 1860
acgagacaca gcacgagccu uacccucuga ugcugccugg cugcagcccu agcugcccuc 1920
uggagagguu cgccgagcug gugggcccug ugaucccuca agacuggagc accgagugca 1980
ugaccaccaa cagccaccaa ggcaccgagg acagcaccga cugaaaaaaa acaaaaaaac 2040
aaaacaaacg gcuauuaugc guuaccggcg agacgcuacg gacuua 2086

<210> SEQ ID NO 49
<211> LENGTH: 1260
<212> TYPE: DNA
<213> ORGANISM: Artificial Sequence
<220> FEATURE:
<223> OTHER INFORMATION: equence of CD16 CAR encoding DNA

<400> SEQUENCE: 49
atgggcggcg gcgccggcga gaggctgttc accagcagct gcctggtggg cctggtgccc 60
ctgggcctga ggatcagcct ggtgacctgc cccctgcagt gcggcatcat gtggcagctg 120
ctgctgccca ccgccctgct gctgctcgtg agcgccggca tgaggaccga ggacctgccc 180
aaggccgtgg tgttcctgga gccccagtgg tacagggtgc tggagaagga cagcgtgacc 240
ctgaagtgcc agggcgccta cagccccgag gacaacagca cccagtggtt ccacaacgag 300
agcctgatca gcagccaggc cagcagctac ttcatcgacg ccgccacagt ggacgactct 360
ggagagtaca ggtgccagac aaacctgagc accctgtctg accccgtgca gcttgaagtg 420
catatcggct ggctgttgct gcaggcccct aggtgggtgt tcaaggagga ggaccctatt 480
cacctgaggt gtcacagctg gaagaacacc gccctgcaca aggtgaccta cctgcagaac 540
ggcaagggca ggaagtactt ccaccacaac agcgacttct acatccccaa ggccaccctg 600
aaggacagcg gcagctactt ctgcaggggc gtgttcggca gcaagaacgt gagcagcgag 660
accgtgaaca tcaccattac ccagggcctg gccgtgagca ccatcagcag cttcttccct 720
cccggctacc agatctacat ctgggccccc ttggccggca cctgcggcgt gctgctgctg 780
agcctggtga tcaccaagag gggcagaaag aagctgctgt acatcttcaa gcagcccttc 840
atgagacccg tgcagaccac ccaggaggag gacggctgca gctgccggtt ccccgaagag 900
gaggagggcg gctgcgagct gagagtgaag ttcagcagga gcgccgacgc ccccgcctac 960
cagcagggcc agaaccagct gtacaacgag ctgaacctgg gcaggagaga ggagtacgac 1020
gtgctggaca agagaagggg cagggacccc gagatgggcg gcaagcccag aaggaagaac 1080
ccccaggagg gcctgtacaa cgagctgcag aaggacaaga tggccgaggc ctacagcgag 1140
atcggcatga agggcgagag gaggaggggc aagggccacg acggcctgta ccagggcctg 1200
agcaccgcca ccaaggacac ctacgacgcc ctgcacatgc aggccctgcc ccctaggtga 1260

<210> SEQ ID NO 50
<211> LENGTH: 419
<212> TYPE: PRT
<213> ORGANISM: Artificial Sequence
<220> FEATURE:
<223> OTHER INFORMATION: Amino acid sequence of the CD16 CAR protein

<400> SEQUENCE: 50

Met Gly Gly Gly Ala Gly Glu Arg Leu Phe Thr Ser Ser Cys Leu Val
1 5 10 15

Gly Leu Val Pro Leu Gly Leu Arg Ile Ser Leu Val Thr Cys Pro Leu
20 25 30

Gln Cys Gly Ile Met Trp Gln Leu Leu Leu Pro Thr Ala Leu Leu Leu
35 40 45

Leu Val Ser Ala Gly Met Arg Thr Glu Asp Leu Pro Lys Ala Val Val
50 55 60

Phe Leu Glu Pro Gln Trp Tyr Arg Val Leu Glu Lys Asp Ser Val Thr
65 70 75 80

Leu Lys Cys Gln Gly Ala Tyr Ser Pro Glu Asp Asn Ser Thr Gln Trp
85 90 95

```
Phe His Asn Glu Ser Leu Ile Ser Ser Gln Ala Ser Ser Tyr Phe Ile
            100                 105                 110

Asp Ala Ala Thr Val Asp Asp Ser Gly Glu Tyr Arg Cys Gln Thr Asn
        115                 120                 125

Leu Ser Thr Leu Ser Asp Pro Val Gln Leu Glu Val His Ile Gly Trp
    130                 135                 140

Leu Leu Leu Gln Ala Pro Arg Trp Val Phe Lys Glu Glu Asp Pro Ile
145                 150                 155                 160

His Leu Arg Cys His Ser Trp Lys Asn Thr Ala Leu His Lys Val Thr
                165                 170                 175

Tyr Leu Gln Asn Gly Lys Gly Arg Lys Tyr Phe His His Asn Ser Asp
            180                 185                 190

Phe Tyr Ile Pro Lys Ala Thr Leu Lys Asp Ser Gly Ser Tyr Phe Cys
        195                 200                 205

Arg Gly Val Phe Gly Ser Lys Asn Val Ser Ser Glu Thr Val Asn Ile
    210                 215                 220

Thr Ile Thr Gln Gly Leu Ala Val Ser Thr Ile Ser Ser Phe Phe Pro
225                 230                 235                 240

Pro Gly Tyr Gln Ile Tyr Ile Trp Ala Pro Leu Ala Gly Thr Cys Gly
                245                 250                 255

Val Leu Leu Leu Ser Leu Val Ile Thr Lys Arg Gly Arg Lys Lys Leu
            260                 265                 270

Leu Tyr Ile Phe Lys Gln Pro Phe Met Arg Pro Val Gln Thr Thr Gln
        275                 280                 285

Glu Glu Asp Gly Cys Ser Cys Arg Phe Pro Glu Glu Glu Glu Gly Gly
    290                 295                 300

Cys Glu Leu Arg Val Lys Phe Ser Arg Ser Ala Asp Ala Pro Ala Tyr
305                 310                 315                 320

Gln Gln Gly Gln Asn Gln Leu Tyr Asn Glu Leu Asn Leu Gly Arg Arg
                325                 330                 335

Glu Glu Tyr Asp Val Leu Asp Lys Arg Arg Gly Arg Asp Pro Glu Met
            340                 345                 350

Gly Gly Lys Pro Arg Arg Lys Asn Pro Gln Glu Gly Leu Tyr Asn Glu
        355                 360                 365

Leu Gln Lys Asp Lys Met Ala Glu Ala Tyr Ser Glu Ile Gly Met Lys
    370                 375                 380

Gly Glu Arg Arg Arg Gly Lys Gly His Asp Gly Leu Tyr Gln Gly Leu
385                 390                 395                 400

Ser Thr Ala Thr Lys Asp Thr Tyr Asp Ala Leu His Met Gln Ala Leu
                405                 410                 415

Pro Pro Arg
```

<210> SEQ ID NO 51
<211> LENGTH: 2185
<212> TYPE: RNA
<213> ORGANISM: Artificial Sequence
<220> FEATURE:
<223> OTHER INFORMATION: Sequence of CD16 CAR circular RNA

<400> SEQUENCE: 51

```
aaaauccguu gaccuuaaac ggucguguagg guucaagucc cuccaccccc acgccggaaa      60

cgcaauagcc gaaaaaacaa aaacaaaaaa aacaaaaaaa caaaaaaaaa accaaaacac     120

auuaaaacag ccugugggguu gaucccaccc acagggccca cugggcgcua gcacucuggu     180

aucacgguac cuuugugcgc cuguuuuaua cuuccucccc caacugcaac uuagaaguaa     240
```

-continued

```
cacaaaccga ucaacaguca gcguggcaca ccagccacgu uuugaucaaa cacuucuguu    300

accccggacu gaguaucaau agacugcuca cgcgguugaa ggagaaaacg uucguuaucc    360

ggccaacuac uucgagaaac cuaguaacgc cauggaaguu guggaguguu ucgcucagca    420

cuaccccagu guagaucagg uugaugaguc accgcauucc ccacgggguga ccguggcggu    480

ggcugcguug gcggccugcc cauggggaaa cccaugggac gcucuuauac agacauggug    540

cgaagagucu auugagcuag uugguagucc uccggccccu gaaugcggcu aaucccaacu    600

gcggagcaua cacucucaag ccagagggua gugugucgua augggcaacu cugcagcgga    660

accgacuacu uugggugucc guguuucauu uuauuccuau acuggcugcu uauggugaca    720

auugagagau uguuaccaua uagcuauugg auuggccauc cggugacuaa cagagcuauu    780

auauaucuuu uuguuggguu uauaccacuu agcuugaaag agguuaaaac ucuacauuac    840

auuuuaauac ugaacaccgc aaaaugggcg gcggcgccgg cgagaggcug uucaccagca    900

gcugccuggu gggccuggug ccccugggcc ugaggaucag ccuggugacc ugccccccugc    960

agugcggcau cauguggcag cugcugcugc ccaccgcccu gcugcugcuc gugagcgccg   1020

gcaugaggac cgaggaccug cccaaggccg ugguguuccu ggagccccag ugguacaggg   1080

ugcuggagaa ggacagcgug acccugaagu gccagggcgc cuacagcccc gaggacaaca   1140

gcacccagug guuccacaac gagagccuga ucagcagcca ggccagcagc uacuucaucg   1200

acgccgccac aguggacgac ucuggagagu acaggugcca gacaaaccug agcacccugu   1260

cugaccccgu gcagcuugaa gugcauaucg gcuggcuguu gcugcaggcc ccuaggguggg   1320

uguucaagga ggaggacccu auucaccuga ggugucacag cuggaagaac accgcccugc   1380

acaaggugac cuaccugcag aacggcaagg gcaggaagua cuuccaccac aacagcgacu   1440

ucuacauccc caaggccacc cugaaggaca gcggcagcua cuucugcagg ggcguguucg   1500

gcagcaagaa cgugagcagc gagaccguga acaucaccau uacccagggc cuggccguga   1560

gcaccaucag cagcuucuuc ccucccggcu accagaucua caucugggcc cccuuggccg   1620

gcaccugcgg cgugcugcug cugagccugg ugaucaccaa gaggggcaga aagaagcugc   1680

uguacaucuu caagcagccc uucaugagac ccgugcagac cacccaggag gaggacggcu   1740

gcagcugccg guuccccgaa gaggaggagg gcggcugcga gcugagagug aaguucagca   1800

ggagcgccga cgcccccgcc uaccagcagg gccagaacca gcuguacaac gagcugaacc   1860

ugggcaggag agaggaguac gacgugcugg acaagagaag gggcagggac cccgagaugg   1920

gcggcaagcc cagaaggaag aacccccagg agggccugua caacgagcug cagaaggaca   1980

agauggccga ggccuacagc gagaucggca ugaagggcga gaggaggagg ggcaagggcc   2040

acgacggccu guaccagggc cugagcaccg ccaccaagga caccuacgac gcccugcaca   2100

ugcaggcccu gcccccuagg ugaaaaaaaa caaaaaaaca aaacaaacgg cuauuaugcg   2160

uuaccggcga gacgcuacgg acuua                                          2185
```

<210> SEQ ID NO 52
<211> LENGTH: 25
<212> TYPE: DNA
<213> ORGANISM: Artificial Sequence
<220> FEATURE:
<223> OTHER INFORMATION: Sequence of 3'spacer

<400> SEQUENCE: 52

```
aaaaaaacaa aaaaacaaaa caaac                                            25
```

-continued

```
<210> SEQ ID NO 53
<211> LENGTH: 22
<212> TYPE: DNA
<213> ORGANISM: Artificial Sequence
<220> FEATURE:
<223> OTHER INFORMATION: Sequence of 3'spacer

<400> SEQUENCE: 53

aaaaacaaaa aacaaaacaa ac                                              22
```

RECOMBINANT NUCLEIC ACID MOLECULE OF TRANSCRIPTIONAL CIRCULAR RNA AND ITS APPLICATION IN PROTEIN EXPRESSION

CROSS-REFERENCE TO RELATED APPLICATIONS

This application is a continuation of U.S. application Ser. No. 17/337,612, filed Jun. 3, 2021, which claims the benefit of priority to CN 202011408937.4, filed on Dec. 4, 2020, the contents of which are hereby incorporated by reference in their entirety.

FIELD OF THE INVENTION

The present disclosure belongs to the technical fields of molecular biology and bioengineering. Specifically, the present disclosure relates to a recombinant nucleic acid molecule of transcriptional circular RNA and its application in protein expression. More specifically, the present disclosure relates to a recombinant nucleic acid molecule of transcriptional circular RNA, a recombinant expression vector, pre-circularized RNA, circular RNA, recombinant host cells, pharmaceutical compositions, and methods for preparing proteins.

BACKGROUND OF THE INVENTION

Messenger Ribonucleic Acid (mRNA) is transcribed from DNA and provides the genetic information needed for the next step of protein translation. When the mRNA encoding antigen is injected into human body, it can synthesize the antigen in vivo, thereby inducing strong cellular and humoral immune responses, and exhibiting the characteristics of autoimmune adjuvants, which is an excellent vaccine method[1-3]. In addition, mRNA has many other advantages as a vaccine or production of therapeutic proteins. For example, compared with DNA vectors, mRNA is transiently expressed in cells, there is no risk of integration into the genome, and it is not dependent on the cell cycle, so it has higher security[4]; Compared with viral vectors, mRNA does not have the immune resistance brought by the vector itself, so protein expression is easier to achieve[5]; compared with recombinant proteins, viruses, etc., the mRNA production process is cell-free. The system only involves enzyme-catalyzed reactions in vitro, so the production process is simpler, more controllable and low-cost[6]. At present, mRNA has shown wide application potential as vaccines, production of therapeutic proteins and as a means of gene therapy.

At present, the mRNA used in both clinical or pre-clinical applications is mainly linear mRNA. The structure of linear mRNA includes 5' cap structure (5' Cap), 3' polyadenosine tail (PolyA tail), and 5' untranslational sequence (5' untranslational). region, 5' UTR), 3'untranslational region (3' UTR), and open reading frame (ORF), etc.[7]. The 5' cap structure is the basic feature of eukaryotic mRNA, which is obtained by adding N7-methylguanosine to the 5' end of the mRNA[8]. Studies have found that the 5' cap structure promotes mRNA translation by binding to the translation initiation complex eif4E, and can prevent mRNA degradation effectively and reduce mRNA immunogenicity. The main function of the 3'polyadenosine tail is to bind to PolyA binding protein (PolyA binding protein, PABP), which interacts with eiF4G and eiF4E to mediate the formation of a ring of mRNA, promote the translation process, and prevent mRNA degradation[9]. 5' and 3' untranslated sequences, such as beta-globin 5' and 3' untranslated sequences, can effectively prevent mRNA degradation and promote mRNA translation into protein.

Circular RNA (circular RNAs, circRNAs) is a common type of RNA in eukaryotes. Naturally occurring circRNAs are mainly produced through a molecular mechanism called “back splicing” in cells. It has been found that eukaryotic circRNAs have a variety of molecular cell regulatory functions[10]. For example, circular RNA can regulate the expression of target genes by binding microRNAs (miRNA); circular RNA can regulate gene expression by directly binding to target proteins. The currently confirmed circular RNAs mainly function as non-coding RNAs. However, there are also circular RNAs that can encode proteins in nature, which is circular mRNAs. Circular mRNA tends to have a longer half-life due to its circular nature, so it is speculated that circular mRNA may have better stability. Methods of forming circular RNA in vitro include chemical methods, protease catalysis and ribozyme catalysis, etc.[11].

The natural type I intron system can undergo cleavage and ligation reactions to form circular intron RNA. The conserved sequence of the specific splicing site located at the 5'end of exon E1 is broken by the nucleophilic attack of the free 3'hydroxyl of guanylic acid triphosphate, resulting in a naked 3'hydroxyl, and guanylic acid binds to on the broken 5'exon E1. Thereafter, the naked 3'hydroxyl at the 5'end of the intron attacked the conserved sequence between the 3'end of the intron and exon E2, and exon E2 was removed, and the intron undergoes a loop reaction in order to obtain the circular intron RNA[12-13]. A modified ribozyme-catalyzed method from *Anabaena* tRNA introns has been reported to be applied to the formation of circular RNA in vitro[14], called the “inverted type I intron-exon self-cleavage system” (Group I permuted intron-exon self-splicing system, PIE system). This method can excise introns to form circular RNA containing exons. Therefore, this method has the potential to form expressible circular mRNA. The basic design principle of the PIE system is to connect exon E1 and E2 sequences end to end through molecular cloning to form a continuous circular plasmid. The intron is cut and broken by restriction endonuclease to obtain a linear plasmid. Then inverted T7 promoter upstream of 3'intron was used for in vitro transcription to obtain pre-circularized RNA containing 3'intron-E2-E1-5' intron structure. Similar to the natural type I intron system, the specific splicing site conservative sequence of exon E1 is broken by the nucleophilic attack of the free guanylic acid 3'hydroxyl group, and exon E1 produces a naked 3' Hydroxyl, and guanylic acid binds to the broken 5'intron. After that, the naked 3'hydroxyl of exon E1 attacked the conserved sequence between 3'intron and exon E2, removing the 3'intron, and exon E2 and E1 formed a loop reaction to get circular E1-E2 RNA.

According to prior art reports[15], the PIE system can be used to construct circular RNAs for eukaryotic protein expression. The study found that placing EMCV (Encephalomyocarditis Virus), CVB3 (Coxsackievirus B3) and other IRES (Internal ribosome entry site) sequences and coding gene sequences between E1 and E2 of the PIE system of *Anabaena* tRNA, the circular mRNA formed can be Eukaryotic cells such as 293 cells realize protein expression. In addition, in order to realize the in vitro looping of mRNA successfully, the study modified the PIE system by adding homology arm sequences and between the IRES and exon E2. The coding region and spacer sequence (Spacer) was added between the exons E1. First of all, the study referred to the PIE system discovered by M. Puttaraju and Michael D. Been, etc., and used the same *Anabaena* tRNA PIE system to construct circular mRNA. After inserting the EMCV or CVB3 IRES sequence and the coding gene Glue (*Gaussia* luciferase) between E1 and E2 of the PIE system, set homology arm sequences at the 5' and 3'ends of the RNA, respectively, between IRES and exon E2, And a spacer sequence is added between the coding region and exon E1, which can form circular mRNA to the greatest extent. After obtaining pre-circularized mRNA in the in vitro transcription reaction, circular mRNA is obtained through the auto-catalytic reaction of the PIE system under the action of heating and guanylate triphosphate. The circular mRNA finally contains exon E1 and E2 sequences, spacer sequence, IRES and coding gene sequence. Studies have found that the PIE system with homology arms and spacer sequences has better mRNA looping characteristics and can enhance protein expression. The study found that CVB3 IRES has a high ability to mediate mRNA translation by screening different IRES sequences, and therefore can achieve relatively high protein expression.

At present, although linear mRNA can achieve mRNA-mediated protein expression, its expression duration is short, and the amount of protein expression is insufficient. Therefore, it is necessary to develop new mRNA technology with the ability to express protein persistently. Although the circular mRNA structure disclosed in the prior art realizes the translation of the target protein by the circular RNA, and to a certain extent increases the protein expression of the target protein by the circular RNA translation. However, in order to meet the needs of industrial production of protein expression in vitro, it is still necessary to develop circular mRNA with higher protein expression and better protein expression durability.

CITATION

[1] Pardi, N. et al. (2018) Nucleoside-modified mRNA vaccines induce potent T follicular helper and germinal center B cell responses. J. Exp. Med. 215, 1571-1588.

[2] Liang, F. et al. (2017) Efficient targeting and activation of antigen-presenting cells in vivo after modified mRNA vaccine administration in rhesus macaques. Mol. Ther. 25, 2635-2647.

[3] Pardi, N. et al. (2017) Zika virus protection by a single low-dose nucleoside-modified mRNA vaccination. Nature 543, 248-251.

[4] Ugur Sahin, Katalin Karikó & Özlem Türeci, mRNA-based therapeutics—developing a new class of drugs. Nature Reviews Drug Discovery volume 13, pages 759-780(2014).

[5] Jamie L. Shirley, Ype P. de Jong, CoxTerhorst, Roland W. Herzog, Immune Responses to Viral Gene Therapy Vectors. Molecular Therapy, Volume 28, Issue 3, 4 Mar. 2020, Pages 709-722.

[6] Kis, Z. et al. (2018) Emerging technologies for low-cost, rapid vaccine manufacture. Biotechnol. J. 14, e1800376.

[7] mRNA vaccines—a new era in vaccinology. Nat. Rev. Drug Discov. 17, 261-279.

[8] Ramanathan, A. et al. (2016) mRNA capping: biological functions and applications. Nucleic Acids Res. 44, 7511-7526.

[9] Lima, S. A. et al. (2017) Short poly(A) tails are a conserved feature of highly expressed genes. Nat. Struct. Mol. Biol. 24, 1057-1063.

[10] Barrett, S. P. & Salzman, J. Circular RNAs: analysis, expression and potential functions. Development 143, 1838-1847 (2016).

[11] Sabine Muller and Bettina Appel, In vitro circularization of RNA, RNA BIOLOGY 2017, VOL. 14, NO. 8, 1018-1027.

[12] Cech, T. R. and Bass, B. L. (1986) Annu. Rev. Biochem. 55, 599-629.

[13] Cech, T. R. (1990) Annu. Rev. Biochem. 59, 543-568.

[14] M. Puttaraju, Michael D. Been, Nucleic Acids Research, Vol. 20, No. 20 5357-5364.

[15] US2020/0080106 A1.

DETAIL OF INVENTION

The Problem to be Solved by the Invention

In view of the technical problems existing in the prior art, for example, there is still a need to develop an improved protein expression level, high stability, and good expression durability, which is suitable for protein expression in vitro or in vivo. Therefore, the present invention provides a recombinant nucleic acid molecule whose circular RNA formed by transcription contains specific IRES elements, which can express target polypeptides in eukaryotic cells continuously and efficiently, and is suitable for preparing mRNA infectious disease vaccines and therapeutic mRNA Tumor vaccines, dendritic cell (DC) tumor vaccines based on mRNA, or for mRNA-based gene therapy (Gene therapy), mRNA-based chimeric antigen receptor T-cell therapy (Chimeric antigen receptor T-cell) therapy, Car-T), protein supplement therapy and other fields.

Solution to the Problem (1) A recombinant nucleic acid molecule, the recombinant nucleic acid molecule comprising an IRES element; wherein the IRES element comprises any one of the following (i)-(iv):

(i) A nucleotide sequence comprising one or more sequences in the group consisting of any one of SEQ ID NO: 8-11;

(ii) A nucleotide sequence comprising the reverse complement of the sequence shown in any one of SEQ ID NO: 8-11;

(iii) Under high stringency hybridization conditions or very high stringency hybridization conditions, the reverse complement of the sequence that can hybridize to the nucleotide sequence shown in (i) or (ii);

(iv) A sequence having at least 90%, optionally at least 95%, preferably at least 97%, more preferably at least 98%, and most preferably at least 99% sequence identity with the nucleotide sequence shown in (i) or (ii).

(2) The recombinant nucleic acid molecule according to (1), wherein the recombinant nucleic acid molecule further comprises a coding region encoding a target polypeptide, and the IRES element can increase the expression level of the target polypeptide; preferably, the IRES element can Increase the expression level of the target polypeptide in eukaryotic cells.

(3) The recombinant nucleic acid molecule according to (1) or (2), wherein the IRES element is selected from any one of the following (q1)-(q7):

($q_1$) A nucleotide sequence comprising the sequence shown in SEQ ID NO: 8;

($q_2$) A nucleotide sequence comprising the sequence shown in SEQ ID NO: 9;

($q_3$) A nucleotide sequence comprising the sequence shown in SEQ ID NO: 10;

($q_4$) A nucleotide sequence comprising the sequence shown in SEQ ID NO: 11;

($q_5$) A nucleotide sequence comprising the sequence shown in SEQ ID NO: 12;

($q_6$) A nucleotide sequence comprising the sequence shown in SEQ ID NO: 13;

($q_7$) A nucleotide sequence comprising the sequence shown in SEQ ID NO: 14.

(4) The recombinant nucleic acid molecule according to any one of (1) to (3), wherein the recombinant nucleic acid molecule further comprises a 5'homology arm located upstream of the IRES element, and a 5'homology arm located downstream of the coding region and connected to the The 3'homology arm complementary to the 5'homology arm;

Preferably, the 5'homology arm comprises the sequence shown in any one of (a1)-(a2) below:

($a_1$) The nucleotide sequence shown in any one of SEQ ID NO: 2-3;

($a_2$) A sequence having at least 90%, optionally at least 95%, preferably at least 97%, more preferably at least 98%, and most preferably at least 99% sequence identity to the nucleotide sequence shown in (a1);

The 3'homology arm includes the sequence shown in any one of (b1)-(b2) below:

($b_1$) The nucleotide sequence shown in any one of SEQ ID NO: 17-18;

($b_2$) A sequence having at least 90%, optionally at least 95%, preferably at least 97%, more preferably at least 98%, and most preferably at least 99% sequence identity with the nucleotide sequence shown in (b1).

(5) The recombinant nucleic acid molecule according to any one of (1) to (4), wherein the recombinant nucleic acid molecule further comprises a 5'spacer located between the 5'homology arm and the IRES element, and the 3'spacer between the coding region and the 3'homology arm;

Preferably, the 5'spacer comprises the sequence shown in any one of (c1)-(c2) below:

($c_1$) The nucleotide sequence shown in any one of SEQ ID NO: 6-7;

($c_2$) A sequence having at least 90%, optionally at least 95%, preferably at least 97%, more preferably at least 98%, and most preferably at least 99% sequence identity with the nucleotide sequence shown in (c1);

The 3'spacer includes the sequence shown in any of the following (o1)-(02):

($o_1$) The nucleotide sequence shown in any one of SEQ ID NO: 52-53;

($o_2$) A sequence having at least 90%, optionally at least 95%, preferably at least 97%, more preferably at least 98%, and most preferably at least 99% sequence identity to the nucleotide sequence shown in (o1).

(6) The recombinant nucleic acid molecule according to any one of (1) to (5), wherein the recombinant nucleic acid molecule further comprises a 3'intron and second exons located between the 5'homology arm and the IRES element, and the first exon and 5'intron located between the coding region and the 3'homology arm;

Preferably, the 3'intron is located upstream of the second exon, and the 5'spacer is included between the second exon and the IRES element; the first exon is located upstream of the 5'intron, and the 3'spacer is included between the first exon and the coding region.

(7) The recombinant nucleic acid molecule according to (6), wherein the 3'intron comprises the sequence shown in any one of (d1)-(d2):

($d_1$) The nucleotide sequence shown in SEQ ID NO: 4;

($d_2$) A sequence having at least 90%, optionally at least 95%, preferably at least 97%, more preferably at least 98%, and most preferably at least 99% sequence identity to the nucleotide sequence shown in (d1);

The second exon includes the sequence shown in any of the following (e1)-(e2):

($e_1$) The nucleotide sequence shown in SEQ ID NO: 5;

($e_2$) A sequence having at least 90%, optionally at least 95%, preferably at least 97%, more preferably at least 98%, and most preferably at least 99% sequence identity to the nucleotide sequence shown in (e 1);

The first exon includes the sequence shown in any one of (f1)-(f2):

($f_1$) The nucleotide sequence shown in SEQ ID NO: 15;

($f_2$) A sequence having at least 90%, optionally at least 95%, preferably at least 97%, more preferably at least 98%, and most preferably at least 99% sequence identity to the nucleotide sequence shown in (f1);

The 5'intron includes the sequence shown in any one of (g1)-(g2):

($g_1$) The nucleotide sequence shown in SEQ ID NO: 16;

($g_2$) A sequence having at least 90%, optionally at least 95%, preferably at least 97%, more preferably at least 98%, and most preferably at least 99% sequence identity to the nucleotide sequence shown in (g1).

(8) The recombinant nucleic acid molecule according to any one of (1) to (7), wherein the recombinant nucleic acid molecule further comprises a regulatory sequence, and the regulatory sequence is used to direct the recombinant nucleic acid molecule to transcribe the circular RNA.

(9) A recombinant expression vector, wherein the recombinant expression vector comprises the recombinant nucleic acid molecule according to any one of (1) to (8).

(10) A pre-circularized RNA formed by transcribing the recombinant nucleic acid molecule according to any one of (1) to (8) or the recombinant expression vector according to (9);

Preferably, the pre-circularized RNA includes 5'homology arm, 3'intron, second exon, 5'spacer, IRES element, coding region, 3'spacer, first exon, 5"Intron and 3'homology arm.

(11) A circular RNA, which is formed by the recombinant nucleic acid molecule according to (1)-(8) or the post-transcription circularization of the recombinant expression vector according to (9); or, it is formed by the thread according to (10) Circular RNA formation;

Optionally, the circular RNA comprises a second exon, a 5'spacer, an IRES element, a coding region, a 3'spacer and a first exon that are sequentially connected.

(12) The circular RNA according to (11), wherein the circular RNA expresses the target polypeptide.

(13) The circular RNA according to (12), wherein the target polypeptide is the receptor binding domain (RBD) of the S protein of the novel coronavirus; Preferably, the RBD protein is selected from any one of the following (h1)-(h4):

($h_1$) A polypeptide comprising the amino acid sequence shown in SEQ ID NO: 32 and having RBD protein activity;

($h_2$) The amino acid sequence shown in SEQ ID NO: 32 has been substituted, repeated, deleted or added one or more amino acids, and has RBD protein activity polypeptide;

($h_3$) A polypeptide encoded by a polynucleotide encoding the amino acid sequence shown in (h1) or (h2);

($h_4$) Encoded by a sequence having at least 90%, optionally at least 95%, preferably at least 97%, more preferably at least 98%, and most preferably at least 99% sequence identity with the nucleotide sequence shown in SEQ ID NO: 31, Peptides with RBD protein activity.

(14) The circular RNA according to (12) or (13), wherein the circular RNA contains at least 90%, optionally at least 95%, preferably at least 97% of the nucleotide sequence shown in SEQ ID NO: 33%, more preferably at least 98%, most preferably at least 99% sequence identity.

(15) The circular RNA according to (12), wherein the target polypeptide is selected from the group consisting of programmed cell death receptor 1 (PD-1), programmed cell death ligand-1 (programmed cell death ligand-1, PD-L1) or Cytotoxic T-Lymphocyte Associated Protein-4 (CTLA-4) monoclonal antibody;

Preferably, the PD-1 monoclonal antibody comprises any one of the following (j1)-(j6):
- ($j_1$) Light chain comprising the amino acid sequence shown in SEQ ID NO: 38;
- ($j_2$) The heavy chain of the amino acid sequence shown in SEQ ID NO: 41;
- ($j_3$) Polypeptide containing light chain protein activity after substitution, repetition, deletion or addition of one or more amino acids with the amino acid sequence shown in SEQ ID NO: 38;
- ($j_4$) A polypeptide that contains one or more amino acids that have been substituted, repeated, deleted or added to the amino acid sequence shown in SEQ ID NO: 41 and has heavy chain protein activity;
- ($j_5$) A polypeptide encoded by a polynucleotide encoding the amino acid sequence shown in any one of (j1)-(j4);
- ($j_6$) Encoded by a sequence having at least 90%, optionally at least 95%, preferably at least 97%, more preferably at least 98%, and most preferably at least 99% sequence identity with the nucleotide sequence shown in SEQ ID NO: 37. And a polypeptide having light chain protein activity; or, having at least 90%, optionally at least 95%, preferably at least 97%, more preferably at least 98%, most preferably at least 90% of the nucleotide sequence shown in SEQ ID NO: 40. A polypeptide encoded by a sequence with 99% sequence identity and having heavy chain protein activity.

(16) The circular RNA according to (12) or (15), wherein the circular RNA comprises at least 90%, optionally at least 95%, preferably at least 95% of the nucleotide sequence shown in SEQ ID NO: 39 or 42A. Have at least 97%, more preferably at least 98%, and most preferably at least 99% sequence identity.

(17) The circular RNA according to (12), wherein the target polypeptide is a chimeric antigen receptor; optionally, the target polypeptide is a CD16 protein of a chimeric antigen receptor, and the CD16 protein is selected from the following (Any one of k1)-(k4):
- (K 1) A polypeptide comprising the amino acid sequence shown in SEQ ID NO: 50 and having CD16 protein activity;
- (K 2) The amino acid sequence shown in SEQ ID NO: 50 has undergone substitution, repetition, deletion or addition of one or more amino acids, and a polypeptide with CD16 protein activity;
- (K 3) A polypeptide encoded by a polynucleotide encoding the amino acid sequence shown in (k 1) or (k 2);
- (K 4) The nucleotide sequence shown in SEQ ID NO: 49 has at least 90%, optionally at least 95%, preferably at least 97%, more preferably at least 98%, and most preferably at least 99% sequence identity A polypeptide that is encoded by the sequence and has CD16 protein activity.

(18) The circular RNA according to (12) or (17), wherein the circular RNA contains at least 90%, optionally at least 95%, preferably at least 97% of the nucleotide sequence shown in SEQ ID NO: 51%, more preferably at least 98%, most preferably at least 99% sequence identity.

(19) The circular RNA according to (12), wherein the target polypeptide is a recombinant humanized protein, optionally, the recombinant humanized protein is a recombinant human erythropoietin (EPO) protein, so The EPO protein is selected from any of the following (l1)-(l4):
- ($l_1$) A polypeptide comprising an amino acid sequence as shown in SEQ ID NO: 35 and having EPO protein activity;
- ($l_2$) The amino acid sequence shown in SEQ ID NO: 35 has been substituted, repeated, deleted or added with one or more amino acids, and has EPO protein activity;
- ($l_3$) A polypeptide encoded by a polynucleotide encoding the amino acid sequence shown in (11) or (12);
- ($l_4$) Encoded by a sequence having at least 90%, optionally at least 95%, preferably at least 97%, more preferably at least 98%, and most preferably at least 99% sequence identity to the nucleotide sequence shown in SEQ ID NO: 34, And a polypeptide with EPO protein activity.

(20) The circular RNA according to (12) or (19), wherein the circular RNA contains at least 90%, optionally at least 95%, preferably at least 97% of the nucleotide sequence shown in SEQ ID NO: 36%, more preferably at least 98%, most preferably at least 99% sequence identity.

(21) The circular RNA according to (12), wherein the target polypeptide is a cytokine; preferably, the cytokine is an IL-15 protein, and the IL-15 protein is selected from the following (m1)-(m4) Any one of:
- (M1) A polypeptide comprising the amino acid sequence shown in SEQ ID NO: 44 and having IL-15 protein activity;
- (M2) The amino acid sequence shown in SEQ ID NO: 44 has been substituted, repeated, deleted or added with one or more amino acids, and has IL-15 protein activity;
- (M3) A polypeptide encoded by a polynucleotide encoding the amino acid sequence shown in (m1) or (m2);
- (M4) A sequence having at least 90%, optionally at least 95%, preferably at least 97%, more preferably at least 98%, and most preferably at least 99% sequence identity with the nucleotide sequence shown in SEQ ID NO: 43 A polypeptide that is encoded and has IL-15 protein activity.

(22) The circular RNA according to (12) or (21), wherein the circular RNA contains at least 90%, optionally at least 95%, preferably at least 97% of the nucleotide sequence shown in SEQ ID NO: 45%, more preferably at least 98%, most preferably at least 99% sequence identity.

(23) The circular RNA according to (12), wherein the target polypeptide is a tumor-associated antigen or a tumor-specific antigen, optionally, the tumor-specific antigen is a PAP protein, and the PAP protein is selected from the following (n1 Any one of)-(n4):
- (N1) A polypeptide comprising the amino acid sequence shown in SEQ ID NO: 47 and having PAP protein activity;
- (N2) The amino acid sequence shown in SEQ ID NO: 47 has been substituted, repeated, deleted or added one or more amino acids, and has PAP protein activity;
- (N3) A polypeptide encoded by a polynucleotide encoding the amino acid sequence shown in (n1) or (n2);
- (N4) A sequence having at least 90%, optionally at least 95%, preferably at least 97%, more preferably at least 98%, and most preferably at least 99% sequence identity with the nucleotide sequence shown in SEQ ID NO: 46 A polypeptide that is encoded and has PAP protein activity.

(24) The circular RNA according to (12) or (23), wherein the circular RNA contains at least 90%, optionally at least 95%, preferably at least 97% of the nucleotide sequence shown in SEQ ID NO: 48%, more preferably at least 98%, most preferably at least 99% sequence identity.

(25) A recombinant host cell, wherein the recombinant host cell comprises the recombinant nucleic acid molecule according to any one of (1) to (8), the recombinant expression vector according to (9), and the recombinant expression vector according to (10) Pre-circularized RNA or the circular RNA according to any one of (11) to (24).

(26) A recombinant nucleic acid molecule according to any one of (1) to (8), the recombinant expression vector according to (9), the pre-circularized RNA according to (10), and according to (11) to (24) The use of the circular RNA according to any one of or the recombinant host cell according to (25) in the production of protein.

(27) A pharmaceutical composition, which comprises any one of the following (i)-(ii):

(i) The recombinant nucleic acid molecule described herein, the recombinant expression vector described herein, the pre-circularized RNA described herein, the recombinant nucleic acid molecule described herein, or the recombinant host cell described herein; or (ii) The recombinant nucleic acid molecule described herein, the recombinant expression vector described herein, the pre-circularized RNA described herein, the recombinant nucleic acid molecule described herein, or a target polypeptide expressed by the recombinant host cell described herein.

(28) A method for preparing a protein, which comprises using the recombinant nucleic acid molecule according to any one of (1) to (8), the recombinant expression vector according to (9), and the pre-circularized RNA according to (10), The circular RNA according to any one of (11) to (24), or the step of expressing the target protein in the recombinant host cell according to (25).

(29) A method for preventing or treating diseases, which comprises the steps of administering any one of (i) to (ii) to a subject:

(i) The recombinant nucleic acid molecule described herein, the recombinant expression vector described herein, the pre-circularized RNA described herein, the recombinant nucleic acid molecule described herein, or the recombinant host cell described herein; or (ii) The recombinant nucleic acid molecule described herein, the recombinant expression vector described herein, the pre-circularized RNA described herein, the recombinant nucleic acid molecule described herein, or a target polypeptide expressed by the recombinant host cell described herein.

Effect of Invention

In some embodiments, the recombinant nucleic acid molecule of the present disclosure is transcribed to form a circular RNA containing a specific IRES element. The IRES element can increase the protein expression level of the circular RNA in eukaryotic cells and achieve efficient and persistent protein expression, And the expression efficiency is higher than linear mRNA molecules or other circular RNAs, which can meet the needs of industrialized protein expression.

In some embodiments, the recombinant nucleic acid molecule of the present disclosure further comprises 5'homology arms, 3'homology arms, 5'spacers, and 3'spacer sequences with specific sequences to make the circular RNA molecule loop. The efficiency and the level of expressed protein are further improved.

In some embodiments, the circular RNA provided by the present disclosure can increase the expression level of the target polypeptide in eukaryotic cells, and achieve high efficiency and durability for antigens, antibodies, antigen binding receptors, ligands, fusion proteins, or recombinant proteins. Sexual expression, suitable for preparing therapeutic vaccines, antibodies or chimeric antigen receptors, T cell receptors, pharmaceutical recombinant proteins, etc.

DESCRIPTION OF THE DRAWINGS

In FIG. 1: 1. RNA ladder; 2. CVB3-EGFP pre-circularized mRNA; 3. CVB3-EGFP circularized mRNA; 4. EV29-EGFP pre-circularized mRNA 5. EV29-EGFP circularized mRNA; 6. EV29+CVB3v EGFP linearized mRNA; 7. EV29+CVB3v EGFP circularized mRNA; 8. EV33-EGFP linearized mRNA; 9. EV33-EGFP circularized mRNA; 10. EV33+CVB3v EGFP pre-circularized mRNA; 11. EV33+CVB3v EGFP circularized mRNA;

In FIG. 7: 1. RNA ladder; 2. CVB3-EGFP pre-circularized mRNA; 3. CVB3-EGFP circularized mRNA; 4. EV29-EGFP H1S1 pre-circularized mRNA; 5. EV29-EGFP H1S1 circularized mRNA; 6. EV29-EGFP H2S2 pre-circularized mRNA; 7. EV29-EGFP H2S2 circularized mRNA;

STATEMENT REGARDING SEQUENCE LISTING

Figure 1:
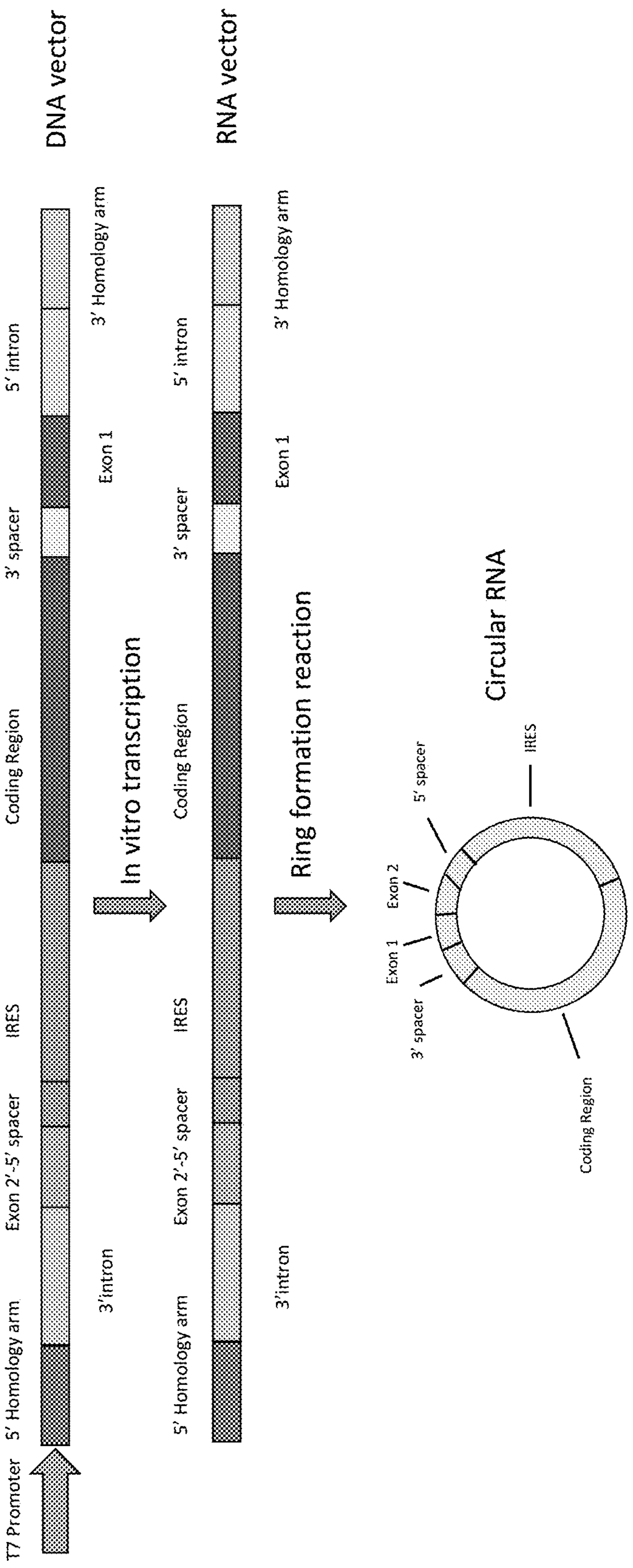
FIG. 1 shows a schematic diagram of the process of obtaining circular RNA with a recombinant expression vector (DNA vector) containing a recombinant nucleic acid molecule.

The Sequence Listing associated with this application is provided in text form in lieu of a paper copy, and is hereby incorporated by reference into the specification. The name of the text file containing the Sequence Listing is 52322-0002002.txt. The text file is 79.1 KB, and was created Sep. 27, 2021, and submitted electronically via EFS-Web with this application.

Detailed Ways

When used in conjunction with the term "comprising" in the claims and/or specification, the words "a" or "an" can mean "a", but can also mean "one or more", "at least One" and "one or more than one".

As used in the claims and specification, the words "include", "have", "include" or "contain" mean inclusive or open-ended, and do not exclude additional, unquoted elements or methods step.

Throughout the application documents, the term "about" means: a value includes the standard deviation of the error of the device or method used to determine the value.

Although the disclosed content supports the definition of the term "or" only as an alternative and "and/or", the term "or" in the claims means only alternatives or mutual exclusion between alternatives unless it is clearly stated "and/or".

As used in the present disclosure, the terms "polypeptide", "peptide" and "protein" are used interchangeably herein and are polymers of amino acids of any length. The polymer can be linear or branched, it can contain modified amino acids, and it can be interrupted by non-amino acids. The term also includes amino acid polymers that have been modified (for example, disulfide bond formation, glycosylation, lipidation, acetylation, phosphorylation, or any other manipulation, such as conjugation with labeling components).

As used in the present disclosure, the term "circular RNA" is a closed circular RNA molecule, mainly composed of exons, IRES elements, protein coding regions and spacers. In some preferred embodiments, the circular RNA has the following structure: "second exon E2-spacer-IRES element-coding region-spacer-first exon E1". The circular RNA used in the present disclosure has protein translation activity and can also be referred to as "circular mRNA".

As used in the present disclosure, the term "pre-circularized RNA" refers to an RNA precursor capable of circularization to form circular RNA, which is generally formed by transcription of a linear DNA molecule.

As used in the present disclosure, the term "linear RNA" refers to a 5'cap structure (5'Cap), a 3'polyadenosine tail (PolyA tail), and a 5'untranslational region (5'untranslational region, 5' UTR), 3'untranslational region (3'UTR), and open reading frame (ORF) and other structures with translational function.

As used in the present disclosure, the term "IRES" (Internal ribosome entry site, IRES) is also called internal ribosome entry site. "Internal ribosome entry site" (IRES) is a translation control sequence, usually located at the gene of interest. 5'end, and enables translation of RNA in a cap-independent manner. The transcribed IRES can directly bind to the ribosomal subunit so that the mRNA start codon is properly oriented in the ribosome for translation. The IRES sequence is usually located in the 5'UTR of the mRNA (just upstream of the start codon). IRES functionally replaces the need for various protein factors that interact with eukaryotic translation mechanisms. In some preferred embodiments, the IRES element of the present disclosure is selected from EV24 IRES, EV29 IRES, EV33 IRES, CVB3 IRES, or a chimera sequence of CVB3v IRES and any one of EV24 IRES, EV29 IRES, and EV33 IRES. "CVB3v" in the present disclosure refers to the v domain of CVB3 IRES. The chimera sequence in this disclosure includes: the EV24+CVB3v chimera obtained by replacing the v domain of EV24 IRES with the v domain of CVB3 IRES, and the v domain of CVB3 IRES. The EV29+CVB3v chimera obtained by replacing the v-domain of EV29 IRES with the v-domain of CVB3 IRES, and the EV33+CVB3v chimera obtained by replacing the v-domain of EV33 IRES with the v-domain of CVB3 IRES.

As used in the present disclosure, the term "coding region" refers to a gene sequence capable of transcribing messenger RNA and finally translating it into a target polypeptide or protein.

As used in this disclosure, the term "upstream" or "downstream" refers to upstream and downstream along the protein translation direction of the coding region.

In some embodiments, the coding region of the present disclosure encodes a target polypeptide selected from one or more of antigens, antibodies, antigen binding receptors, ligands, fusion proteins, and recombinant proteins.

In some embodiments, the antigen of the present disclosure is selected from virus-derived antibodies or tumor-specific antigens.

In some embodiments, the antibodies of the present disclosure are selected from Fab, Fab', F(ab')2, Fv, scFv, sdAb, diabody, camelid antibody, or monoclonal antibody.

In some embodiments, the antigen binding receptors of the present disclosure are selected from chimeric antigen receptors or T cell receptors.

In some embodiments, the target polypeptide of the present disclosure is selected from one or more of antigens, antibodies, antigen binding receptors, ligands, fusion proteins, and recombinant proteins.

As used in the present disclosure, the term "substitution, repetition, deletion or addition of one or more amino acids" wherein substitution refers to the replacement of a nucleotide or amino acid occupying a position with a different amino acid. Deletion refers to the removal of amino acids occupying a certain position. Insertion refers to the addition of amino acids adjacent to and immediately after the amino acid occupying the position. Exemplarily, "mutation" in the present disclosure includes "conservative mutation".

The term "conservative mutation" in the present disclosure refers to a conservative mutation that can normally maintain the function of a protein. Representative examples of conservative mutations are conservative substitutions. Conservative substitution refers to, for example, when the substitution site is an aromatic amino acid, Phe, Trp, and Tyr are mutually substituted mutations; when the substitution site is a hydrophobic amino acid, Leu, Ile, and Val are mutually substituted In the case of polar amino acids, mutations that replace each other between Gln and Asn; in the case of basic amino acids, mutations that replace each other between Lys, Arg, and His; in the case of acidic amino acids, A mutation that replaces each other between Asp and Glu; in the case of an amino acid having a hydroxyl group, a mutation that replaces each other between Ser and Thr. As the substitutions considered as conservative substitutions, specifically, the substitution of Ala to Ser or Thr, the substitution of Arg to Gln, His, or Lys, the substitution of Asn to Glu, Gln, Lys, His or Asp, the substitution of Asp to Asn, Glu or Gln substitution, Cys to Ser or Ala, Gln to Asn, Glu, Lys, His, Asp or Arg, Glu to Gly, Asn, Gln, Lys or Asp, Gly to Pro Replacement, replacement of His to Asn, Lys, Gln, Arg or Tyr, Ile to Leu, Met, Val or Phe, Leu to Ile, Met, Val or Phe, Lys to Asn, Glu, Gln, His or Arg, Met to Ile, Leu, Val or Phe, Phe to Trp, Tyr, Met, Ile or Leu, Ser to Thr or Ala, Thr to Ser or Ala, Trp to Phe or Tyr, Tyr to His, Phe or Trp, and Val Replacement to Met, Ile or Leu. In addition, conservative mutations also include naturally occurring mutations caused by individual differences, differences in strains, and species from which genes are derived.

In the present disclosure, "sequence identity" and "percent identity" refer to the percentage of identical (ie identical) nucleotides or amino acids between two or more polynucleotides or polypeptides. The sequence identity between two or more polynucleotides or polypeptides can be determined by the following method: aligning the nucleotide or amino acid sequences of the polynucleotides or polypeptides and aligning the aligned polynucleotides or polypeptides The number of positions containing the same nucleotide or amino acid residue is scored and compared with the number of positions containing different nucleotides or amino acid residues in the aligned polynucleotide or polypeptide. Polynucleotides may differ at one position, for example, by containing different nucleotides (ie, substitutions or mutations) or deleted nucleotides (ie, nucleotide insertions or nucleotide deletions in one or two polynucleotides). Polypeptides may differ at one position, for example, by containing different amino acids (ie, substitutions or mutations) or missing amino acids (ie, amino acid insertions or amino acid deletions in one or two polypeptides). Sequence identity can be calculated by dividing the number of positions containing the same nucleotide or amino acid residue by the total number of amino acid residues in the polynucleotide or polypeptide. For example, the percent identity can be calculated by dividing the number of positions containing the same nucleotide or amino acid residue by the total number of nucleotide or amino acid residues in the polynucleotide or polypeptide and multiplying by 100.

Exemplarily, in the present disclosure, when a sequence comparison algorithm is used or visual inspection measurement is used to compare and align with the greatest correspondence, two or more sequences or subsequences have at least 40%, 50%, 60% %, 70%, 80%, 85%, 90%, 91%, 92%, 93%, 94%, 95%, 96%, 97%, 98% or 99% nucleotide or amino acid residues Identity" or "Percent Identity". The judgment/calculation of "sequence identity" or "percent identity" can be based on any suitable region of the sequence. For example, a region of at least about 50 residues in length, a region of at least about 100 residues, a region of at least about 200 residues, a region of at least about 400 residues, or a region of at least about 500 residues. In some embodiments, the sequence is substantially the same over the entire length of any one or two compared biopolymers (ie, nucleic acids or polypeptides).

As used in the present disclosure, the term "Reverse Complementary Sequence" means a sequence that is opposite to the sequence of the original polynucleotide and is also complementary to the sequence of the original polynucleotide. Exemplarily, if the original polynucleotide sequence is ACTGAAC, its reverse complementary sequence is GTTCAGT.

As used in this disclosure, the term "polynucleotide" refers to a polymer composed of nucleotides. A polynucleotide can be in the form of a separate fragment or a component of a larger nucleotide sequence structure, which is derived from a nucleotide sequence separated at least once in number or concentration, and can pass standards Molecular biology methods (for example, using cloning vectors) identify, manipulate, and restore sequences and their component nucleotide sequences. When a nucleotide sequence is represented by a DNA sequence (ie A, T, G, C), this also includes an RNA sequence (ie A, U, G, C), where "U" replaces "T". In other words, "polynucleotide" refers to a polymer of nucleotides removed from other nucleotides (individual fragments or entire fragments), or can be a part or component of a larger nucleotide structure, such as expression Vector or polycistronic sequence. Polynucleotides include DNA, RNA and cDNA sequences. "Recombinant polynucleotide" and "recombinant nucleic acid molecule" belong to one type of "polynucleotide".

As used in the present disclosure, the term "recombinant nucleic acid molecule" refers to polynucleotides having sequences that are not linked together in nature. The recombinant polynucleotide can be included in a suitable vector, and the vector can be used to transform into a suitable host cell. The polynucleotide is then expressed in a recombinant host cell to produce, for example, "recombinant polypeptide", "recombinant protein", "fusion protein" and the like. In the present disclosure, a recombinant nucleic acid molecule includes a coding region encoding a polypeptide of interest, and an IRES element connected upstream of the coding region. In some specific embodiments, the recombinant nucleic acid molecule of the present disclosure comprises the following sequence structure:

5'homology arm-3'intron-second exon E2-5'spacer-IRES element-coding region-3'spacer-first exon E1-5' intron-3' Homology arm. Utilizing the ribozyme characteristics of introns, under the initiation of GTP, the junction between the 5'intron and the first exon is broken; the ribozyme cleavage of the first exon further attacks the 3'intron and the first exon. At the junction of the two exons, the 3'intron is dissociated, and the first exon and the second exon are connected to form a circular RNA.

As used in this disclosure, the term "vector" refers to a DNA construct that contains a DNA sequence operably linked to a suitable control sequence to express a gene of interest in a suitable host.

As used in the present disclosure, the term "recombinant expression vector" refers to a DNA structure used to express, for example, a polynucleotide encoding a desired polypeptide. Recombinant expression vectors may include, for example, i) a collection of genetic elements that have a regulatory effect on gene expression, such as promoters and enhancers; ii) structures or coding sequences that are transcribed into mRNA and translated into proteins; and iii) appropriate transcription and the transcription subunits of translation initiation and termination sequences. The recombinant expression vector is constructed in any suitable manner. The nature of the vector is not important, and any vector can be used, including plasmids, viruses, phages, and transposons. Possible vectors for use in the present disclosure include, but are not limited to, chromosomal, non-chromosomal and synthetic DNA sequences, such as viral plasmids, bacterial plasmids, phage DNA, yeast plasmids, and vectors derived from combinations of plasmids and phage DNA, such as lentivirus, DNA of viruses such as retrovirus, vaccinia, adenovirus, fowlpox, baculovirus, SV40 and pseudorabies.

As used in this disclosure, the term "antigen" refers to a molecule that elicits an immune response. This immune response may involve the production of antibodies or the activation of specific immune cells, or both. Any macromolecule, including essentially all proteins or peptides, can be used as an antigen. In the present disclosure, antigens include virus-derived antigens, such as novel coronavirus (SARS-CoV-2) antigens, or tumor-specific antigens.

As used in the present disclosure, the term "antibody" refers to an immunoglobulin or a fragment or derivative thereof, and includes any polypeptide that contains an antigen binding site, regardless of whether it is produced in vitro or in vivo. The term includes, but is not limited to, polyclonal, monoclonal, monospecific, multispecific, non-specific, humanized, single-stranded, chimeric, synthetic, recombinant, hybrid, Mutant, grafted antibodies. The term "antibody" also includes antibody fragments such as Fab, F(ab')2, FV, scFv, Fd, dAb, and other antibody fragments that retain antigen binding function. Normally, such fragments will include antigen-binding fragments.

As used in the present disclosure, the term "single-chain antibody" (scFv) is formed by connecting the variable region of the heavy chain and the variable region of the light chain of an antibody through a short peptide (also called a linker) of a limited number of amino acids. Into antibodies.

As used in the present disclosure, the term "T cell receptor" (T cell receptor, TCR) is a type of T cell receptor capable of targeting heterologous antigens. The TCR of most T cells is composed of α and β peptide chains, and the TCR of a few T cells is composed of γ and δ peptide chains.

As used in this disclosure, the term "chimeric antigen receptor" (CAR) is an artificial receptor that is engineered to contain an immunoglobulin antigen binding domain. Currently, chimeric antigen receptors can include domains such as antigen binding region, hinge region, transmembrane region and intracellular structural region.

The term "host cell" in the present disclosure means any cell type that is easily transformed, transfected, transduced, etc., with a recombinant nucleic acid molecule, circular RNA, or recombinant expression vector containing the present disclosure. The term "recombinant host cell" covers a host cell that is different from the parent cell after the introduction of a recombinant nucleic acid molecule, circular RNA or recombinant expression vector, and the recombinant host cell is specifically achieved by transformation. The host cell of the present disclosure may be a prokaryotic cell or a eukaryotic cell, as long as it is a cell capable of introducing the recombinant nucleic acid molecule, circular RNA or recombinant expression vector of the present disclosure. After introducing the recombinant nucleic acid molecule, circular RNA or recombinant expression vector of the present disclosure, a recombinant host cell expressing the target polypeptide can be obtained.

The terms "transformation, transfection, transduction" in this disclosure have the meaning generally understood by those skilled in the art, that is, the process of introducing 40 foreign DNA into a host. The methods of transformation, transfection, and transduction include any method of introducing nucleic acid into cells, including but not limited to electroporation, calcium phosphate (CaPO4) precipitation, calcium chloride (CaCl2) precipitation, and microinjection. Polyethylene glycol (PEG) method, DEAE-dextran method, cationic liposome method and lithium acetate-DMSO method.

As used in the present disclosure, "treatment" refers to contacting (eg, administering) the strain and/or macrophages of the present invention or a pharmaceutical composition containing them (hereinafter also It is referred to as the "pharmaceutical composition of the present invention") to reduce the symptoms of the disease compared with the absence of contact, and does not mean that it is necessary to completely suppress the symptoms of the disease. Suffering from a disease refers to the appearance of symptoms of disease in the body.

As used in the present disclosure, "prevention" refers to: before contracting a disease, by contacting (for example, administering) the pharmaceutical composition of the present invention, etc., the subject can reduce the symptoms after contracting the disease compared with the absence of contact. Does not mean that the disease must be completely suppressed.

As used in this disclosure, the terms "individual", "patient" or "subject" include mammals. Mammals include, but are not limited to, domestic animals (for example, cattle, sheep, cats, dogs, and horses), primates (for example, human and non-human primates such as monkeys), rabbits, and rodents (for example: Mice and rats).

As used in the present disclosure, the term "high stringency conditions" means that for probes with a length of at least 100 nucleotides, following standard Southern blotting procedures, at 42° C. in 5×SSPE (saline sodium phosphate EDTA) 0.3% SDS, 200 μg/ml sheared and denatured salmon sperm DNA and 50% formamide pre-hybridization and hybridization for 12 to 24 hours. Finally, the carrier material was washed three times with 2×SSC, 0.2% SDS at 65° C., each time for 15 minutes.

As used in the present disclosure, the term "very high stringency conditions" means that for probes with a length of at least 100 nucleotides, following standard Southern blotting procedures, at 42° C. in 5×SSPE (saline sodium phosphate EDTA) 0.3% SDS, 200 μg/ml sheared and denatured salmon sperm DNA and 50% formamide pre-hybridization and hybridization for 12 to 24 hours. Finally, the carrier material was washed three times with 2×SSC, 0.2% SDS at 70° C., each for 15 minutes.

Unless otherwise defined or clearly indicated by the background, all technical and scientific terms in this disclosure have the same meanings as commonly understood by those of ordinary skill in the art to which this disclosure belongs.

Technical Solutions

In the technical solution of the present disclosure, the meanings of the numbers in the nucleotide and amino acid sequence lists in the specification are as follows:

The sequence shown in SEQ ID NO:1 is the nucleotide sequence of the T7 promoter;

The sequence shown in SEQ ID NO: 2 is the nucleotide sequence of 5'homology arm sequence 1 (H1);

The sequence shown in SEQ ID NO: 3 is the nucleotide sequence of 5'homology arm sequence 2 (H2);

The sequence shown in SEQ ID NO: 4 is the nucleotide sequence of the 3'intron of the Type I PIE system;

The sequence shown in SEQ ID NO: 5 is the nucleotide sequence of the second exon (E2) of the class I PIE system;

The sequence shown in SEQ ID NO: 6 is the nucleotide sequence of 5'spacer sequence 1;

The sequence shown in SEQ ID NO: 7 is the nucleotide sequence of 5'spacer sequence 2;

The sequence shown in SEQ ID NO: 8 is the nucleotide sequence of CVB3 IRES;

The sequence shown in SEQ ID NO: 9 is the nucleotide sequence of EV24 IRES;

The sequence shown in SEQ ID NO: 10 is the nucleotide sequence of EV29 IRES;

The sequence shown in SEQ ID NO: 11 is the nucleotide sequence of EV33 IRES;

The sequence shown in SEQ ID NO: 12 is the nucleotide sequence of the chimeric IRES of EV24 and CVB3v;

The sequence shown in SEQ ID NO: 13 is the nucleotide sequence of the chimeric IRES of EV29 and CVB3v;

The sequence shown in SEQ ID NO: 14 is the nucleotide sequence of the chimeric IRES of EV33 and CVB3v;

The sequence shown in SEQ ID NO: 15 is the nucleotide sequence of the first exon (E1) of the class I PIE system;

The sequence shown in SEQ ID NO: 16 is the nucleotide sequence of the 5'intron of the Type I PIE system;

The sequence shown in SEQ ID NO: 17 is the nucleotide sequence of 3'homology arm sequence 1, The sequence shown in SEQ ID NO: 18 is the nucleotide sequence of 3'homology arm sequence 2;

The sequence shown in SEQ ID NO: 19 is the nucleotide sequence of the XbaI restriction site;

The sequence shown in SEQ ID NO: 20 is the nucleotide sequence of EGFP encoding DNA;

The sequence shown in SEQ ID NO: 21 is the EGFP amino acid sequence;

The sequence shown in SEQ ID NO: 22 is the nucleotide sequence of EGFP circular RNA (CVB3 IRES);

The sequence shown in SEQ ID NO: 23 is the nucleotide sequence of EGFP circular RNA (EV24 IRES);
The sequence shown in SEQ ID NO: 24 is the nucleotide sequence of EGFP circular RNA (EV24+CVB3v IRES);
The sequence shown in SEQ ID NO: 25 is the nucleotide sequence of EGFP circular RNA (EV29 IRES)
The sequence shown in SEQ ID NO: 26 is the nucleotide sequence of EGFP circular RNA (EV29+CVB3v IRES);
The sequence shown in SEQ ID NO: 27 is the nucleotide sequence of EGFP circular RNA (EV33 IRES);
The sequence shown in SEQ ID NO: 28 is the nucleotide sequence of EGFP circular RNA (EV33+CVB3v IRES);
The sequence shown in SEQ ID NO: 29 is the nucleotide sequence of EGFP circular RNA (EV29 IRES+H1S1);
The sequence shown in SEQ ID NO: 30 is the nucleotide sequence of EGFP circular RNA (EV29 IRES+H2S2);
The sequence shown in SEQ ID NO: 31 is the nucleotide sequence of RBD encoding DNA;
The sequence shown in SEQ ID NO: 32 is the amino acid sequence of the RBD protein;
The sequence shown in SEQ ID NO: 33 is the nucleotide sequence of RBD circular RNA (EV29 IRES+H1 S1);
The sequence shown in SEQ ID NO: 34 is the nucleotide sequence of EPO encoding DNA;
The sequence shown in SEQ ID NO: 35 is the amino acid sequence of the EPO protein;
The sequence shown in SEQ ID NO: 36 is the nucleotide sequence of EPO circular RNA (EV29 IRES+H1S1);
The sequence shown in SEQ ID NO: 37 is the nucleotide sequence of the DNA encoding the light chain of the PD-1 monoclonal antibody;
The sequence shown in SEQ ID NO: 38 is the amino acid sequence of the light chain of the PD-1 monoclonal antibody;
The sequence shown in SEQ ID NO: 39 is the nucleotide sequence of the light chain circular RNA (EV29 IRES+H1S1) of the PD-1 monoclonal antibody;
The sequence shown in SEQ ID NO: 40 is the nucleotide sequence of the DNA encoding the heavy chain of the PD-1 monoclonal antibody;
The sequence shown in SEQ ID NO: 41 is the amino acid sequence of the heavy chain protein of the PD-1 monoclonal antibody;
The sequence shown in SEQ ID NO: 42 is the nucleotide sequence of the heavy chain circular RNA of the PD-1 monoclonal antibody (EV29 IRES+H1S1);
The sequence shown in SEQ ID NO: 43 is the nucleotide sequence of IL-15 encoding DNA;
The sequence shown in SEQ ID NO: 44 is the amino acid sequence of IL-15 protein;
The sequence shown in SEQ ID NO: 45 is the nucleotide sequence of IL-15 circular RNA (EV29 IRES+H1S1);
The sequence shown in SEQ ID NO: 46 is the nucleotide sequence of PAP encoding DNA;
The sequence shown in SEQ ID NO: 47 is the amino acid sequence of the PAP protein;
The sequence shown in SEQ ID NO: 48 is the nucleotide sequence of PAP circular RNA (EV29 IRES+H1S1);
The sequence shown in SEQ ID NO: 49 is the nucleotide sequence of CD16 CAR encoding DNA;
The sequence shown in SEQ ID NO: 50 is the amino acid sequence of the CD16 CAR protein;
The sequence shown in SEQ ID NO: 51 is the nucleotide sequence of CD16 CAR circular RNA (EV29 IRES+H1S1);
The sequence shown in SEQ ID NO: 52 is the nucleotide sequence of 3'spacer sequence 1;
The sequence shown in SEQ ID NO:53 is the nucleotide sequence of sequence 2 of the 3'spacer.

The present disclosure has discovered in research that although linear mRNA in the prior art has a high protein expression level, it cannot achieve long-term and persistent protein expression. Although the circular RNA disclosed in Reference 15 has increased the protein expression level and expression time of circular RNA to a certain extent, it still cannot meet the requirements of industrialized protein production. At present, it is necessary to have both high protein expression levels and achieve Circular RNA molecule for long-term protein expression.

In some embodiments, the present disclosure provides a recombinant nucleic acid molecule that is then transcribed to form circular RNA. The recombinant nucleic acid molecule includes a coding region encoding the target polypeptide, and an IRES element connected upstream of the coding region. The IRES element can increase the expression level of the target polypeptide, and the circular RNA transcribed with the above-mentioned recombinant nucleic acid molecule can realize efficient and durable protein expression in eukaryotic cells.

The IRES element includes nucleotide sequence with at least 80%, 81%, 82%, 83%, 84%, 85%, 86%, 87%, 88%, 89%, 90%, 91%, 92%, 93%, 94%, 95%, 96%, 97%, 98%, 99%, 100% sequence identity of one or more sequences in the group consisting of any one of SEQ ID NO: 8-11. In some embodiments, the IRES element is CVB3 IRES of the nucleotide sequence shown in SEQ ID NO: 8, EV24 IRES of the nucleotide sequence shown in SEQ ID NO: 9, and the nucleotide sequence shown in SEQ ID NO: 10 EV29 IRES, EV33 IRES with the nucleotide sequence shown in SEQ ID NO: 11. In some embodiments, the IRES element comprises a chimera sequence of CVB3v IRES and any one of EV24 IRES, EV29 IRES, and EV33 IRES.

In some specific embodiments, the recombinant nucleic acid molecule of the present disclosure further comprises a 5' homology arm located upstream of the IRES element, and a 3' homology arm located downstream of the coding region which is complementary to the 5' homology arm.

In the present disclosure, the 5'homology arm includes 5' homology arm 1 (H1) and 5' homology arm 2 (H2 Specifically, the nucleotide sequence of the 5'homology arm has at least 80%, 81%, 82%, 83%, 84%, 85%, 86%, 87%, 88%, 89%, 90%, 91%, 92%, 93%, 94%, 95%, 96%, 97%, 98%, 99%, 100% sequence identity compared with the sequence shown in any of SEQ ID NO: 2-3.the nucleotide sequence of the 3'homology arm has at least 80%, 81%, 82%, 83%, 84%, 85%, 86%, 87%, 88%, 89%, 90%, 91%, 92%, 93%, 94%, 95%, 96%, 97%, 98%, 99%, 100% sequence identity compared with the sequence shown in any of SEQ ID NO: 17-18. In some specific embodiments, the recombinant nucleic acid molecule of the present disclosure further comprises an IRES element located between the 5'homology arm and the IRES element, and between the coding region and the 3'homology arm.

In the present disclosure, the spacer includes a 5'spacer and a 3'spacer. Specifically, the nucleotide sequence of the 5'spacer has at least 80%, 81%, 82%, 83%, 84%, 85%, 86%, 87%, 88%, 89%, 90%, 91%, 92%, 93%, 94%, 95%, 96%, 97%, 98%, 99%, 100% sequence identity compared with which shown in any one of SEQ ID NOs: 6-7. the nucleotide sequence of the 3'spacer has at least 80%, 81%, 82%, 83%, 84%, 85%, 86%, 87%, 88%, 89%, 90%, 91%, 92%, 93%, 94%, 95%, 96%, 97%, 98%, 99%, 100% sequence identity compared with which shown in any one of SEQ ID NOs: 52-53. The sequences of the 5'homology arm, 3' homology arm, and spacer in the present disclosure can further improve the circularization efficiency of the circular RNA formed by the recombinant nucleic acid molecule, thereby increasing the protein expression level of the circular RNA.

In some specific embodiments, the recombinant nucleic acid molecule of the present disclosure further comprises a 3' intron and a second exon located between the 5' homology arm and the IRES element and the first exon and the 5'intron between the 3'homology arm and the coding region.

In the present disclosure, the nucleotide sequence of the 3'intron has at least 80%, 81%, 82%, 83%, 84%, 85%, 86%, 87%, 88%, 89%, 90%, 91%, 92%, 93%, 94%, 95%, 96%, 97%, 98%, 99%, 100% sequence identity compared with the nucleotide sequence shown in SEQ ID NO: 4. The nucleotide sequence of the second exon (E2) has at least 80%, 81%, 82%, 83%, 84%, 85%, 86%, 87%, 88%, 89%, 90%, 91%, 92%, 93%, 94%, 95%, 96%, 97%, 98%, 99%, 100% sequence identity sequence. compared with the nucleotide sequence shown in SEQ ID NO: 5. sequence. The nucleotide sequence of the 5'intron has at least 80%, 81%, 82%, 83%, 84%, 85%, 86%, 87%, 88%, 89%, 90%, 91%, 92%, 93%, 94%, 95%, 96%, 97%, 98%, 99%, 100% sequence identity compared with the nucleotide sequence shown in SEQ ID NO: 16. The nucleotide sequence of the first exon (E1) has at least 80%, 81%, 82%, 83%, 84%, 85%, 86%, 87%, 88%, 89%, 90%, 91%, 92%, 93%, 94%, 95%, 96%, 97%, 98%, 99%, 100% sequence identity compared with the nucleotide sequence shown in SEQ ID NO: 15.

In some preferred embodiments, the structure of the recombinant nucleic acid molecule is as follows:

5'homology arm-3'intron-second exon E2-5'spacer-IRES element-coding region-3'spacer-first exon E1-5' intron-3' Homology arm.

In order to enable the recombinant nucleic acid molecule to be further transcribed to form an RNA molecule, the recombinant nucleic acid molecule may also contain regulatory sequences. Exemplarily, the control sequence is the T7 promoter connected to the upstream of the 5'homology arm, and the T7 promoter sequence is the nucleotide sequence shown in SEQ ID NO:1.

In some embodiments, the present disclosure provides a recombinant expression vector comprising the aforementioned recombinant nucleic acid molecule. Among them, the vector for connecting the recombinant nucleic acid molecule can be various vectors commonly used in the art, such as pUC57 plasmid. Further, the recombinant nucleic acid molecule contains restriction enzyme cutting sites, so that the recombinant expression vector is digested to obtain a linearized vector which is suitable for transcription.

In some embodiments, the present disclosure provides a pre-circularized RNA formed by post-transcription of a recombinant nucleic acid molecule or a linearized recombinant expression vector. Preferably, the pre-circularized RNA has the following structure:

5'homology arm-3'intron-second exon E2-5'spacer-IRES element-coding region-3'spacer-first exon E1-5' intron-3' Homology arm.

FIG. 1 shows the process of obtaining circular RNA from a recombinant expression vector (DNA vector) containing a recombinant nucleic acid molecule: firstly, the DNA vector is digested to obtain a linearized vector, and the linearized DNA vector is transcribed to obtain a pre-circularized RNA. Finally, the pre-circularized RNA is circularized through the following process: using the ribozyme characteristics of the intron, under the initiation of GTP, the junction between the 5'intron and the first exon is broken; The ribozyme cleavage of the first exon further attacks the junction between the 3' intron and the second exon, causing a break at this place, dissociating the 3' intron, and connecting the first exon and the second exon to form a ring RNA.

In some embodiments, the present disclosure provides a circular RNA formed by circularization of the above-mentioned pre-circularized RNA, or circularization of a recombinant nucleic acid molecule or a recombinant expression vector after transcription. Specifically, under the guidance of the regulatory sequence in the recombinant nucleic acid molecule, the recombinant nucleic acid molecule is transcribed to produce a pre-circularized RNA molecule. Specifically, the 5' homology arm in the pre-circularized RNA molecule is complementary to the 3'homology arm, and the ribozyme characteristic of the intron is used to make a break occurs between the 3'intron and the second exon E2, and the first an exon E1 and 5'intron, then E1 and E2 are connected to obtain a Circular RNA sequence with the structure of: second exon E2-spacer-IRES element-coding region-spacer-first exon E1.

In some embodiments, one or more target polypeptides selected from antigens, antibodies, antigen-binding receptors, ligands, fusion proteins, and recombinant proteins are expressed.

In some embodiments, the circular RNA expresses the EGFP protein of the amino acid sequence shown in SEQ ID NO: 21, or the amino acid sequence shown in SEQ ID NO: 21 has been substituted, repeated, deleted or added with one or more amino acids, and has EGFP protein active polypeptide. The nucleotide sequence encoding the EGFP protein is shown in SEQ ID NO:20. The circular RNA expressing the EGFP protein contains the nucleotide sequence shown in any one of SEQ ID NO: 22-30.

In some embodiments, the circular RNA expresses viral antigens. Exemplarily, the viral antigen is the RBD protein having the amino acid sequence shown in SEQ ID NO: 32, or the amino acid sequence shown in SEQ ID NO: 32 has been substituted, repeated, deleted or added with one or more amino acids, and has the RBD protein Active peptides. The nucleotide sequence encoding the RBD protein is shown in SEQ ID NO:31. The circular RNA expressing the RBD protein includes the nucleotide sequence shown in SEQ ID NO:33.

In some embodiments, the circular RNA expresses a recombinant humanized protein. Exemplarily, the recombinant humanized protein is specifically the EPO protein with the amino acid sequence shown in SEQ ID NO: 35, or the amino acid sequence shown in SEQ ID NO: 35 has been substituted, repeated, deleted or added with one or more amino acids, and A polypeptide with EPO protein activity. The nucleotide sequence encoding the EPO protein is shown in SEQ ID NO:34. The circular RNA expressing the EPO protein includes the nucleotide sequence shown in SEQ ID NO:36.

In some embodiments, the circular RNA expresses cytokines. The cytokine is specifically IL-15 protein with the amino acid sequence shown in SEQ ID NO: 44, or the amino acid sequence shown in SEQ ID NO: 44 has been substituted, repeated, deleted or added with one or more amino acids, and has IL-15 protein Active peptides. The nucleotide sequence encoding IL-15 protein is shown in SEQ ID NO:43. The circular RNA expressing IL-15 protein includes the nucleotide sequence shown in SEQ ID NO:45.

In some embodiments, the circular RNA expresses tumor-specific antigens, which include CEA AFP PSA PSMA MAGE-A3 PAP protein and the like. Exemplarily, the tumor-specific antigen is the PAP protein having the amino acid sequence shown in SEQ ID NO: 47, or the amino acid sequence shown in SEQ ID NO: 47 has been substituted, repeated, deleted or added with one or more amino acids, and has PAP protein active polypeptide. The nucleotide sequence encoding the PAP protein is shown in SEQ ID NO:46. The circular RNA expressing the PAP protein includes the nucleotide sequence shown in SEQ ID NO:48.

In some embodiments, the circular RNA expresses the chimeric antigen receptor associated proteins, and the chimeric antigen receptor associated proteins include CD19, CD20, CD133, CD138, BCMA, CD16 protein, and the like. Exemplarily, the expresses the chimeric antigen receptor associated proteins is the CD16 protein having the amino acid sequence shown in SEQ ID NO: 50, or the amino acid sequence shown in SEQ ID NO: 50 has been substituted, repeated, deleted, or added one or more Amino acid and a polypeptide with CD16 protein activity. The nucleotide sequence encoding the CD16 protein is shown in SEQ ID NO:49. The circular RNA expressing the CD16 protein includes the nucleotide sequence shown in SEQ ID NO:51.

In some embodiments, the circular RNA expresses monoclonal antibodies. Exemplarily, the monoclonal antibody is PD-1 monoclonal antibody. The light chain of the PD-1 monoclonal antibody is a polypeptide with the amino acid sequence shown in SEQ ID NO: 38, or the amino acid sequence shown in SEQ ID NO: 38 has undergone substitution, repetition, deletion, or addition of one or more amino acids, and has light Chain active polypeptide. The nucleotide sequence encoding the light chain is shown in SEQ ID NO:37. The circular RNA expressing the light chain of the PD-1 monoclonal antibody contains the nucleotide sequence shown in SEQ ID NO:39. The heavy chain of the PD-1 monoclonal antibody is a polypeptide having the amino acid sequence shown in SEQ ID NO: 41, or the amino acid sequence shown in SEQ ID NO: 41 has undergone substitution, repetition, deletion or addition of one or more amino acids, and has a heavy Chain active polypeptide. The nucleotide sequence encoding the heavy chain is shown in SEQ ID NO:40. The circular RNA expressing the heavy chain of the PD-1 monoclonal antibody contains the nucleotide sequence shown in SEQ ID NO:42.

Since the circular RNA contains IRES elements of specific sequence, 5'spacer, 3'spacer, 5'homology arm, 3'homology arm, and all the elements work colloidally, a highly efficient and good durability of protein expression can be obtained through expressing above-mentioned protein with circular RNA of the present disclosure, which is superior to the existing pre-circularized mRNA and circular RNA and other protein expression elements.

In some embodiments, the present disclosure provides a recombinant host cell comprising the aforementioned recombinant nucleic acid molecule, recombinant expression vector, pre-circularized RNA or circular RNA. Preferably, the recombinant host cell is a cell derived from eukaryotes, and the IRES element of the present disclosure can achieve efficient and durable expression of the target polypeptide in eukaryotic cells.

In some embodiments, the present disclosure provides a pharmaceutical composition comprising the above-mentioned recombinant nucleic acid molecule, recombinant expression vector, pre-circularized RNA, circular RNA, recombinant host cell, or protein expressed by it. The circular RNA of the present disclosure can be used as expression elements for viral antigens, recombinant humanized proteins, tumor-specific antigens, chimeric antigen receptors, etc., or as nucleic acid vaccines directly introduced into organisms to produce viral antigens, Tumor-specific antigens, chimeric antigen receptors, etc.

EXAMPLES

Other objects, features and advantages of the present disclosure will become apparent from the following detailed description. However, it should be understood that the detailed description and specific examples (although representing specific embodiments of the present disclosure) are given for explanatory purposes only, because after reading the detailed description, they are made within the spirit and scope of the present disclosure. Various changes and modifications will become apparent to those skilled in the art.

The experimental techniques and experimental methods used in this example are conventional techniques and methods unless otherwise specified. For example, the experimental methods for which specific conditions are not indicated in the following examples, usually follow conventional conditions such as Sambrook et al., Molecular Cloning: Experiment The conditions described in the laboratory manual (New York: Cold Spring Harbor Laboratory Press, 1989), or according to the conditions recommended by the manufacturer. The materials and reagents used in the examples can be obtained through formal commercial channels unless otherwise specified.

Example 1: Exploring the Expression of Circular mRNA Mediated by Different IRES in 293T Cells 1.1 Experimental Methods and Procedures (1) Plasmid Construction To construct the EGFP target gene containing different elements, this step entrusts Suzhou Genweiz Biotechnology Co., Ltd. to perform gene synthesis and cloning. The DNA vector used here to construct circular RNA includes T7 promoter, 5'homology arm, 3'intron, second exon E2, 5'spacer, IRES element, EGFP coding region, downstream spacer Region, 5'intron, first exon E1, 3'homology arm, and restriction site XbaI for plasmid linearization. The resulting gene fragment was ligated into the pUC57 vector.

The IRES component information is as follows:

| IRES | Content | SEQ ID NO: |
|---|---|---|
| EV24 | Enterovirus EV24Included IRES components | SEQ ID NO: 9 |
| EV29 | Enterovirus EV29Included IRES components | SEQ ID NO: 10 |
| EV33 | Enterovirus EV33Included IRES components | SEQ ID NO: 11 |
| EV24 + CVB3v | The IRES element and v domain of the Enterovirus EV24 is replaced with the v domain of the IRES element of CVB3 IRES. | SEQ ID NO: 12 |
| EV29 + CVB3v | The IRES element and v domain of the Enterovirus EV29 is replaced with the v domain of the IRES element of CVB3 IRES. | SEQ ID NO: 13 |
| EV33 + CVB3v | The IRES element and v domain of the Enterovirus EV33 is replaced with the v domain of the IRES element of CVB3 IRES. | SEQ ID NO: 14 |

Among them, the definition of the v domain of the IRES element can be found in the reference (Proc Natl Acad Sci US A. 2009 Jun. 9; 106(23): 9197-9202.) The EGFP-expressing circular RNA sequences obtained from the above IRES elements are as follows:

| IRES | Coding region gene | SEQ ID NO: |
|---|---|---|
| CVB3 IRES | EGFP | SEQ ID NO: 22 |
| EV24 IRES | EGFP | SEQ ID NO: 23 |
| EV24 + CVB3v IRES | EGFP | SEQ ID NO: 24 |
| EV29 IRES | EGFP | SEQ ID NO: 25 |

-continued

| IRES | Coding region gene | SEQ ID NO: |
|---|---|---|
| EV29 + CVB3v IRES | EGFP | SEQ ID NO: 26 |
| EV33 IRES | EGFP | SEQ ID NO: 27 |
| EV33 + CVB3v IRES | EGFP | SEQ ID NO: 28 |

(2) Preparation of Linear Plasmid Template

1) Plasmid Extraction

① Activate the externally synthesized puncture bacteria, under 37° C./220 rpm/3~4 h ② Expand culturing with the activated bacteria solution, the culture condition: 37° C./220 rpm/overnight ③ Plasmid extraction (Tiangen Endotoxin free small amount medium extraction kit), determine OD value 2) Plasmid Digestion Use XbaI single enzyme digestion method to digest the above 1) Prepare plasmid The digestion system is as follows:

TABLE 1

| Reagent | Volume |
|---|---|
| Plasmid | 10 μg |
| Enzyme (1000 units) | 5 μl |
| 10 × cutsmart buffer | 50 μl |
| Nuclease free, $H_2O$ | Total, 500 μl |

Digestion overnight at 37° C. A universal DNA gel recovery kit (Tiangen Biochemical Technology Co., Ltd.) was used to recover the digested product, determine the OD value, and identify the digested product by 1% agarose gel electrophoresis. The purified linear plasmid template is used for in vitro transcription.

(3) Preparation of Pre-Circularized mRNA by In Vitro Transcription

1) In Vitro Transcription

Use T7 in vitro transcription kit (APExBIO T7 High Yield RNA Synthesis Kit) to synthesize mRNA The transcription system is as follows:

TABLE 2

| Reagent | Volume |
|---|---|
| 10 × Reaction Buffer | 2 μl |
| ATP (20 mM) | 2 μl |
| CTP (20 mM) | 2 μl |
| UTP (20 mM) | 2 μl |
| GTP (20 mM) | 2 μl |
| Linearized DNA template | 1 μg |
| T7 RNA Polymerase Mix | 2 μl |
| RNA Nuclease free, $H_2O$ | Total 20 μl |

Incubate at 37° C. for 2 h, then digest the linear DNA template with DNase I. Digestion conditions: Digestion at 37° C. for 15 minutes.

2) Purification of Pre-Circularized mRNA

The transcription product obtained in 1) above was purified using a silicon membrane spin column method (Thermo, GeneJET RNA Purification Kit), and the OD value was measured and the RNA size was identified by 1% denaturing agarose gel electrophoresis.

The formula of 1% denatured agarose gel is as follows:

①, Weigh 1 g agarose to 72 ml nuclease-free, $H_2O$, and heat it in a microwave oven to dissolve;

② When the above agarose is cooled to 55~60° C., add 0.1% gel red, 10 ml 10×MOPS, 18 ml formaldehyde in a fume hood, and pour glue.

The process of denaturing agarose gel electrophoresis is as follows: take an equal volume of sample RNA and 2× Loading buffer, and denature at 65~70° C. for 5~10 min. The sample was loaded and electrophoresis was carried out under the conditions of 100V/30 min, and then photographed with a gel imaging system.

(4) mRNA Circularization

1) Cyclization Reagent:

GTP Buffer: 50 mM Tris-HCl, 10 mM $MgCl_2$, 1 mM DTT, pH 7.5

2) Cyclization System and Conditions:

TABLE 3

| Solution | Volume |
|---|---|
| mRNA | 25 μg RNA solution |
| GTP solution (20 mM) | 50 μl |
| GTP buffer | Add up to 500 μl |

The above solution was heated at 55° C. for 15 minutes, and the circularized RNA product was purified using a silicon membrane spin column method (Thermo, GeneJET RNA Purification Kit). The OD value was measured and the RNA size was identified by 1% denaturing agarose gel electrophoresis.

3) Identification of Circular RNA

① 1% denatured agarose gel identification:

A. Reagent preparation: Add 1 g of agarose powder to 72 ml of nuclease-free water, heat to melt the agar pond, and add 10 ml of 10×MOPS buffer. Then add 18 ml of fresh 37% formaldehyde in a fume hood, mix well, and pour the gel into the tank.

B. mRNA detection: Take about 500 ng mRNA solution, add an equal volume of 2×RNA loading buffer and mix well, heat at 65° C. for 5 minutes, load the sample for agarose gel detection.

② Circularized mRNA RT-RCR and sequencing identification

A.) mRNA Reverse Transcription System and Conditions

TABLE 4

| Solution | Volume |
|---|---|
| mRNA | 1 μg RNA solution |
| RT primer Mix | 4.0 μl |
| Primerscript RT Enzye Mix I | 1.0 μl |
| 5 × primerscript buffer 2 | 4.0 μl |
| Nuclease-free water | Add up to 20 μl |

The experimental group: cyclized mRNA and control group: uncyclized mRNA were prepared according to the above system, heated at 37° C. for 15 minutes, heated at 85° C. for 5 s, and stored at 4° C.

B.) PCR Amplification System and Conditions of Reverse Transcription Products

TABLE 5

| Solution | Volume |
|---|---|
| Reverse transcription product | 1.0 μl |
| 10 × buffer | 2.0 μl |
| dNTP | 1.6 μl |
| primer-F (10 μM) | 1.0 μl |
| primer-R (10 μM) | 1.0 μl |
| Taq Enzyme | 0.5 μl |
| Nuclease-free water | 12.9 μl |

PCR amplification program: 95° C., 1 min; 95° C., 30 s; 60° C., 30 s; 72° C., 30 s; (35 cycles) 72° C., 7 min; 4° C.

C. PCR Product Cutting and Purification

Nucleic acid electrophoresis, select RT-RCR DNA bands that specifically exist in the experimental group but not in the control group, cut gel and recover, and purify with a universal DNA purification and recovery kit. Take purified DNA and primer EV29-EGFP-F: GTGACAGCAGCAGGAATCACA, Primer EV29-EGFP-R: TGGGATCAACCCACAGGCT was sent to Genweiz Company for forward and reverse sequencing.

(5) Transfection of Circular mRNA Encoding EGFP into 293T Cells and Measurement of Fluorescence Intensity 1) Cell Culture:

293T was inoculated in DMEM high glucose medium containing 10% fetal bovine serum and 1% double antibody, and cultured in a 37° C., 5% CO2 incubator. The cells are subcultured every 2-3 days.

2) Cell Transfection:

Before transfection, 293T cells were seeded in a 24-well plate at 1×105 cells/well and cultured in a 37° C., 5% CO2 incubator. After the cells reach 70-90% confluency, use Lipofectamine MessengerMax (Invitrogen) transfection reagent to transfect mRNA into 293T cells at 500 ng/well. The specific operations are as follows:

① Dilute Messenger MAXTM Reagent

TABLE 6

| Reagent | Volume/hole |
|---|---|
| MEM serum-free medium | 25 μl |
| Messenger MAXTM Reagent | 0.75 μl |

After dilution and mixing, incubate at room temperature for 10 min.

② Dilute mRNA

TABLE 7

| Reagent | Volume/hole |
|---|---|
| mRNA | 1 μl |
| MEM serum-free medium | Fill up to 25 μl |

③ Take mixed and diluted Messenger MAXTM Reagent and mRNA (1:1)

TABLE 8

| Reagent | Volume/hole |
|---|---|
| Diluted Messenger MAXTM Reagent | 25 μl |
| Diluted mRNA | 25 μl |

After dilution and mixing, incubate at room temperature for 5 min.

④ Take 50 ul of the above mixture and slowly add it to the 24-well plate and incubate in a 37° C., 5% CO2 incubator.

3) Protein Expression Detection

① Cell fluorescence observation: Observe the expression of EGFP under a 200× fluorescence microscope on 293T cells 1-10 days after transfection.

② Flow cytometry to detect the average fluorescence intensity of cells: 293T cells 1-10 days after transfection were used to detect the average fluorescence intensity of cells with a flow cytometer.

1.2 Results

1) DNA Transcription Template Preparation

① Plasmid extraction concentration: pUC57-CVB3-EGFP: 271.2 ng/μl, pUC57-EV24-EGFP: 245.4 ng/ul, pUC57-EV24+CVB3v-EGFP: 263.8 ng/μl, pUC57-EV29-EGFP: 277.9 ng/μl, pUC57-EV29+CVB3v-EGFP; 249.9 ng/μl, PUC57-EV33-EGFP: 273.0 ng/μl, PUC57-EV33+CVB3v-EGFP: 283.3 ng/μl;

② DNA concentration after plasmid digestion and linearization: pUC57-CVB3-EGFP: 120.6 ng/μl, pUC57-EV24-EGFP: 134.5 ng/ul, pUC57-EV24+CVB3v-EGFP: 125.8 ng/μl, pUC57-EV29-EGFP: 146.1 ng/μl, pUC57-EV29+CVB3v-EGFP: 119.2 ng/μl, pUC57-EV33-EGFP: 141.1 ng/μl, pUC57-EV33+CVB3v-EGFP: 137.9 ng/μl;

2) mRNA Transcription and Circularization

① RNA concentration after mRNA transcription and purification: CVB3-EGFP: 1149.8 ng/μl, EV24-EGFP: 1168.5 ng/μl, EV24+CVB3v-EGFP:1284.6 ng/μl, EV29-EGFP: 1245.5 μg/μl, EV29+CVB3vEGFP: 1111.8 ng/μl, EV33-EGFP: 1180.4 ng/μl, EV33+CVB3v-EGFP: 1148.5 ng/μl;

② RNA concentration after mRNA circularization and purification: CVB3-EGFP: 482.8 ng/μl, EV24-EGFP: 462.4 ng/ul, EV24+CVB3v-EGFP: 532.5 ng/ul, EV29-EGFP: 444.5 μg/μl, EV29+CVB3-EGFP: 447.2 ng/μl, EV33-EGFP: 452.0 ng/μl, EV33+CVB3 EGFP: 415.5 ng/μl;

③ RNA denaturing agarose gel electrophoresis.

Figure 2:
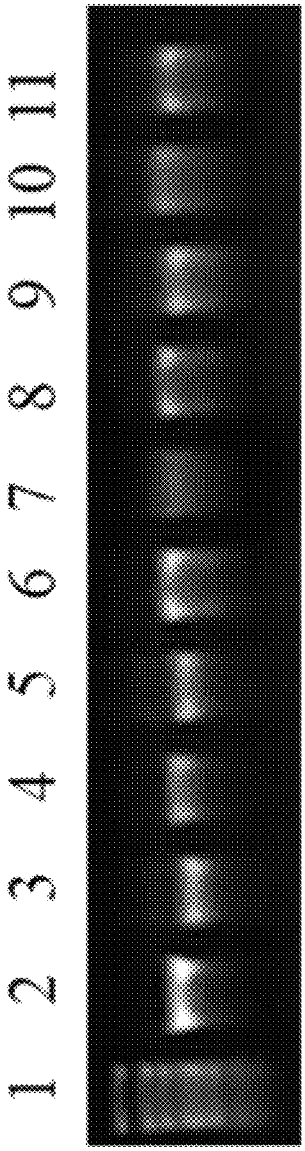
FIG. 2 shows the agarose gel electrophoresis diagram for identifying RNA loops.

As shown in FIG. 2: The electrophoresis of denatured agarose gel showed that the circularized mRNA migrated faster on the gel than the pre-circularized mRNA.

3) RT-PCR and Gene Sequencing to Identify mRNA Loops

Figure 3:
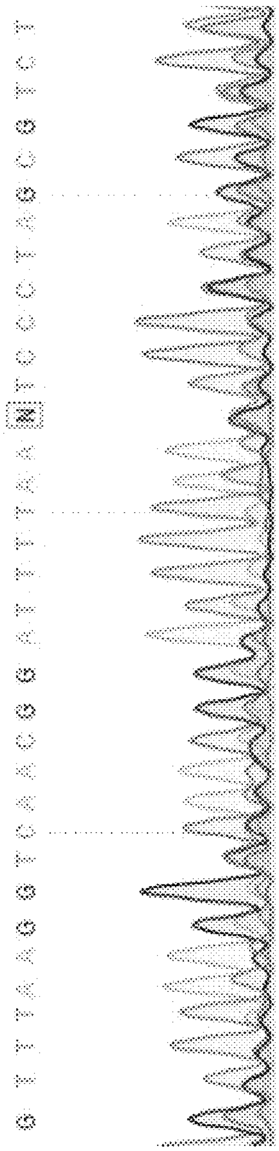
FIG. 3 shows the results of sequencing to identify RNA ring formation.

In order to identify whether the RNA obtained from the circularization reaction is circular RNA, RT-PCR and DNA sequencing methods are used for detection. According to the basic principle of RNA circularization, through the ribozyme characteristics of introns, under the initiation of GTP, the junction between the 5'intron and the first exon E1 will be broken, and the nucleic acid at the first exon E1 The breach will attack the junction of the 3'intron and the second exon E2, causing the junction to break, the 3'intron will dissociate, and the first exon E1 and the second exon E2 will form a common Valence link, and finally form circular RNA. Therefore, by amplifying the connecting sequence containing the first exon E1 and the second exon E2 and performing sequencing, it can be used as the final basis for determining whether the RNA is looped. CDNA was obtained by RNA reverse transcription reaction mediated by random primers. Using cDNA as a template, Specific primers are used for PCR amplification. The experimental results showed that no specific amplified bands were seen in the pre-circularized mRNA group, and specific amplified bands were seen in the circular mRNA group. The specific bands are recovered by cutting gel, and DNA sequencing is performed after purification. As shown in FIG. 3, the sequencing results showed that the DNA band contains the ligated E1 and E2 sequences. The circular RNA contains the connected E1-E2 RNA sequence, indicating that the RNA has been connected into a loop.

4) Protein Expression Detection

Figure 4:
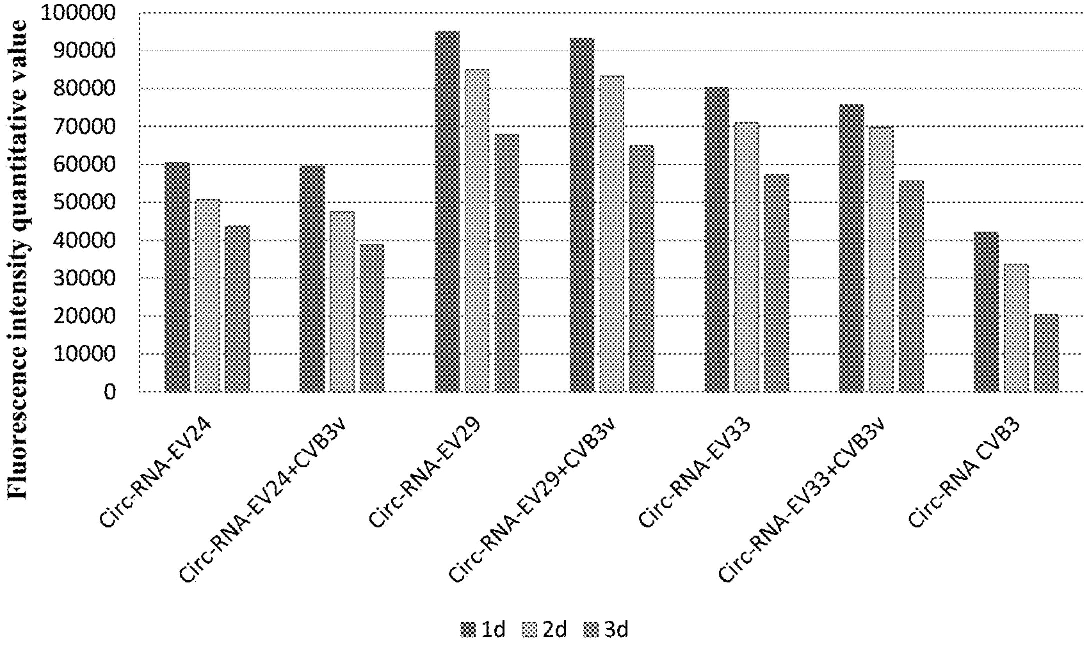
FIG. 4 shows different IRES elements (Circ-RNA-EV24, Circ-RNA-EV24+CVB3v, Circ-RNA-EV29, Circ-RNA-EV29+CVB3v, Circ-RNA-EV33, Circ-RNA-EV33+CVB3v, Circ-RNA-CVB3)-mediated protein expression level.

The quantitative test results of fluorescence intensity 1-3 days after cell transfection are shown in FIG. 4. Compared with the circular EGFP mRNA containing CVB3 IRES (Circ-RNA CVB3, reference 15), it contains EV24 IRES, and EV24 is chimeric with CVB3v. Cyclic mRNA-mediated cellular fluorescence of IRES (EV24+CVB3v), EV29 IRES, EV29 and CVB3v chimeric IRES (EV29+CVB3v), EV33 IRES, EV33 and CVB3v chimeric IRES (EV33+CVB3v) is stronger, Which shows that the circular mRNA containing different IRES combinations provided by this patent can mediate stronger protein expression.

Figure 5:
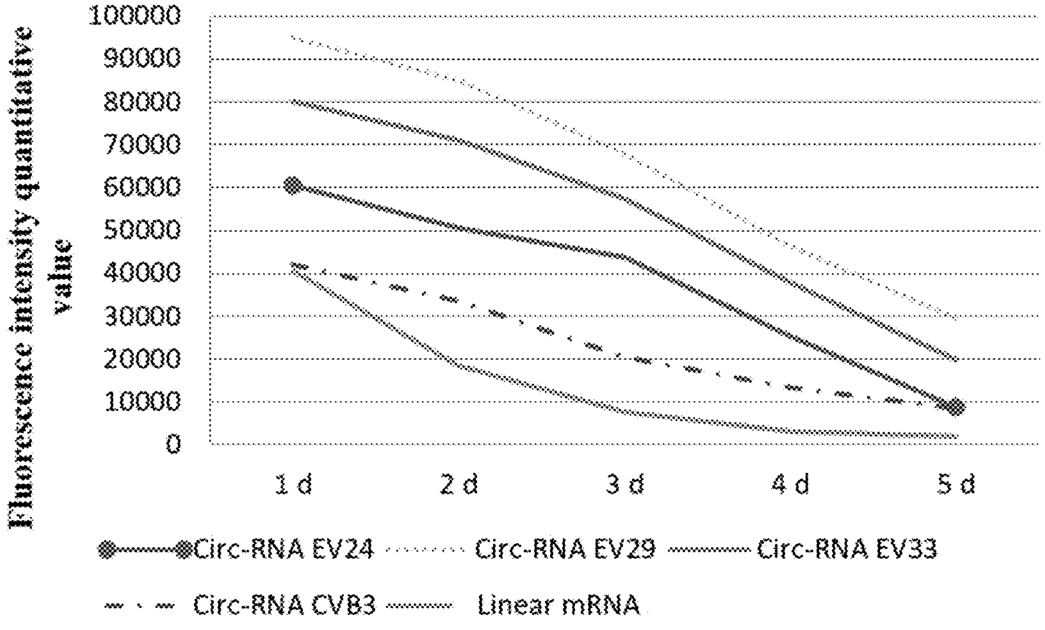
FIG. 5 shows the duration of protein expression mediated by different IRES elements (Circ-RNA-EV24, Circ-RNA-EV29, Circ-RNA-EV33, Circ-RNA-EV33+CVB3v, pre-circularized mRNA)
Figure 6:
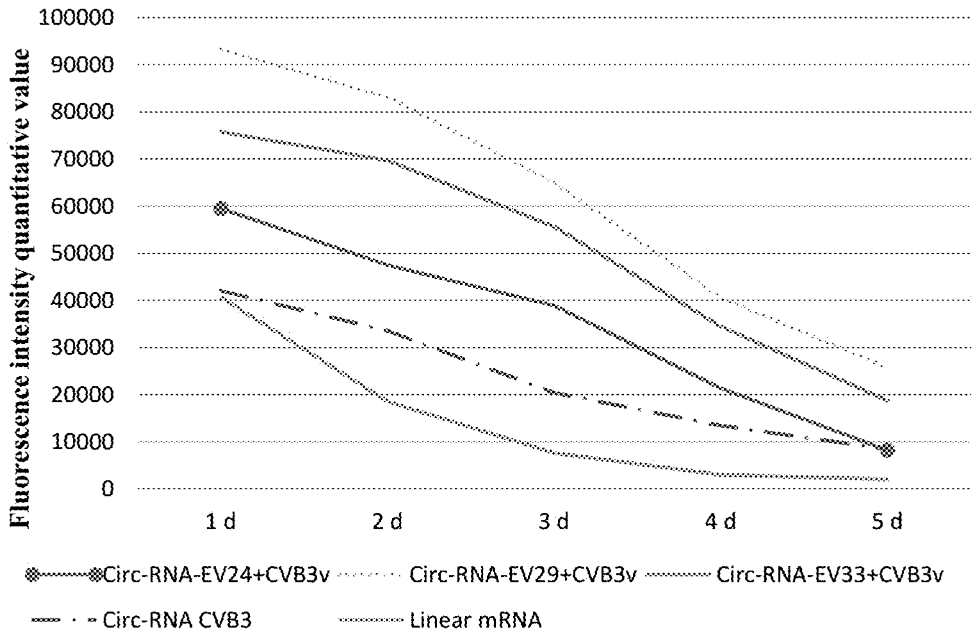
FIG. 6 shows the duration of protein expression mediated by different IRES components (Circ-RNA EV24+CVB3v, Circ-RNA-EV29+CVB3v, Circ-RNA EV33+CVB3v, Circ-RNA CVB3 and linear mRNA)

In order to identify the persistence of this series of circular mRNA-mediated protein expression, the fluorescence intensity of cells 1-5 days after transfection was quantified. The test results are shown in FIG. 5 and FIG. 6: Compared with the circular EGFP mRNA containing CVB3 IRES (Circ-RNA CVB3, cited reference 15), it contains EV24 IRES, EV24+CVB3v IRES, EV29 IRES, EV29+CVB3v IRES, EV33 IRES, EV33+CVB3v IRES circular mRNA-mediated EGFP expression is stronger and longer lasting, and it is also significantly better than linear EGFP mRNA (standard product purchased from APExBio, Cap1 cap structure and PolyA tail) mediated The expression of EGFP is stronger and longer lasting.

Example 2: Expression of Circular mRNA Obtained by Combining EV29 IRES with Different Homology Arms and Spacer Sequences in 293T Cells 2.1 Experimental Methods and Procedures On the basis of the above-mentioned Example 1, using the same intron and exon elements as the above-mentioned example, with EV29 IRES (nucleotide sequence shown in SEQ ID NO: 10), a novel 5'homology arm 1 (nucleotide sequence shown in SEQ ID NO: 2), 3'homology arm 1 (nucleotide sequence shown in SEQ ID NO: 17) and 5'spacer 1 sequence (SEQ ID NO: 6 The nucleotide sequence shown) and the 3'spacer 1 sequence (the nucleotide sequence shown in SEQ ID NO: 52) are used as the basic elements of circular mRNA to construct a circular mRNA encoding green fluorescent protein (EGFP) (Circ-RNA EV29 H1S1).

Using the same intron and exon elements as the above circular mRNA, EV29 IRES, 5'homology arm 2 (nucleotide sequence shown in SEQ ID NO: 3), 3'homology arm 2 (SEQ ID NO: ID NO: 18), 5'spacer 2 sequence (SEQ ID NO: 7 nucleotide sequence) and 3'spacer 2 sequence (SEQ ID NO: 53 As the basic element of circular mRNA, a circular mRNA (Circ-RNA EV29 H2S2) encoding green fluorescent protein (EGFP) is constructed.

The DNA sequence encoding EGFP is shown in SEQ ID NO:20. The DNA synthesis was commissioned by Suzhou Genweiz Biotechnology Co., Ltd. to complete. Eventually will contain T7 promoter, class I PIE element, 5'homology arm 1, 3'homology arm 1, 5'spacer 1, 3'spacer 1, EV29 IRES element, EGFP coding region (or T7 promoter, Class I PIE element, 5'homology arm 2, 3'homology arm 2, 5'spacer 2, 3'spacer 2, EV29 IRES element, EGFP coding region) complete DNA fragments were cloned into pUC57 plasmid.

Plasmid DNA linearization, pre-circularized mRNA in vitro transcription, pre-circularized mRNA purification, mRNA loop reaction, circular mRNA purification, cell culture and transfection, etc., are all the same as in Example 1 in 1.1.

2.2 Results 2.2.1 Results

1) DNA Linearization Template Preparation

① Plasmid extraction concentration: pUC57-CVB3-EGFP: 356.4 ng/μl, pUC57-EV29-EGFP: 481.9 ng/μl, pUC57-EV29-EGFP H1S1: 283.1 ng/μl, pUC57-EV29-EGFP H2S2: 303.1 ng/μl;

② Plasmid digestion linearization concentration: pUC57-CVB3-EGFP: 249.6 ng/μl pUC57-EV29-EGFP: 289 ng/μl, pUC57-EV29-EGFP H1S1: 293 ng/μl, pUC57-EV29-EGFP H252: 294 ng/μl;

2) mRNA Transcription and Circularization

Figure 7:
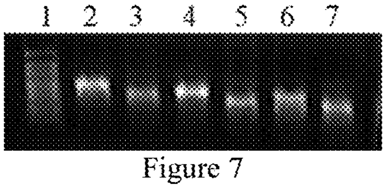
FIG. 7 shows the agarose gel electrophoresis diagram for identifying RNA loops.

① Concentration after mRNA transcription and purification: CVB3-EGFP: 506.3 ng/μl, EV29-EGFP: 527.5 ng/μl, EV29-EGFP H1S1: 573.2 ng/μl, EV29-EGFP H2S2: 564.9 ng/μl;

② Concentration after purification of mRNA circularization: CVB3-EGFP: 257.4 ng/μl, EV29-EGFP: 236.2 ng/μl, EV29-EGFP H1S1: 208.0 ng/μl, EV29-EGFP H2S2: 240.3 ng/μl;

Denaturing agarose gel was used to identify RNA loops. The experimental results are shown in FIG. 7: In the denatured agarose gel electrophoresis, the circularized mRNA of each group migrates faster on the gel than the corresponding pre-circularized mRNA before circularization.

③ Protein expression detection

Figure 8:
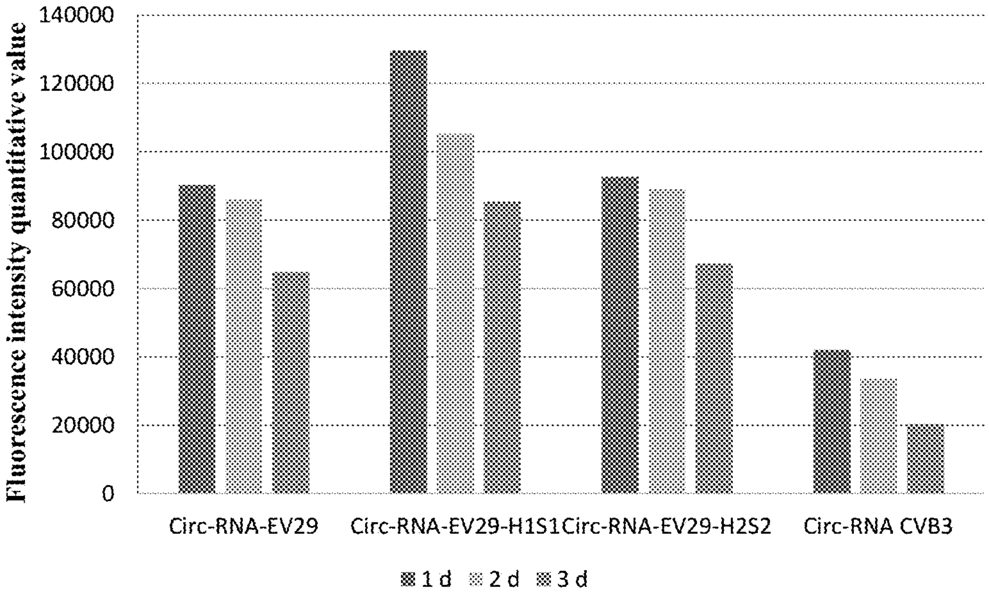
FIG. 8 shows the protein expression levels mediated by different IRES elements (Circ-RNA-EV24, Circ-RNA-EV29-H1S1, Circ-RNA-EV29-H2S2, Circ-RNA-CVB3)

The 1-3d fluorescence quantification after cell transfection is shown in FIG. 8. The fluorescent protein expression mediated by circular mRNA Circ-RNA EV29-EGFP H1S1 was significantly higher than that of the Circ-RNA EV29-EGFP group, and also significantly higher than the amount corresponding to the Circ-RNA CVB3-EGFP group. It shows that the novel combination of 5'homology arm 1, 3'homology arm 1 and 5'spacer 1, 3'spacer 1 provided by the present invention can effectively improve circular mRNA-mediated protein expression. The expression of fluorescent protein mediated by circular mRNA Circ-RNA EV29-EGFP H2S2 was higher than that of the Circ-RNA EV29-EGFP group, and was significantly higher than that of the Circ-RNA CVB3-EGFP group. It shows that the novel combination of 5'homology arm 2, 3'homology arm 2 and 5'spacer 2, 3'spacer 2 provided by the present invention can increase circular mRNA-mediated protein expression.

Figure 9:
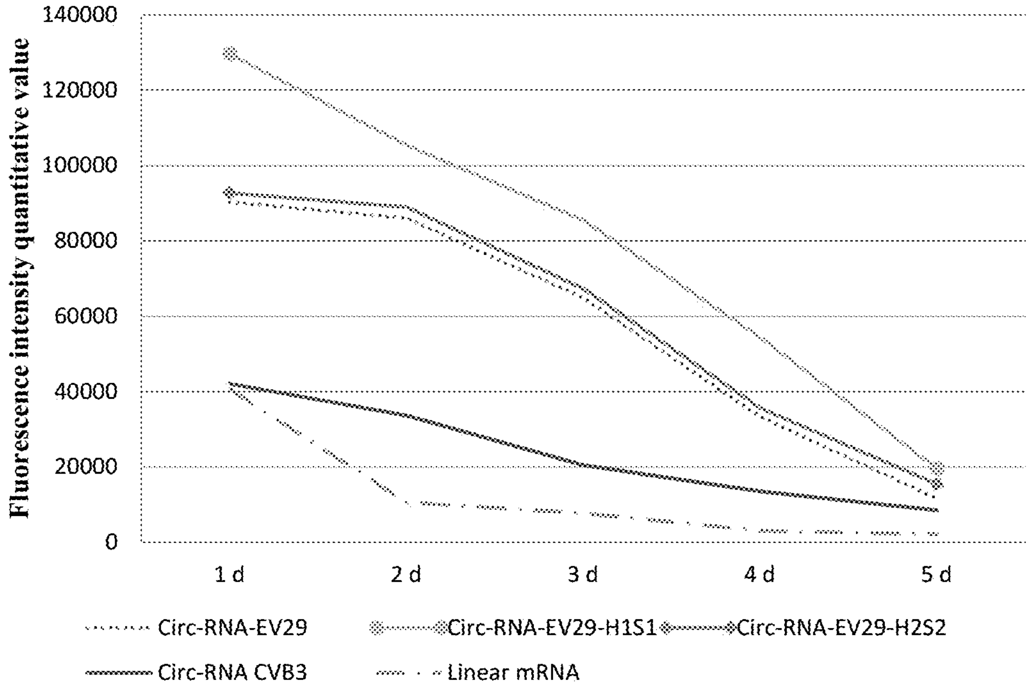
FIG. 9 shows the duration of protein expression mediated by different IRES elements (Circ-RNA-EV29, Circ-RNA EV2-H1S1, Circ-RNA EV2-H2S2, Circ-RNA CVB3, and pre-circularized mRNA).

In order to identify the persistence of different circular mRNA-mediated protein expression, the fluorescence of the cells was quantified 1-5 days after transfection. As shown in FIG. 9, Circ-RNA EV29-EGFP H1S1 protein mediated fluorescence, intensity and persistence of its expression was higher than Circ-RNA EV29-EGFP group and Circ-RNA CVB3-EGFP group. It shows that the novel combination of 5'homology arm 1, 3'homology arm 1 and 5'spacer 1, 3'spacer 1 provided by the present invention can effectively improve the persistence of circular mRNA-mediated protein expression. The persistence of fluorescent protein expression mediated by Circ-RNA EV29-EGFP H2S2 was comparable to that of the Circ-RNA EV29-EGFP group, but significantly higher than that of the Circ-RNA CVB3-EGFP group. It shows that the novel combination of 5'homology arm 2, 3'homology arm 2 and 5'spacer 2, 3'spacer 2 provided by the present invention, its circular mRNA-mediated protein expression is significantly better than that of Patent Citation 15 design and methods provided. Further, all the above cyclic durability mRNA of EGFP expression were significantly higher than the linear mRNA (purchased from standard APExBio comprising Cap1 PolyA tail and cap structure).

Example 3: Circular mRNA Encoding the New Coronavirus Spike Antigen RBD Protein to Achieve Protein Expression in 293T Cells 3.1 Experimental Methods and Procedures On the basis of the above-mentioned Example 2, the EV29 IRES, 5'homology arm 1, 3'homology arm 1 and 5'spacer 1, 3'spacer 1 sequence were used as the basic elements of circular mRNA to construct a new coding RBD domain coronavirus Spike antigen (receptor binding domain) cyclic mRNA. The RBD protein sequence is shown in SEQ ID NO:32, and the DNA sequence encoding RBD is shown in SEQ ID NO:31. The DNA synthesis was commissioned by Suzhou Genweiz Biotechnology Co., Ltd. to complete.

Finally, a complete DNA fragment containing T7 promoter, type I PIE elements, 5'homology arm 1, 3'homology arm 1, 5'spacer 1, 3'spacer 1, EV29 IRES, and RBD coding region will be cloned into pUC57 plasmid. Plasmid DNA is linearized, pre-circularized mRNA is transcribed in vitro, pre-circularized mRNA is purified, mRNA is circularized, and circular mRNA is purified to obtain circular mRNA with the sequence shown in SEQ ID NO: 33. The cell culture and transfection methods are the same as in Example 1 1.1. The His-tag ELISA detection kit was used to quantitatively detect the secreted His-RBD protein (Nanjing GenScript Biotechnology Co., Ltd.).

3.2 Result

TABLE 9

| Nucleic acid | Concentration |
|---|---|
| pUC57-EV29-RBD-H1S1 plasmid (purified) | 342.2 ng/μl |
| pUC57-EV29-RBD-H1S1 linearized plasmid (purified) | 264.3 ng/μl |
| EV29-RBD-H1S1 pre-circularized mRNA (purified) | 508.5 ng/μl |
| EV29-RBD-H1S1 cyclic mRNA (purified) | 236.2 ng/μl |

Detected by His-tag ELISA, the amount of protein obtained by expressing RBD-His circular mRNA in 293T for 1-5 days are 21.6, 35.4, 40.3, 28.6, 22.7 ng/ml, respectively, indicating that the circular mRNA of the present disclosure can achieve RBD efficient and persistent expression of the protein.

Example 4: Circular mRNA Encoding EPO to Achieve Protein Expression in 293T Cells 4.1 Experimental Methods and Procedures Based on Example 2 above, EV33 IRES, 5'homology arm 1, 3'homology arm 1 and 5'spacer 1, 3'spacer 1 were used as the basic elements of circular mRNA to construct a coding erythropoiesis hormone (EPO) cyclic mRNA. The DNA and protein sequences encoding EPO are shown in SEQ ID NO: 34 and SEQ ID NO: 35, respectively. The DNA synthesis was commissioned by Suzhou Genweiz Biotechnology Co., Ltd. to complete. Ultimately it contains the T7 promoter, Class I PIE elements, 5' homology arm 3' homology arm 1,5' spacer region, 3' spacer region 1, EV33 IRES, the complete EPO coding region DNA fragment was cloned into the pUC57 plasmid. Plasmid DNA linearization, linearized mRNA in vitro transcription, pre-circularized mRNA purification, mRNA circularization, circular mRNA purification, cell culture and transfection methods are the same as in Example 1. 1.1. EPO ELISA detection kit (Thermo Fisher) was used to quantify the EPO protein expressed by 293T.

4.2 Result

TABLE 10

| Nucleic acid | Concentration |
|---|---|
| pUC57-EV33-EPO-H1S1 plasmid (purified) | 297.5 ng/μl |
| pUC57-EV33-EPO-H1S1 linearized plasmid (purified) | 275.4 ng/μl |
| EV33-EPO-H1S1 pre-circularized mRNA (purified) | 375.3 ng/μl |
| EV33-EPO-H1S1 cyclic mRNA (purified) | 286.7 ng/μl |

Detected by EPO ELISA, the amount of protein obtained from EPO circular mRNA expression in 293T for 1-5 days is 35.6, 42.8, 56.4, 50.3, 25.7 ng/ml, respectively, indicating that the circular mRNA of the present disclosure can achieve the high efficiency and persistent expression of EPO protein.

Example 5: Circular mRNA Encoding PD-1 Monoclonal Antibody to Achieve Protein Expression in 293T Cells 5.1 Experimental Methods and Procedures On the basis of the above-mentioned Example 2, the EV29 IRES, 5'homology arm 1, 3'homology arm 1 and 5'spacer 1, 3'spacer 1 were used as the basic elements of circular mRNA to construct the coding resistance cell death receptor 1 (PD-1) monoclonal antibody) circular mRNA. Encoding the light chain of the monoclonal antibody anti-PD1 DNA and protein sequences, respectively as SEQ ID NO: 37 and SEQ ID NO: 38, the monoclonal antibody anti-PD1 encoding the heavy chain DNA and protein sequences, respectively as SEQ ID NO: 40 and SEQ ID NO: 41 shown. The DNA synthesis was commissioned by Suzhou Genweiz Biotechnology Co., Ltd. to complete. Eventually it will contain T7 promoter, type I PIE elements, 5'homology arm 1, 3'homology arm 1, 5'spacer 1, 3'spacer 1, EV29 IRES, a complete DNA fragment of the PD1 light chain coding region cloned into the plasmid pUC57. Similarly, it will contain T7 promoter, class I PIE elements, 5'homology arm 1, 3'homology arm 1, 5'spacer 1, 3'spacer 1, EV29 IRES, the complete heavy chain coding region of PD1 DNA fragment was cloned into the plasmid pUC57. Plasmid DNA linearization, pre-circularized mRNA in vitro transcription, pre-circularized mRNA purification, mRNA loop reaction, circular mRNA purification, to obtain two circular RNAs with the sequence shown in SEQ ID NO: 39 or 42, cell culture, etc. The method is the same as 1.1 of Example 1. Both monoclonal antibody PD1 mRNA encoding the light chain and heavy chain in 1:1 ratio, were transfected into 293T cells. Transfection method described in Example 1. The PD1 protein expressed by 293T was quantified using PD1 ELISA detection kit (Thermo Fisher).

5.2 Results

TABLE 11

| Nucleic acid | Concentration |
|---|---|
| pUC57-EV29-PD1L-H1S1 plasmid (purified) | 279.3 ng/μl |
| pUC57-EV29-PD1L-H1S1 linearized plasmid (purified) | 204.2 ng/μl |
| EV29-PD1L-H1S1 pre-circularized mRNA (purified) | 396.5 ng/μl |
| EV29-PD1L-H1S1 cyclic mRNA (purified) | 247.2 ng/μl |
| pUC57-EV29-PD1H-H1S1 plasmid (purified) | 268.6 ng/μl |
| pUC57-EV29-PD1H-H1S1 linearized plasmid (purified) | 201.3 ng/μl |
| EV29-PD1H-H1S1 pre-circularized mRNA (purified) | 304.7 ng/μl |
| EV29-PD1H-H1S1 cyclic mRNA (purified) | 207.4 ng/μl |

Detected by PD1 monoclonal antibody ELISA, the amount of protein obtained from the expression of PD1 monoclonal antibody circular mRNA in 293T for 1-5 days is 120.3, 234.6, 356.4, 221.6, and 104.8 ng/ml, respectively, indicating that the circular mRNA of the present disclosure can achieve PD1 mAb efficient, long-lasting expression.

Example 6: Circular mRNA Encoding Cytokine IL-15 to Achieve Protein Expression in 293T Cells 6.1 Experimental Methods and Procedures Based on the above-mentioned Example 2, the EV29 IRES, 5'homology arm 1, 3'homology arm 1, 5'spacer 1, 3'spacer 1 were used as the basic elements of circular mRNA to construct an encoding interleukin 15 (IL-15) circular mRNA. The DNA and protein sequences encoding IL-15 are shown in SEQ ID NO: 43 and SEQ ID NO: 44, respectively. The DNA synthesis was commissioned by Suzhou Genweiz Biotechnology Co., Ltd. to complete. Eventually it will contain T7 promoter, class I PIE elements, 5'homology arm 1, 3'homology arm 1, 5'spacer 1, 3'spacer 1, EV29 IRES, a complete DNA fragment of IL-15 coding region cloned into the plasmid pUC57. Plasmid DNA linearization, pre-circularized mRNA in vitro transcription, pre-circularized mRNA purification, mRNA loop reaction, circular mRNA purification to obtain circular RNA with the sequence shown in SEQ ID NO: 45, cell culture and transfection methods All are the same as 1.1 of Example 1. IL-15 ELISA detection kit (Thermo Fisher) was used to quantify the IL-15 protein expressed by 293T.

6.2 Results

TABLE 12

| Nucleic acid | Concentration |
|---|---|
| pUC57-EV29-1L15-H1S1 plasmid (purified) | 286.3 ng/μl |
| pUC57-EV29-1L15-H1S1 linearized plasmid (purified) | 251.5 ng/μl |
| EV29-IL15-H1S1 pre-circularized mRNA (purified) | 311.3 ng/μl |
| EV29-IL15-H1S1 cyclic mRNA (purified) | 274.3 ng/μl |

Detected by IL-15 ELISA, the amount of protein obtained from IL-15 circular mRNA expression in 293T for 1-5 days are 38.9, 47.3, 68.4, 51.6, 26.4 ng/ml, respectively, indicating that the circular mRNA of the present disclosure can achieve IL-15 efficient and durable expression.

Example 7: Circular mRNA Encoding the Tumor-Specific Antigen Prostate Cancer PAP Protein to Achieve Protein Expression in 293T Cells 7.1 Experimental Methods and Procedures Based on Example 2 above, EV29 IRES, 5'homology arm 1, 3'homology arm 1, 5'spacer 1, 3'spacer 1 were used as the basic elements of circular mRNA to construct prostate cancer tumor-specific antigens acid phosphatase protein PAP (prostate acid phosphatase) cyclic mRNA. The DNA and protein sequences encoding PAP are shown in SEQ ID NO: 46 and SEQ ID NO: 47, respectively. The DNA synthesis was commissioned by Suzhou Genweiz Biotechnology Co., Ltd. to complete. Finally, a complete DNA fragment containing T7 promoter, type I PIE elements, 5'homology arm 1, 3'homology arm 1, 5'spacer 1, 3'spacer 1, EV29 IRES, and PAP coding region will be cloned into pUC57 plasmid. Plasmid DNA linearization, pre-circularized mRNA in vitro transcription, pre-circularized mRNA purification, mRNA loop reaction, circular mRNA purification to obtain circular RNA with the sequence shown in SEQ ID NO: 48, cell culture and transfection methods All are the same as 1.1 in Example 1. PAP ELISA detection kit (Thermo Fisher) was used to quantify the PAP protein expressed by 293T.

7.2 Results

TABLE 13

| Nucleic acid | Concentration |
|---|---|
| pUC57-EV29-PAP-H1S1 plasmid (purified) | 386.7 ng/μl |
| pUC57-EV29-PAP-H1S1 linearized plasmid (purified) | 294.5 ng/μl |
| EV29-PAP--H1S1 pre-circularized mRNA (purified) | 317.2 ng/μl |
| EV29-PAP-H1S1 cyclic mRNA (purified) | 268.9 ng/μl |

According to PAP ELISA detection, the amount of protein obtained from EPO circular mRNA expression in 293T for 1-5 days is 69.3, 86.4, 75.5, 52.4, 38.6 ng/ml, respectively, indicating that the circular mRNA of the present disclosure can achieve the high efficiency and durability of EPO expression.

Example 8: Circular mRNA Encoding Chimeric Antigen Receptor CD16 CAR Protein to Achieve Expression in 293T Cells 8.1 Experimental Methods and Procedures Based on the above-mentioned Example 2, EV29 IRES, 5'homology arm 1, 3'homology arm 1, 5'spacer 1, 3'spacer 1 are used as the basic elements of circular mRNA to construct a chimera cyclic antigen receptor CD16 CAR mRNA. The DNA and protein sequences encoding CD16 CAR are shown in SEQ ID NO:49 and SEQ ID NO:50, respectively. The DNA synthesis was commissioned by Suzhou Genweiz Biotechnology Co., Ltd. to complete. Finally, a complete DNA fragment containing T7 promoter, type I PIE elements, 5'homology arm 1, 3'homology arm 1, 5'spacer 1, 3'spacer 1, EV29 IRES, CD16 CAR coding region will be cloned. To the pUC57 plasmid. Plasmid DNA linearization, pre-circularized mRNA in vitro transcription, pre-circularized mRNA purification, mRNA loop reaction, circular mRNA purification to obtain circular RNA with the sequence shown in SEQ ID NO: 51, cell culture and transfection methods. All are the same as 1.1 of Example 1. Anti-CD16 monoclonal antibody-mediated flow cytometry (Thermo Fisher) was used to test the expression efficiency of the CD16 CAR protein expressed by 293T.

8.2 Results

TABLE 14

| Nucleic acid | Concentration |
|---|---|
| pUC57-EV29-CD16CAR-H1S1 plasmid (purified) | 268.5 ng/μl |
| pUC57-EV29-CD16CAR-H1S1 linearized plasmid (purified) | 221.7 ng/μl |
| EV29-CD16CAR--H1S1 pre-circularized mRNA (purified) | 375.4 ng/μl |
| EV29-CD16CAR-H1S1 cyclic mRNA (purified) | 284.3 ng/μl |

By using anti-CD16 antibody expression rate of mRNA detected annular mediated CD16CAR in the 293T. The results showed that the positive rates of CD16 CAR expression were 90.4%, 85.6%, 80.3%, 78.4%, and 60.5% in the 1-5 days of circular mRNA transfection, indicating that the circular mRNA of the present disclosure can achieve CD16 antibody efficient, long-lasting expression.

The above-mentioned embodiments of the present disclosure are merely examples to clearly illustrate the present disclosure, and are not intended to limit the implementation of the present disclosure. For those of ordinary skill in the art, other changes or changes in different forms can be made based on the above description. It is unnecessary and cannot be exhaustive of all embodiments. Any modifications within the spirit and principle of the present disclosure, equivalent substitutions and improvements should be included within the scope of the present disclosure claims.

What is claimed is:

1. A vector comprising a recombinant nucleic acid molecule for making circular RNA, the recombinant nucleic acid molecule comprising, from the 5' end to the 3' end, a 3' intron, a second exon, an internal ribosome entry site (IRES) element, a coding region, a first exon, and a 5' intron, wherein the IRES element is an Enterovirus EV29 (EV29) IRES comprising the nucleic acid sequence of SEQ ID NO: 10, wherein the recombinant nucleic acid molecule further comprises a 5' homology arm located upstream of the IRES element, and a 3' homology arm located downstream of the coding region and complementary to the 5' homology arm, wherein the recombinant nucleic acid molecule further comprises a 5' spacer located between the 5' homology arm and the IRES element, and a 3' spacer located between the coding region and the 3' homology arm.

2. A recombinant host cell, wherein the recombinant host cell comprises the vector of claim 1.

3. A pharmaceutical composition, comprising the vector of claim 1.

4. The recombinant nucleic acid molecule of claim 1, wherein the coding region encodes a target polypeptide, and the IRES element increases the expression level of the target polypeptide in eukaryotic cells as compared to the recombinant nucleic acid molecule without the IRES element.

5. A circular RNA molecule produced by the vector of claim 1 comprising EV29 IRES, wherein the EV29 IRES comprises a RNA sequence that is transcribed from the DNA sequence of SEQ ID NO: 10, wherein the circular RNA molecule comprises the first exon adjacent to the second exon, and the coding region, wherein the circular RNA molecule further comprises the 3' spacer located between the coding region and the first exon, and the 5' spacer located between the second exon and the EV29 IRES.

6. The recombinant nucleic acid molecule of claim 1, wherein the 5' homology arm comprises a sequence that is identical to SEQ ID NO: 2 or 3, and the 3' homology arm comprises a sequence that is identical to SEQ ID NO: 17 or 18.

7. The recombinant nucleic acid molecule of claim 1, wherein the 5' spacer comprises a sequence that is identical to SEQ ID NO: 6 or 7, and the 3' spacer comprises a sequence that is identical to SEQ ID NO: 52 or 53.

8. The recombinant nucleic acid molecule of claim 1, wherein the 3' intron comprises a sequence that is identical to SEQ ID NO: 4, the second exon comprises a sequence that is identical to SEQ ID NO: 5, the first exon comprises a sequence that is identical to SEQ ID NO: 15, and the 5' intron comprises a sequence that is identical to SEQ ID NO: 16.

* * * * *